(12) United States Patent
Bourg, Jr. et al.

(10) Patent No.: US 7,660,440 B2
(45) Date of Patent: Feb. 9, 2010

(54) METHOD FOR ON-LINE MACHINE VISION MEASUREMENT, MONITORING AND CONTROL OF ORGANOLEPTIC PROPERTIES OF PRODUCTS FOR ON-LINE MANUFACTURING PROCESSES

(75) Inventors: Wilfred Marcellien Bourg, Jr., Melissa, TX (US); Steven Andrew Bresnahan, Plano, TX (US); Paul Allan Martin, Celina, TX (US); John F. MacGregor, Dundas (CA); Honglu Yu, Fort Erie (CA); Mark-John Bruwer, Hamilton (CA)

(73) Assignee: Frito-Lay North America, Inc., Plano, TX (US)

( * ) Notice: Subject to any disclaimer, the term of this patent is extended or adjusted under 35 U.S.C. 154(b) by 1040 days.

(21) Appl. No.: 10/832,676

(22) Filed: Apr. 27, 2004

(65) Prior Publication Data

US 2004/0197012 A1 Oct. 7, 2004

Related U.S. Application Data

(63) Continuation-in-part of application No. 10/289,592, filed on Nov. 7, 2002, now Pat. No. 7,068,817.

(51) Int. Cl.
*G06K 9/00* (2006.01)
(52) U.S. Cl. .................. 382/110; 382/170; 382/190
(58) Field of Classification Search ............... 382/110, 382/170, 190–208, 141–143, 155–160
See application file for complete search history.

(56) References Cited

U.S. PATENT DOCUMENTS

| 4,741,042 A | 4/1988 | Throop et al. |
| 5,305,894 A | 4/1994 | McGarvey |
| 5,311,131 A | 5/1994 | Smith |

(Continued)

OTHER PUBLICATIONS

Honglu Yu and John F. MacGregor, Digital Imaging for Online Monitoring and Control of Industrial Snack Food Processes, Ind. Eng. Chem. Res., 2003, 42, 3036-3044, American Chemical Society, Published on Web May 20, 2003.

(Continued)

*Primary Examiner*—Aaron W Carter
(74) *Attorney, Agent, or Firm*—Chad E. Walter; James R. Gourley; Carstens & Cahoon, LLP

(57) ABSTRACT

A method for extracting feature information from product images using multivariate image analysis (MIA) to develop predictive models for organoleptic and other feature content and distribution on the imaged product. The imaging system is used to monitor product quality variables in an on-line manufacturing environment. The method may also be integrated into a closed-loop feedback control system in automated systems.

64 Claims, 39 Drawing Sheets
(15 of 39 Drawing Sheet(s) Filed in Color)

U.S. PATENT DOCUMENTS

| | | | |
|---|---|---|---|
| 5,335,293 A * | 8/1994 | Vanelli et al. | 382/110 |
| 5,398,818 A | 3/1995 | McGarvey | |
| 5,409,119 A | 4/1995 | Rao Datari | |
| 5,659,624 A * | 8/1997 | Fazzari et al. | 382/110 |
| 5,960,098 A | 9/1999 | Tao | |
| 6,081,740 A | 6/2000 | Gombrich et al. | |
| 6,317,700 B1 | 11/2001 | Bagne | |
| 6,341,257 B1 | 1/2002 | Haaland | |
| 6,410,872 B2 | 6/2002 | Campbell et al. | |
| 6,415,233 B1 | 7/2002 | Haaland | |
| 6,629,010 B2 | 9/2003 | Lieber et al. | |
| 2002/0164070 A1 * | 11/2002 | Kuhner et al. | 382/159 |
| 2003/0185436 A1 * | 10/2003 | Smith | 382/159 |

OTHER PUBLICATIONS

Honglu Yu and John F. MacGregor, Multivariate Image Analysis and Regression for Prediction of Coatings Content and Distribution in the Production of Snack Food, Chemometrics and Intelligent Laboratory Systems, 67 (2003) 125-144, McMaster University, Hamilton, ON., Canada.

Honglu Yu, Development of Vision-Based Inferential Sensors for Process Monitoring and Control, Thesis, Apr. 2003, McMaster University, Canada.

* cited by examiner

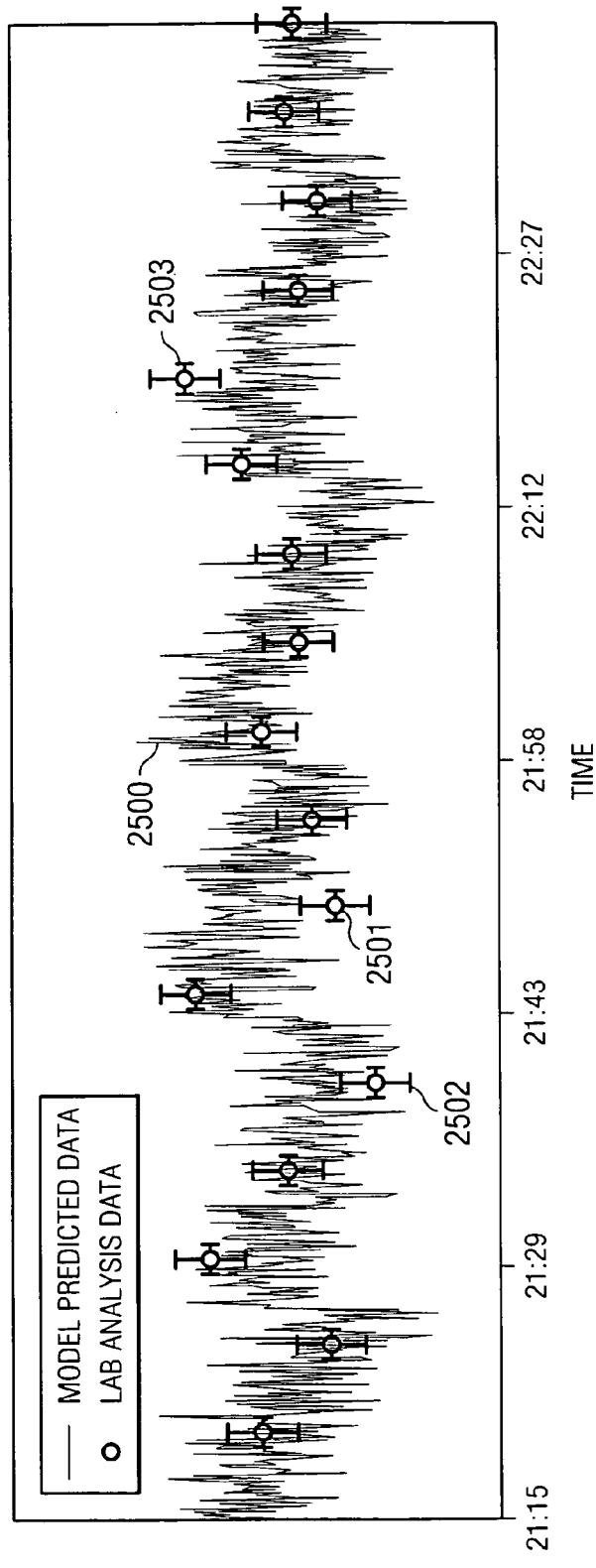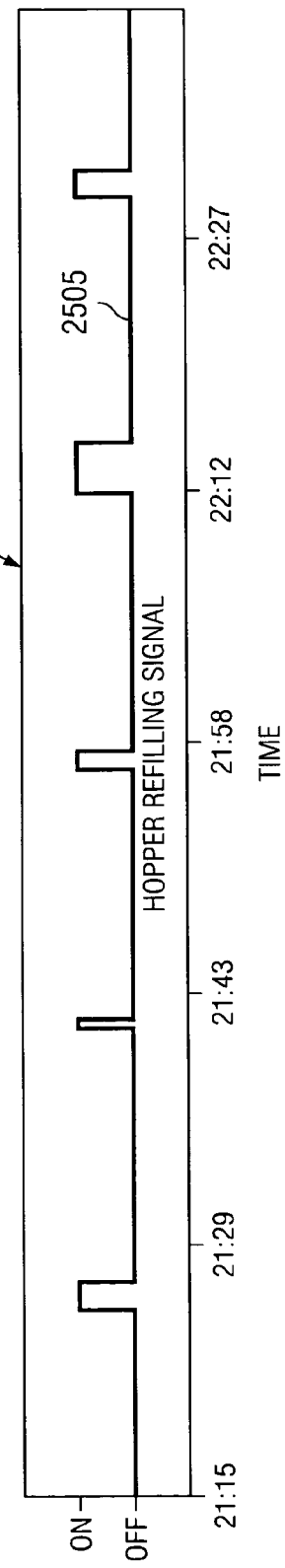

FIG. 29a
2900
FIG. 29b
2901
FIG. 29c
2902
FIG. 29d
2903
FIG. 29e
2904
FIG. 29f
2905
FIG. 29g
2906
FIG. 29h
2907
FIG. 30
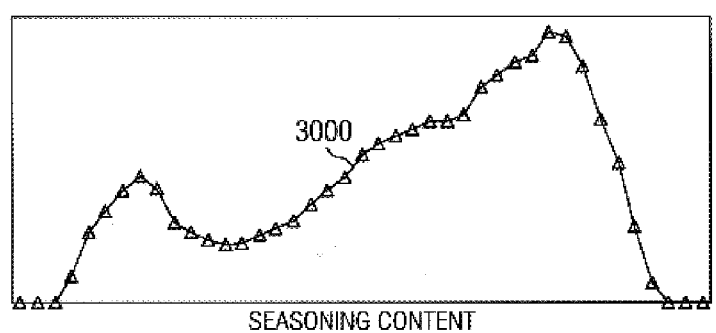
3000
SEASONING CONTENT

METHOD FOR ON-LINE MACHINE VISION MEASUREMENT, MONITORING AND CONTROL OF ORGANOLEPTIC PROPERTIES OF PRODUCTS FOR ON-LINE MANUFACTURING PROCESSES

CROSS-REFERENCE TO RELATED APPLICATION-

This application is a continuation-in-part of U.S. patent application Ser. No. 10/289,592 filed on Nov. 7, 2002, now U.S. Pat. No. 7,068,817, the technical disclosure of which is hereby incorporated herein by reference.

BACKGROUND OF THE INVENTION

1. Technical Field

The present invention relates in part to a method for ascertaining the quantity or characteristic of a product attribute in process manufacturing, and more specifically, to determining the quality or a characteristic of a food product in the food manufacturing industry. The inventive method disclosed herein utilizes on-line machine vision technology to image a foodstuff coating and through statistical analysis predicts the coating coverage based on the imaged coating concentration of the foodstuff. The methodology could be applied to the on-line measurement of any product attribute through any imaging or sensing medium where a single or multiple correlating signals can be derived.

2. Description of Related Art

The availability of inexpensive and reliable sensors for detecting product attributes while a product is moving along an assembly line or conveyor is a very important factor for successful monitoring and control in process manufacturing environments. For example, the petrochemical industry has made innovative advances in process manufacturing using multivariable modeling, in conjunction with predictive controls, due to readily available, inexpensive sensor equipment such as pressure transducers, thermocouples, and flowmeters which are easily applied to the product streams of the petrochemical industry that mainly consist of gases and liquids during the production phase.

In the past, the solids manufacturing industry encountered greater difficulty in implementing reliable sensor technology during the manufacturing phase. In its most basic form, the solids manufacturing industry used human observers to manually collate, count and determine defective products as they moved along the assembly line. Using human observers was quite expensive, prone to human error and somewhat unreliable. With the advent of digital imaging technology or "machine vision" systems, the solids manufacturing industry now has a reliable, relatively inexpensive, sensor system for monitoring and predicting selected characteristics during the production phase.

In the snack foodstuff industry, the problems of process control and quality control are of paramount importance. Although physical observation techniques have proven somewhat effective, the problem of controlling the amount of coating applied to a foodstuff still exists in the industry. The term coatings, as used herein, may include but is not limited to, seasoning, product ingredients, or other components which are applied to the foodstuff during the manufacturing process. Product coatings may also be applied to the foodstuff in other phases of production, transportation, or distribution.

For example, topical coatings are applied to snack foods to enhance or influence their taste, colour, size, texture and nutritional content. Topical coatings are primarily applied to the foodstuff by several mechanical methods, including dusting, dry coating, spraying oil on baked goods and then dusting a coating on same thereafter. It is known in the art of coating application that the consistency of the flow of coating material to the applicator and the degree of coating adhesion to the foodstuff profoundly affect the consistency of the coatings applied to the foodstuff.

The most common prior art method of quality control is to periodically sample the product and analyze the concentration of coating in a laboratory. Unfortunately, there is usually a large time delay between taking the sample and obtaining the concentration results. Likewise, the sample analysis procedure tends to be slow and destroys the sample itself. Moreover, the coating concentration is often not obtained directly, but determined by measuring the salt concentration of the sample operating on the assumption that the coating concentration and salt concentration remain constant, which is not always the case.

As such, a need in the art exists for a method of comparing product coatings to a desired product characteristic template and reliably predicting the characteristics of the actual product during the production phase in real-time or near real-time. A need also exists for a reliable and inexpensive method for assuring quality control of products manufactured on-line as the product moves from one phase of assembly to another that provides almost instantaneous monitoring and feedback control in an on-line manufacturing environment.

The qualities of texture, taste and sight of a snack food are known in the art as organoleptic properties because they are ordinarily measured by either human perception or mechanical device. These two methods of measurement are normally not useful in on-line feedback control in high-speed production because the time necessary to analyze a sample is too great to provide timely feedback to control the process. Further, the costs of manpower make it cost-prohibitive to use human perception as a feedback control mechanism in most production environments. An image-based soft sensor system predicting organoleptic properties would be ideal in the production of food products. In the prior art, there is virtually no known mechanical method to predict organoleptic qualities.

There are several specific organoleptic properties of interest in the snack food industry including blister level, toast points, taste, texture, crispness, crunchiness, and peak break force. Properties such as blister level, toast points, taste, texture, crispness, and crunchiness are ordinarily measured by human sensory response; the peak break force by mechanical equipment. Toast points are small, black grill marks left by the oven belt on the surface of the chips. Blister level is a measure of the degree of the blistering on the surface of a snack food. A taste property (unrelated to coating level) can be measured by having a human taste a sample product and compare it with a product to be measured. Taste, texture, crispness and crunchiness are all similar attributes and relate to mouth feel of the product. For example, a human first eats a reference product and subsequently eats the product to be evaluated. Peak break force is a mechanical measure of the firmness of the product. The value of peak break force is related to the break strength and hence the required force to bite and/or chew the product. For example, the peak break force is an important factor for snack chips.

Unfortunately, measuring the human sensory response has several drawbacks. First, human measurement is subjective. A large number of human testers would decrease error reporting due to subjectivity, but would increase the cost of obtaining more accurate measurements of organoleptic properties such as taste. Second, it is difficult to implement an on-line feedback control based upon human measurement. There is an impractical lag time between human measurement and feedback to the process, especially in high-speed production environments.

Consequently, a need in the art exists for a method to objectively measure and predict organoleptic properties in products, especially food products. Further, a need exists for a method and apparatus that can use the numeric values of organoleptic properties to provide on-line feedback control in high-speed production.

SUMMARY OF THE INVENTION

In accordance with one aspect of the invention there is provided a method of monitoring a process producing a characterizing product such as a snack food. The method includes the steps of sequentially capturing multivariate images of the characterizing product, each image consisting of an image array of pixel elements of measured intensity values in at least three wavelength ranges defining the dimensions for the image array. Conveniently, the wavelengths are in the visible spectrum and the pixel elements of the image array have varying intensities of the colours red, green and blue. A feature vector is created from the image array using a variety of statistical techniques according to the nature of the process and the variables affecting the operating conditions of the process. An organoleptic feature vector is a feature vector containing information about an organoleptic property of a food product. A regression method is performed on the feature vector to correlate the feature vector with a characterizing feature of the product, such as an organoleptic property. The characterizing feature is displayed for continuous monitoring of the process and may define an output for feedback control of the process.

Most preferably, a multivariate statistical projection method is applied to the image array to reduce the dimensions of the array to a low dimensional score image defined by a small number of score vectors and the feature vector is created from the low dimensional score space image. The nature of the multivariate statistical projection used is process dependent.

In a preferred embodiment, a multivariate statistical projection method is applied to an image array for a control process to reduce the dimensions to a low dimensional score space having a significant loading vector. The dimensions of the score space image data may also be reduced by appropriate masking of the data to exclude contributions to a score plot from background data in the images of the products of the process.

Another preferred embodiment of the present invention comprises a method for extracting specific product attribute information from a foodstuff, then predicting the quantity or characteristic of the foodstuff either directly or indirectly through additional correlation factors in an on-line environment. Such embodiment includes pre-processing the foodstuff image by removing background and manufacturing apparatus features from the digital image; predicting the coating concentration of the imaged foodstuff utilizing advanced statistical regression models that relate the images to a desired product characteristic; and using the same model locally to construct a histogram of coating concentrations, a graphical image related directly to coating coverage, and to provide an estimate of the spatial variance of the coating concentration.

The present invention extends to using the constructed model and real-time image data to predict the quantity, characteristic, and variance of the measured food product attribute and to generate a measurement signal; using the measurement signal to adjust the manufacturing process and control the process to deliver the desired product quality consistently; and furthermore, using the measurement signal in conjunction with other process measurements to predict additional product attribute characteristics not measured directly by a sensor. A food product attribute may include any organoleptic property of the food product.

The above, as well as additional features and advantages of the invention will become apparent in the following written detailed description.

BRIEF DESCRIPTION OF THE DRAWINGS

The patent or application file contains at least one drawing executed in colour. Copies of this patent or patent application publication with colour drawing(s) will be provided by the Office upon request and payment of the necessary fee.

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

FIGS. 25a and 25b are graphical depictions of seasoning concentration level versus time compared with the detection of the seasoning hopper refill signal according to one embodiment of the inventive method disclosed herein;

FIGS. 29a through 29h represent colour images of product with various seasoning coatings, which correspond with the numerals placed on FIG. 28 according to one embodiment of the inventive method disclosed herein;

FIG. 30 is a seasoning distribution plot of image five in FIG. 29 according to one embodiment of the inventive method disclosed herein;

Figure 1:
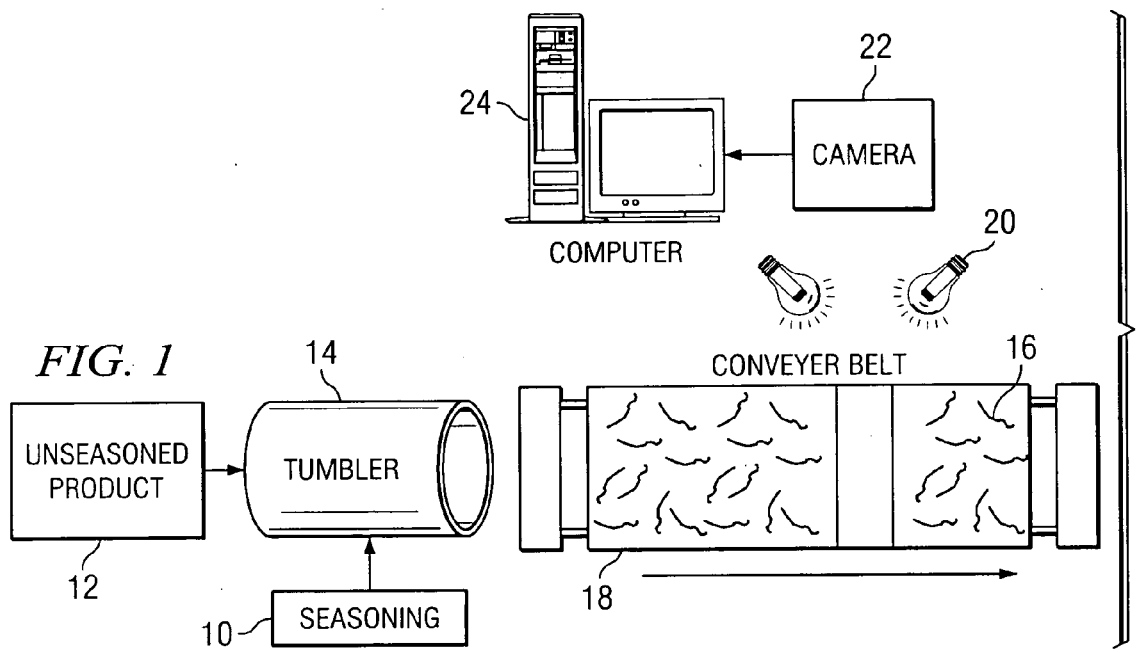
FIG. 1 is a schematic diagram depicting a preferred embodiment of the present invention integrated into an on-line food manufacturing environment according to one embodiment of the inventive method disclosed herein.

Where used in the various figures of the drawing, the same numerals designate the same or similar parts. Furthermore, when the terms "top," "bottom," "first," "second," "upper," "lower," "height," "width," "length," "end," "side," "horizontal," "vertical," and similar terms are used herein, it should be understood that these terms have reference only to the structure shown in the drawing and are utilized only to facilitate describing the invention.

DETAILED DESCRIPTION OF THE INVENTION

Embodiment of Food Coating Analysis

One embodiment of the inventive method disclosed herein consists of utilizing known digital imaging technology to capture and process digital images of coatings on foodstuffs, as the foodstuffs are moving on-line, to extract desired features from the image, and then to construct a model that predicts the characteristic level on the imaged product by relating the pre-processed product images to a desired product characteristic via Multivariate Image Analysis (MIA) or other statistical regression regimes, and locally constructing a histogram that depicts the correlation of coating concentration to coating coverage. In a preferred embodiment, the inventive method disclosed herein is applied to control processes in the food manufacturing industry and, more specifically, to determine the seasoning coating applied to snack foods in the food processing industry. A characterizing product is a product with a characteristic attribute or feature measurable through the process disclosed in this invention.

Traditional image analysis methods are known in the art with respect to a variety of applications in the food industry, such as fruit and vegetable sorting, automatic partitioning, inspection for foreign matter or objects, and general packaging applications. However, digital imaging applications pertaining to coating on food items are virtually nonexistent. With regard to the digital imaging component of the inventive method disclosed herein, much of the literature on digital imaging processing involves methods for altering the visual image in some way to make the image more visually appealing or to extract information on the shapes, boundaries or location of various observable features. In this vein, traditional image processes serve as automated, machine vision systems performing operations many times faster and far more precisely than human observers or operators.

Most foods typically are produced by coating the base product with flavored coatings. Coatings plays an important role in both the flavor and the appearance of a food or snack, and greatly influences their acceptability. Coatings may influence the organoleptic properties of a food. The usual procedure of taking infrequent samples and analyzing for the coatings concentration in the laboratory yields very little information, except long-term trends and with no information on the food coating distribution. Furthermore, laboratory analysis is a time-consuming and expensive procedure. Clearly there is a tremendous opportunity for an on-line imaging system.

A typical setup for using imaging technology in a food-manufacturing environment is shown in FIG. 1. Coatings 10, in this example "seasoning," and unseasoned food product 12 are mixed in a tumbler 14 and then the coated food product 16 is conveyed via a moving belt 18 to subsequent operations such as packaging or baking. An electromagnetic radiation source, in this example a visible spectrum lighting system 20, and RGB camera system 22 are mounted above the moving belt 18 and images of the products 16 are sent to a computer 24 for analysis by the methods disclosed herein. The electromagnetic radiation source 20 could also be configured to emit radiation from the various bands of the electromagnetic spectrum, including but not limited to, the infrared spectrum and ultraviolet spectrum and be configured to emit single and multiple wavelengths of electromagnetic radiation in the desired spectrum. The choice of sampling interval depends upon the objectives for each process. The time required for processing one image of product 16 is less than one second.

The inventive method disclosed herein could also find application in determining other foodstuff qualities such as the number of toast points located on the product, the texture of the product, and/or the number of blisters on the product. Likewise, it will be appreciated that the inventive method disclosed herein will find applications in various other industries as will be exemplified. Another embodiment applying the inventive principles of multivariate image analysis with application toward flame study is also discussed herein. Thus, the specification, claims and drawings set forth herein are to be construed as acknowledging and non-exclusionary as to these other applications and embodiments.

The RGB (red-green-blue) space is the most commonly used colour space in electronic cameras. The colour of each pixel in this space is characterized by numerical values (normally integers from 0 to 255) of its R, G and B channels. A colour image can be expressed as a 3-way matrix. Two dimensions represent the x-y spatial coordinates and the third dimension is the colour channel. Without considering the spatial coordinates of pixels, the image matrix can be unfolded and expressed as a 2-way matrix.

$$I_{N_{row} \times N_{col} \times 3} \xrightarrow{unfold} I_{N \times 3} = \begin{bmatrix} c_{1,r} & c_{1,g} & c_{1,b} \\ \vdots & \vdots & \vdots \\ c_{i,r} & c_{i,g} & c_{i,b} \\ \vdots & \vdots & \vdots \\ c_{N,r} & c_{N,g} & c_{N,b} \end{bmatrix} = \begin{bmatrix} c_1 \\ \vdots \\ c_i \\ \vdots \\ c_N \end{bmatrix}$$

I is three-way image matrix with image size $N_{row} \times N_{col}$. I is the unfolded two-way image matrix. N is the number of pixels in the image, $N = N_{row} \times N_{col}$. $C_{i,r}, C_{i,g}, C_{i,b}$ (i=1,...,N) are the intensity values of the R, G and B channels for pixel i. $c_i$ (i=1, ..., N) is the i-th row vector of I, which represents the colour values of pixel i. In the following text, the two-way matrix I represents an image.

Several factors may influence the colour of a pixel-size seasoned foodstuff. The colour of a pixel would be decided by the colour of the non-seasoned part, the colour of the coatings particles, the concentration of coatings and the lighting condition of this piece of product. If these factors, other than coating concentration, are lumped together into one factor $\phi$, referred to as the imaging condition, the colour of one pixel $c_i$ can be expressed as a function of the local imaging condition $\phi_i$ and local coatings concentration $y_i$.

$$c_i = f(y_i, \phi_i) \quad (1)$$

Figure 2:
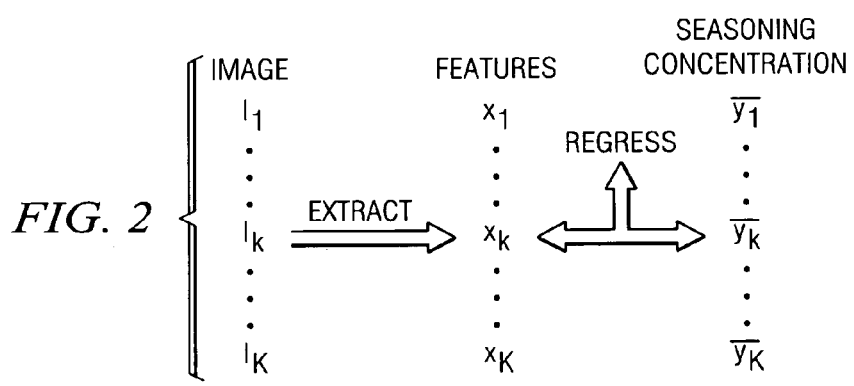
FIG. 2 is a schematic diagram, which depicts the fundamental model for imaging a food product, extracting image features, and performing a statistical regression to determine the coating concentration according to one embodiment of the inventive method disclosed herein.

FIG. 2 represents the schematic model depicting the determination of coating on a foodstuff via regression analysis. For example, consider a data set of K colour images $I_k$ and their corresponding laboratory analyzed average coatings concentration $\bar{y}_k$ (k=1, ..., K). A model to predict coatings concentration can be obtained by regressing the coatings concentrations against the features extracted from one or more images. Feature extraction converts the image into a feature vector that contains information most related to coatings concentration, and is therefore, a critical step to achieve desired prediction results. An organoleptic feature vector is a feature vector containing information about an organoleptic property of a food product. After feature extraction, a model is developed by regressing feature variables and coatings concentration. Different regression methods may be used including Principal Component Regression (PCR), Multivariate Linear Regression (MLR), and Artificial Neural Networks (ANN). In the preferred embodiment, Partial Least Squares (PLS) regression is employed because of the high correlation among the feature variables.

Multi-way Principal Component Analysis (MPCA)

A colour image is a multivariate image composed of three variables (R, G and B channels). The inventive method herein is developed using Multivariate Image Analysis (MIA) techniques, which are based on multi-way Principle Component Analysis (PCA). Multi-way PCA is equivalent to performing PCA on the unfolded image matrix I.

$$I = \sum_{a=1}^{A} t_a p_a^T$$

where A is the number of principal components, the $t_a$'s are score vectors and the corresponding $p_a$'s are loading vectors.

Since the row dimension of the I matrix is very large (equal to 307,200 for a 480*640 image space) and the column dimension is much smaller (equal to 3 for an RGB colour image), a kernel algorithm is used to compute the loading and score vectors. In this algorithm, the kernel matrix ($I^T I$) is first formed (for a set of images, the kernel matrix is calculated as $$\sum_k I_k^T I_k \Bigg)$$

and then singular value decomposition (SVD) is performed on this very low dimension matrix (3*3 for colour image) to obtain loading vectors $p_\alpha$ ($\alpha=1, ... A$).

After obtaining loading vectors, the corresponding score vectors $t_\alpha$ are then computed via $t_a = I p_a$. Since the first two components normally explain most of the variance, instead of working in original 3-dimensional RGB space, working in the 2-dimensional orthogonal $t_1$-$t_2$ score space allows the images to be more easily interpreted.

Datasets for Models

When building the model of the embodiment discussed below, the first step is to collect an adequate set of datasets. A successful model requires a set of sample images including both non-seasoned and seasoned product samples with varied coatings levels. For each seasoned product image, the corresponding average coating is obtained by laboratory analysis. All the images are collected from the on-line camera system. Grab samples (manually-obtained samples) of the food product corresponding to those images are taken to the lab for analysis. The images are all 480×640 RGB colour images, with 256 intensity levels in each channel. Table 1 shows details about the training and test datasets for each product. The datasets include both non-seasoned and seasoned product samples (coatings levels are varied) which are initially imaged by digital imaging equipment. For each seasoned product image, the corresponding average coating is obtained by laboratory analysis.

Figure 51A:
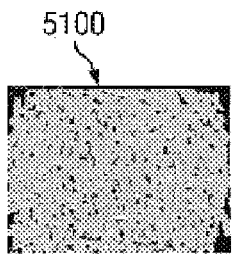
FIGS. 51a through 51i represent colour images of three different food products with various levels of seasoning coatings.
Figure 51B:
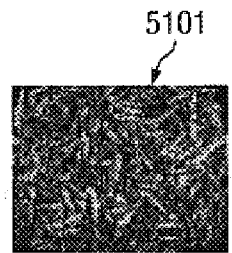
Figure 51C:
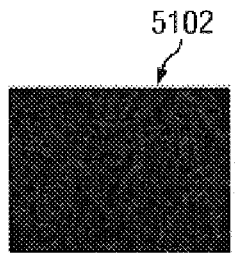
Figure 51D:
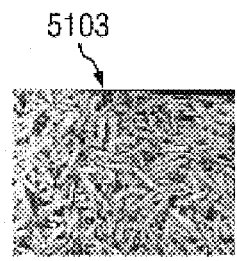
Figure 51E:
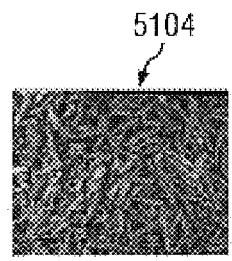
Figure 51F:
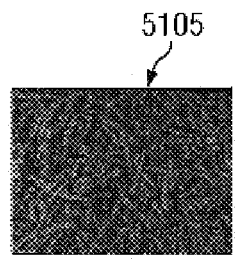
Figure 51G:
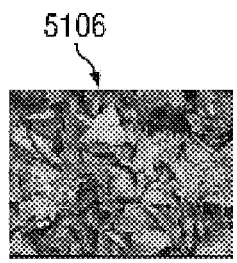
Figure 51H:
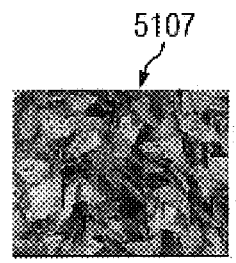
Figure 51I:
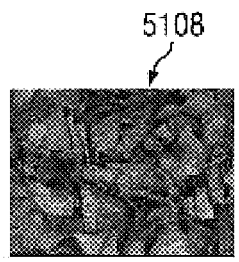

To illustrate a preferred embodiment of the method disclosed herein, three types of snack product were collected, imaged and their seasoning concentrations obtained in laboratory analysis. All images of samples were taken with digital imaging equipment and were 480×640 RGB colour images, with 256 intensity levels in each channel. Half of the samples were used as the training set and the other half as a test set. These three types of product are referred to as type A, B, and C, respectively. Three different levels of seasoning were applied to these three types of product. FIG. 51*a*, FIG. 51*d* and FIG. 51*g* correspond to product A; FIG. 51*b*, FIG. 51*e* and FIG. 51*h* correspond to product B; and FIG. 51*c*, FIG. 51*f* and FIG. 51*i* correspond to product C. Samples of product A in FIGS. 51*a* through 51c (5100, 5101 and 5102) were collected off of the manufacturing line (off-line); samples of product B in FIGS. 51*d* through 51*f* (5103, 5104 and 5105) and samples of product C in FIGS. 51*g* through 51*i* (5106, 5107 and 5108) were collected while located on the manufacturing line (on-line).

The product samples 5100, 5103 and 5106 have no seasoning; the product samples 5101, 5104, and 5107 have moderate seasoning; and the product samples 5102, 5105, and 5108 have a relatively high amount of seasoning.

Product A (5100, 5101, and 5102) was sampled off-line, and 83 samples were taken where 40 were used for training and 43 were used for testing. Product B (5103, 5104, and 5105) was sampled on-line, and 180 samples were taken where 90 were used for training and 90 were used for testing. Product C (5106, 5107, and 5108) was sampled on-line, and 110 samples were taken where 55 were used for training and 55 were used for testing.

Feature Extraction Methods

Table 1 outlines six methods used to extract image features as part of the inventive method disclosed herein. These methods can be further classified into two categories: overall feature methods and distribution feature methods. In the following explanation, product C is used as the example to illustrate the six feature extraction methods.

TABLE 1

Methods of Extracting Image Features

| Method # | Feature variables |
|---|---|
| Overall Feature Methods | | |
| 1 | Average colour |
| 2 | Loading vector of first principle component |
| Distribution Feature Methods | | |
| 3 | Two-dimensional histogram in $t_1$-$t_2$ score space |
| 4 | Histogram based on linear projection in $t_1$-$t_2$ space |
| 5 | Cumulative histogram based on linear projection in $t_1$-$t_2$ space |
| 6 | Cumulative histogram based on correlation property segmentation |

Overall Feature Methods

In these types of methods, information from all pixels is used to obtain some overall colour feature. Two methods are presented: method 1 (average colour) and method 2 (first loading vector from PCA). In both methods, the dimension of the feature vector is three, one element for each of the three colour channels. Since colour is a function of coatings concentration, the overall colour features will be correlated with the average coatings concentration. Models can be further built based on this correlation relationship.

Method 1: Average Colour

Average colour is a straightforward way to extract features. In this method, the feature variables are just the average values for each channel taken over the whole image.

Method 2: Loading Vector of First Principal Component

When performing a PCA (without mean-centering) on an image, the first loading vector represents the direction of greatest variability of the pixel intensities in the RGB colour space. As can be verified in the examples, the first principal component of PCA (without mean-center) explains most of the variance (over 97%). Therefore, it is also a good overall descriptor of the image colour and can be used as a feature variable.

Figure 3A:
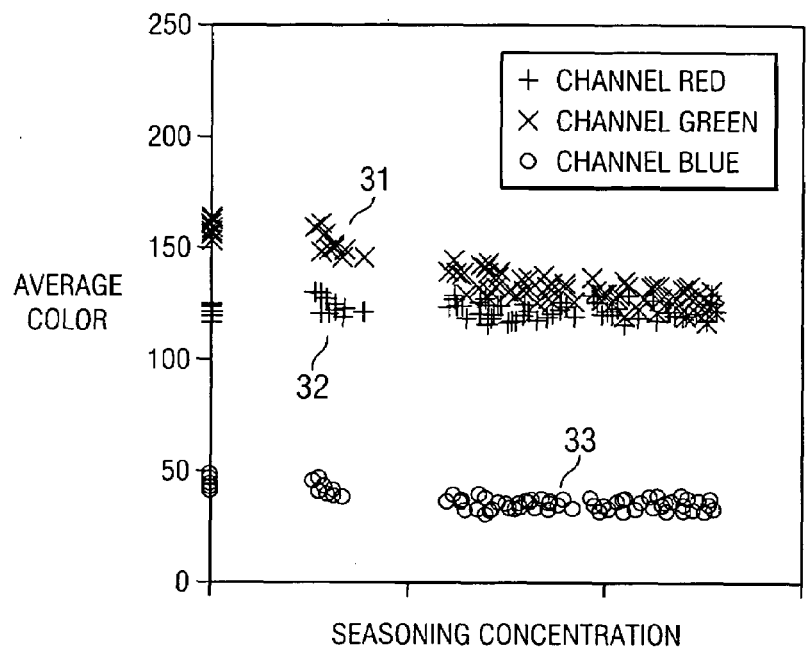
FIGS. 3a and 3b are graphical depictions of the relation between product seasoning concentration versus average colour of the product and the first principal component loading vector, respectively.
Figure 3B:
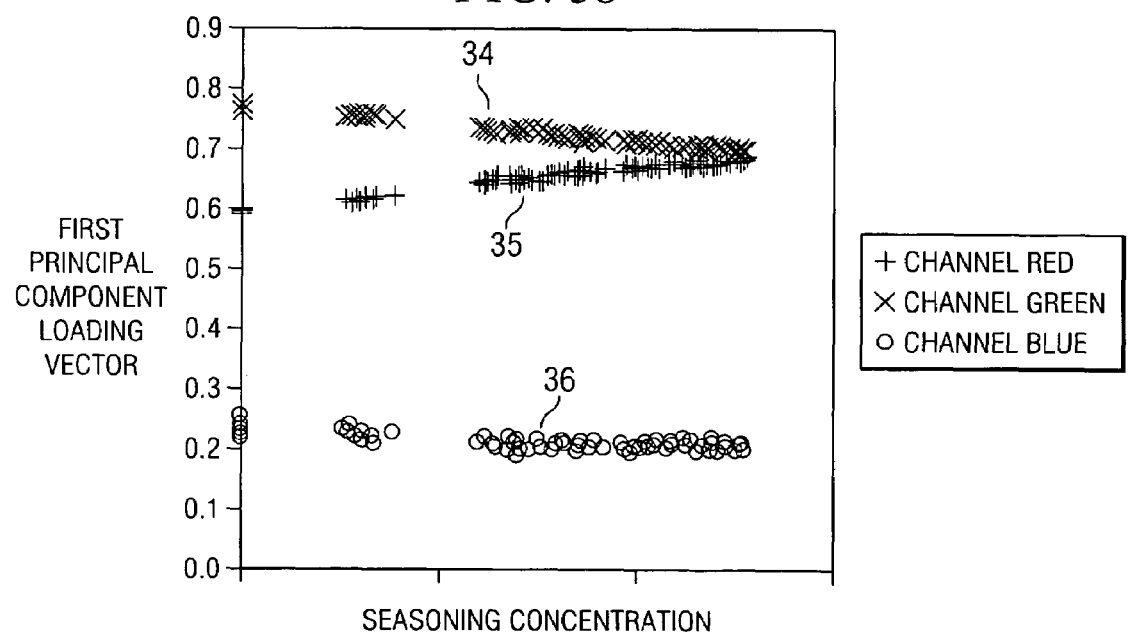

FIG. 3 demonstrates the relation between average colour, first principal component loading vector and the seasoning coating concentration features. Green channel data points 31, red channel data points 32, and blue channel data points 33 are shown in the FIG. 3-$a$ plotted as seasoning concentration versus average colour. Green channel data points 34, red channel data points 35, and blue channel data points 36 are shown in FIG. 3-$b$ plotted as seasoning—concentration versus first principal loading component (PC) loading vector. Regression models using these features may then be developed based on feature versus concentration data.

As shown in equation (1), the colour of a pixel is a function of both the local coating concentration and other imaging conditions. Although pixels containing the same amount of coating concentration may exhibit variations in colours, it is reasonable to assume that pixels having the same colour contain the same amount of coating. For an image, the number of pixels, whose colour is [r g b] where r, g and b are integers from 0 to 255, can be counted as $n_{[r,g,b]}$. If the coatings concentration for each of these pixels is $y_{[r,g,b]}$, then the average coatings concentration for the whole image can be calculated as:

$$\bar{y} = \sum_r \sum_g \sum_b y_{[r,g,b]} \frac{n_{[r,g,b]}}{N} \quad r, g, b = 0, 1, \ldots, 255 \quad (2)$$

Notice that equation (2) has a linear model structure. For each image, $n_{r,g,b}/N$, which is a 256×256×256 three-dimensional relative histogram, can be used as feature variable. Estimation of $y_{[r,g,b]}$ can be obtained through a linear regression between the observed values of $n_{r,g,b}/N$ from the images and average coating concentration from laboratory analysis. However, this model is neither robust nor practical because to obtain such a 3-D histogram for each image is time consuming and even if the three-dimensional histogram is computed, the large number ($256^3$=16,777,216) of feature variables are extremely highly correlated and generally have a very low signal-to-noise ratio. This leads to a very ill-conditioned and poor model for predicting the average coatings level.

To reduce the number of feature variables, the colour space can be divided into L classes, such that pixels falling in a class contain a similar amount of coatings. In this form, each class becomes a new histogram bin and the average coatings concentration for an image can be obtained by:

$$\bar{y} \approx \sum_{j=1}^{L} y_j \frac{n_j}{N} \quad (3)$$

where $n_j$ and $y_j$ are the pixels and average coating concentration belonging to class j. The model structure remains linear as long as the assumption that pixels in the same class represent a similar amount of coating is not flagrantly violated.

There is a strong relationship between the average colour and the first loading vector of MPCA as used in the overall method 1 and 2 respectively. In method 2, a non-mean-centered PCA is performed on each image and first principal component explains most of the variation. In this situation, the direction of average colour $\bar{c}$ is approximately equal to the direction of first loading vector $p_1$.

$$\bar{c} \cdot p_1 \approx \|\bar{c}\| \Rightarrow p_1^T \approx \frac{\bar{c}}{\|\bar{c}\|}$$

Therefore, the first loading vector is approximately equal to normalized average colour and instead of first loading vector or MPCA, the normalized average colour could be used as feature variables and should give a similar performance as method 2.

Lighting variations will have an influence on overall feature methods. Lighting variation comes from a non-uniformly distributed light source, a non-flat orientation of the product, or overlapping among the pieces of product. Suppose that the lighting condition and colour has the following linear relationship for each pixel location:

$$c_i = L_i \cdot R_i, \ i=1,\ldots,N$$

in which, $c_i$, $L_i$, $R_i$ are colour, local lighting condition and colour, respectively, under an ideal reference lighting condition for pixel i. Assume the light source and the image scene are independent. The average colour of an image is equal to $$\bar{c} = \bar{L} * \bar{R}$$

Any variation in lighting will directly influence the value of average colour.

Since the first loading vector is approximately the normalized colour, then $$p_1^T \approx \frac{\bar{c}}{\|\bar{c}\|} = \frac{\bar{L} \cdot \bar{R}}{\|\bar{L} \cdot \bar{R}\|} = \frac{\bar{R}}{\|\bar{R}\|}$$

Therefore, this lighting effect is canceled when using the first loading vector or normalized average colour. When evaluating the results from method 1 and method 2, test set images have similar overall lighting conditions as the training set images, and so both method 1 and method 2 generate good prediction results. But when using small image windows as test images, lighting conditions vary from window to window. Since method 2 is less sensitive to lighting variation, method 2 will generally have a smaller prediction error than method 1. However, this deduction is based on a linear effect of lighting, which may not always exist in practice. Therefore, method 2 is still influenced by lighting condition variation and shows increasing prediction error when window number increases.

Distribution Methods

Models based on distribution features have an advantage over the overall feature models, in that information from every class is taken into account rather than using only a global description of the image. Distribution feature models are pixel-level models, meaning that in distribution feature models, regression coefficients are the estimates of the coatings concentration for each bin.

$$y = \hat{y}_{Bin_1} x_1 + \hat{y}_{Bin_2} x_2 + \ldots + \hat{y}_{Bin_B} x_B$$

For one pixel with colour value c, if it is determined that this pixel is falling into $i^{th}$ bin, the coating concentration for this pixel can be estimated as $\hat{y}_{Bin_i}$. Therefore, distribution feature models can be seen as pixel-level models because the coating concentration for each pixel can be estimated.

Three different methods are now presented to divide the colour space pursuant to the distribution models discussed below. In each method, MPCA is first performed to reduce the dimension and all the operations are then carried out in the $t_1$-$t_2$ score space. As discussed in further detail below, method 3 uses a simple 32×32 two-dimensional histogram in $t_1$-$t_2$ score space. Methods 4 and 5 are based on a one-dimensional histogram and a cumulative histogram, respectively, obtained by a further linear projection in $t_1$-$t_2$ score space. Method 6 begins with a fine 256×256 two-dimensional histogram in $t_1$-$t_2$ space, then combines the histogram bins having similar coatings based on covariance properties and a new one-dimensional cumulative histogram is eventually used as the feature vector.

Method 3: Two-Dimensional Histogram in $t_1$-$t_2$ Score Space

Figure 4A:
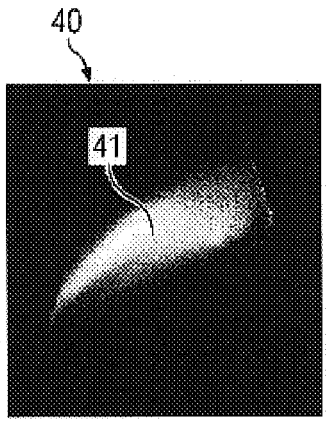
FIGS. 4a, 4b and 4c are image score plots for three separate images of a non-coated, low-coated, and high-coated foodstuff according to one embodiment of the inventive method disclosed herein.
Figure 4B:
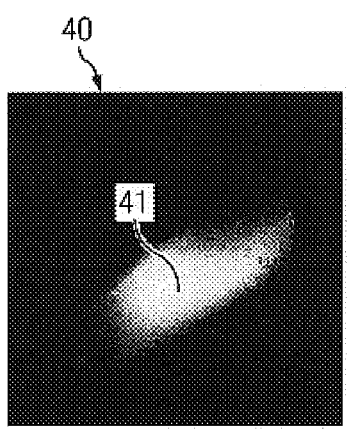
Figure 4C:
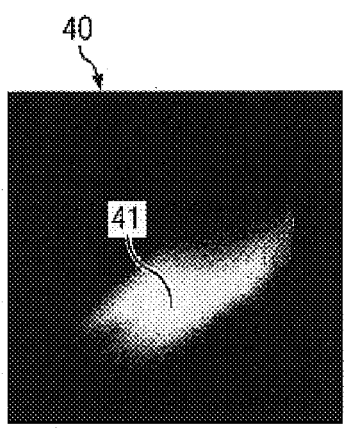

One effective way to reduce the number of histogram bins is to perform MPCA on training images and find a $t_1$-$t_2$ plane that contains most of the information. The images are corrected by subtracting the average colour of non-seasoned product images in order to obtain a plane that captures most of the difference between coated and non-coated product. Three scatter score plots ($t_2$ vs. $t_1$) of three sample images of product C are illustrated in FIGS. 4-a, 4-b, and 4-c. Since similar colours in the original image will yield almost identical ($t_1$, $t_2$) score combinations, many points overlap in this scatter plot. Following Geladi, et al. ("*Multivariate Image Analysis*" 1996, Wiley, New York, 1996), the score plots ($t_1$ vs. $t_2$) are constructed as two-dimensional histograms with a grid of 256×256 bins. This two-dimensional histogram is then colour-coded depending upon the number of pixels in each bin using a colour scheme ranging from dark colours 40 (e.g. black) representing bins with a low number of pixels to light colours 41 (e.g. white) representing bins having the highest pixel density. From these plots, it is observed that the position of pixels in the score space strongly correlates with coating concentration.

Figure 5:
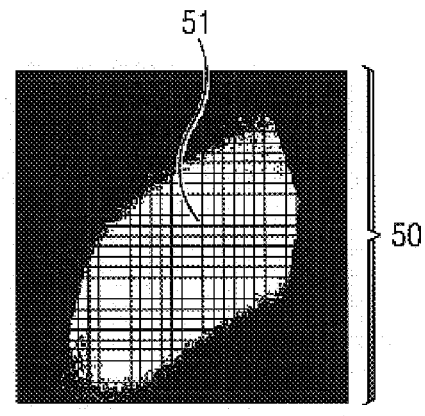
FIG. 5 represents a one dimensional histogram constructed by taking an image score plot and dividing it into 32×32 blocks for use in developing a feature vector for each image according to one embodiment of the inventive method disclosed herein.
Figure 16A:
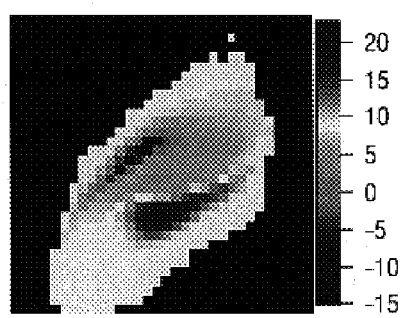
FIG. 16a through 16d are graphical depictions of the estimated coating concentration for each histogram bin calculated according to methods 3, 4, 5 and 6 according to one embodiment of the inventive method disclosed herein.
Figure 16B:
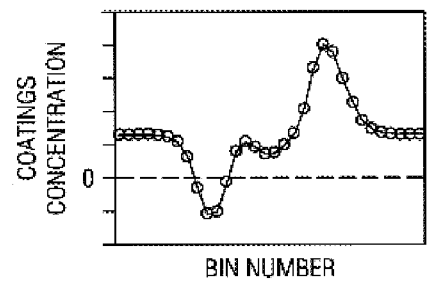
Figure 16C:
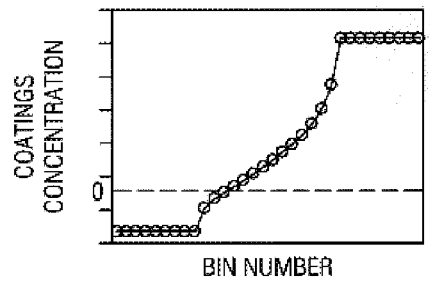
Figure 16D:
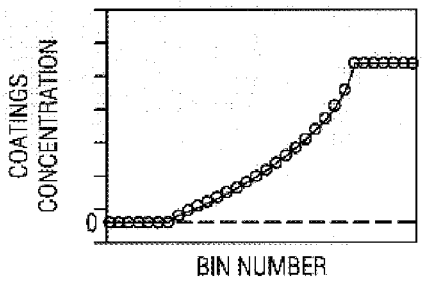

In the $t_1$-$t_2$ space, if each score variable is divided into only 32 bins, the number of final bins would be reduced to $32^2 = 1,024$. Though it is still a large number, it is much less than in three-dimensional space ($32^3 = 32,768$) or directly using the score plot ($256^2 = 65,536$). The number of bins can be further reduced by simply dividing the score variables into fewer bins and enlarging the bin size; however, at some point, the precision may begin to degrade. The 32×32 two-dimensional histogram can be unfolded into a row vector and used as feature vector for each image. This method is equivalent to dividing $t_1$-$t_2$ score plots into 32×32 blocks and summing the intensity values within each block as illustrated in FIG. 5 and FIG. 16a. The white pixels 50 indicate the location of pixels for all the training images.

Method 4 and 5: One-Dimensional Histogram/Cumulative Histogram Based on a Linear Projection in $t_1$-$t_2$ Plane The (32×32) two-dimensional histograms still have many bins, which may lead to an ill-conditioned regression. Furthermore, not all shifts of the histogram in the $t_1$-$t_2$ space will be related to coating concentration changes.

Figure 6:
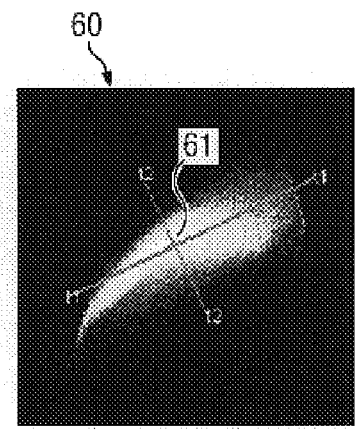
FIGS. 6 and 7 illustrate an alternative approach to divide an image score plot by creating a cumulative histogram based on vector projection according to one embodiment of the inventive method disclosed herein.
Figure 7:
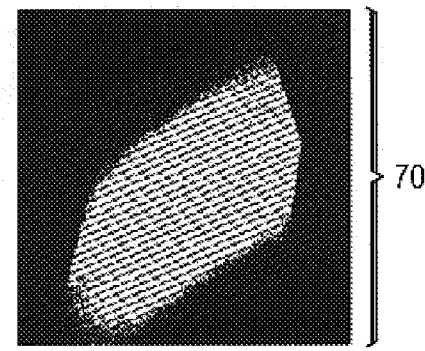

The dimension can be reduced to one by finding a projection direction in the $t_1$-$t_2$ space, along which mainly imaging condition changes, not the coating concentration changes, cause the variation of colour. One approach to find such a direction is to perform another PCA on only non-coated product images (i.e. a control process) in the $t_1$-$t_2$ space. In non-coated product images, all the colours represent equivalent coating concentration and the first component of this PCA would indicate the direction that has the most variation caused by changing imaging conditions and changing base product colour. The first component is therefore the significant loading vector $t_s$. Projection of all the histogram bins along this direction will cancel out most of the influential imaging condition variations if the PCA model has been built on a training set of non-coated product images which is representative of the variations one normally would encounter. After projection, a one-dimensional histogram can be obtained (Method 4). A cumulative histogram can also be used as feature variables to describe the distribution that will normally have a better signal to noise ratio than the one-dimensional histogram alone (Method 5). FIGS. 4-a, 4-b and 4-c are examples of score plot one-dimensional histograms based on a linear projection in the $t_1$-$t_2$ plane acquired from three sample images of product C. FIG. 5 depicts the division of the score plot into 32×32 histogram bins 51. FIGS. 6 and 7 illustrate this projection approach.

Figure 8A:
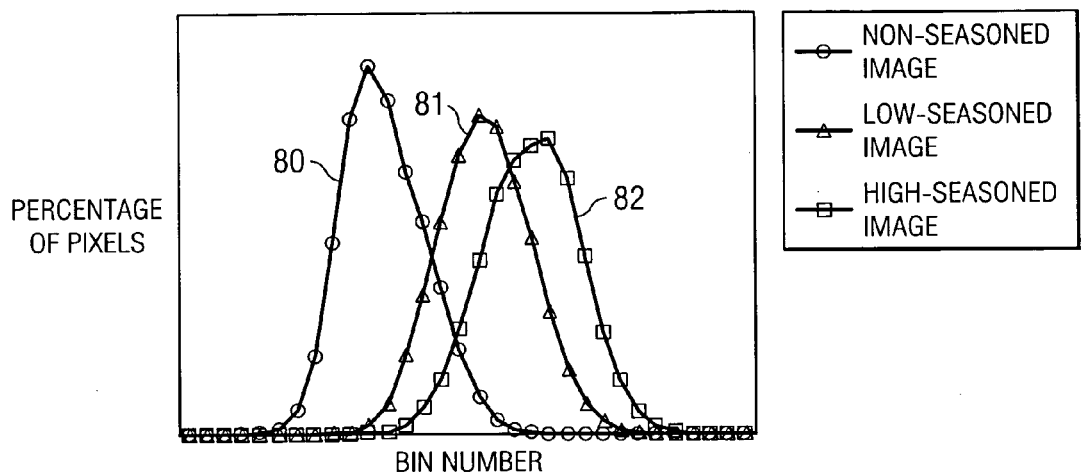
FIGS. 8a and 8b are graphical representations of the one-dimensional histogram and cumulative histogram points, respectively, obtained for each analyzed non-seasoned image, low-seasoned image and high-seasoned image according to one embodiment of the inventive method disclosed herein.
Figure 8B:
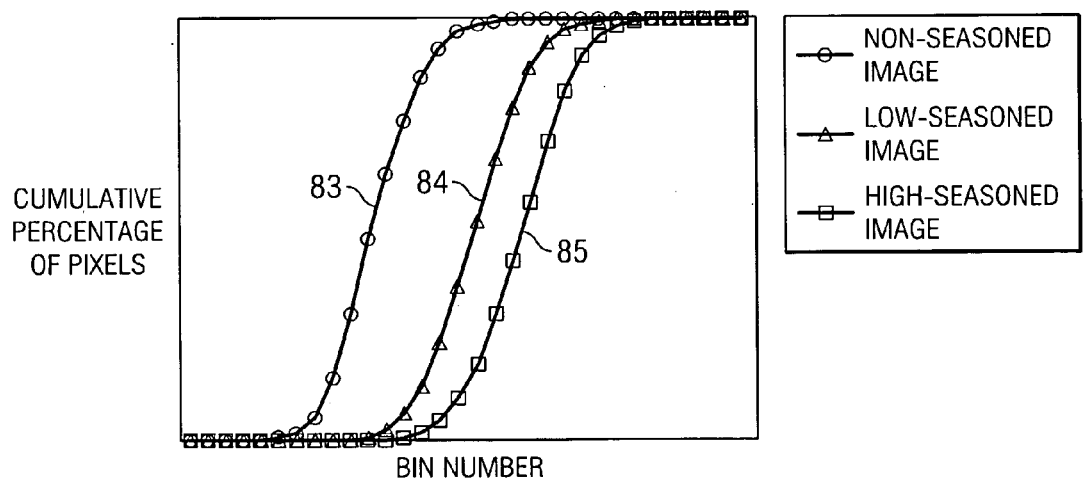

To find the parallel line direction for the bins 51, another PCA (mean-centered) is performed on the $t_1$-$t_2$ score data of the non-coated product images 60 as shown in FIG. 6. In FIG. 7, contrary to method 3 previously discussed, the $t_1$-$t_2$ space is divided into long parallel bins 70. The first component direction in this space ($t_1$-$t_1$ line 61 in FIG. 6) indicates the direction of largest variance, which is due mainly to imaging condition changes. For each training image, the pixels are first projected onto the $t_1$-$t_2$ plane using the MPCA model for the training images. Then the scores are projected along the first component direction obtained from the PCA performed on the non-coated image score plot. In this way, the original three-dimensional RGB space is simplified to only one dimension. The one-dimensional histogram for non-seasoned images 80, low seasoned images 81, and high seasoned images 82 (according to method 4) and cumulative histogram for non seasoned images 83, low seasoned images 84 and high seasoned images 85 (according to method 5) can be computed and plotted as shown in FIGS. 8-$a$ and 8$b$ where 32 bins are used. The 32 histogram and cumulative histogram points obtained for each image are then used as features to regress against the average coating content for these images.

Method 6: Cumulative Histogram Based on Correlation Property Segmentation In method 4 and method 5, a linear projection is used to convert the two-dimensional histogram projection into a more robust one-dimensional histogram. However, linear projection may not achieve very reliable results because imaging conditions often have a nonlinear influence on pixel colour.

In method 6, a 256×256 histogram in $t_1$-$t_2$ space is created, as is done in method 4 and method 5, and then histogram bins are combined that are expected to contain similar amount of coating concentration into a class by calculating the covariance properties between the histogram elements and coating concentration.

For image I, its relative histogram is expressed as:

$$P_I = [P_I(B_2)\ P_I(B_2)\ \ldots\ P_I(B_M)]$$

M is the total number of histogram bins. For a 256×256 histogram in $t_1$-$t_2$ space M equals to $256^2$=65,536. $P_I(B_i)$ is the pixel counts for bin $B_i$ divided by the total number of image pixels, which is an estimation of probability of pixels falling into the $i^{th}$ bin.

A matrix $\Gamma$ can be constructed by stacking relative histograms for all the training images together:

$$\Gamma = \begin{bmatrix} P_{I_1} \\ P_{I_2} \\ \vdots \\ P_{I_K} \end{bmatrix} = \begin{bmatrix} P_{I_1}(B_1) & P_{I_1}(B_2) & \cdots & P_{I_1}(B_M) \\ P_{I_2}(B_1) & P_{I_1}(B_2) & \cdots & P_{I_2}(B_M) \\ \vdots & \vdots & \ddots & \vdots \\ P_{I_K}(B_1) & P_{I_1}(B_2) & \cdots & P_{I_K}(B_M) \end{bmatrix} = [P(B_1)\ P(B_2)\ \cdots\ P(B_M)]$$

$P(B_i)$ is the $i^{th}$ column vector of matrix $\Gamma$ for each bin $B_i$.

The 256×256 histogram in $t_1$-$t_2$ space is preferred, which equates each histogram bin as representing pixels with similar colour and similar coating content. To combine histogram bins with similar coating content together, a common property among them must be acquired as set forth below.

From equation (1), it is known that colour is a function of coating level and imaging condition and that these two factors are independent. Considering two histogram bins having similar coating content y, which are denoted as $B_j$ and $B_k$, for image I it is calculated by:

$$P_I(B_j)=P_I(y)P_I(\phi_j),\ P_I(B_k)=P_I(y)P_I(\phi_k)$$

that $\phi_j$ and $\phi_k$ are the local average imaging conditions. For all the training images collected over a short period of time, often the only factor changing from image to image is the coating concentration distribution while overall imaging conditions (such as lighting distribution) remain the same. Therefore, $$P_{I_1}(\phi_j)=P_{I_2}(\phi_j)=\ldots=P_{I_K}(\phi_j)=s_j,\ P_{I_1}(\phi_k)= P_{I_2}(\phi_k)=\ldots=P_{I_K}(\phi_k)=s_k \quad (5)$$

in which $s_j$ and $s_k$ are two scalars. So, $$P(B_j)=P(y) \cdot s_j,\ P(B_k)=P(y) \cdot s_k$$

Therefore, for two histogram bins $B_j$ and $B_k$, which correspond to the same amount of local coatings concentration y, $P(B_j)$ and $P(B_k)$ will have the same direction but different magnitude. The covariance between $P(B_j)$ and any other K-element vectors $z_1$, $z_2$ is computed by:

$$cov_1 = cov[P(B_j), z_1] = cov[P(y), z_1] \cdot s_j,$$

$$cov_2 = cov[P(B_j), z_2] = cov[P(y), z_2] \cdot s_j$$

The scalar can be canceled by computing the phase angle of the observed point in the space of $cov_1$ vs. $cov_2$.

$$\arg(cov_1, cov_2) = \theta(y)$$

If $\theta(y)$ and y have a one-to-one mapping relationship, $\theta$ can be segmented into several bins and each bin should represent a different coating concentration.

The choice for $z_1$ and $z_2$ is not unique. Setting $z_1$ as the average coating level is a natural choice. $z_2$ is chosen as a function of average coating level, but in such a way that $\theta(y)$ and y can achieve a one-to-one mapping relationship. $z_1$ and $Z_2$ are chosen as following:

$$z_1 = \begin{bmatrix} \bar{y}_{I_1} \\ \bar{y}_{I_2} \\ \vdots \\ \bar{y}_{I_K} \end{bmatrix},\ z_2 = |z_1 - y^*| = \begin{bmatrix} |\bar{y}_{I_1} - y^*| \\ |\bar{y}_{I_2} - y^*| \\ \vdots \\ |\bar{y}_{I_K} - y^*| \end{bmatrix},\ y^* = \frac{\max(\bar{y}) + \min(\bar{y})}{2}$$

For each column of the matrix $\Gamma$, the covariance computation is applied.

$$cov_1 = [cov_1(B_1) cov_1(B_2) \ldots cov_1(B_M)],\ \text{where } cov_1(B_i)=cov[P(B_i), z_1]$$

$$cov_2 = [cov_2(B_1) cov_2(B_2) \ldots cov_2(B_M)],\ \text{where } cov_2(B_i)=cov[P(B_i), z_2]$$

An angle vector can be then computed:

$$\theta = [\arg\{cov_1(B_1), cov_2(B)\} \ldots \arg\{cov_1(B_M), cov_2(B_M)\}]$$

The histogram bins that have similar angle values can be combined into one class. Notice that the two covariance vectors and the angle vector all have the same dimension as the histogram, therefore they can be further shown as 256×256 images or plots as shown in the following examples.

Figure 9:
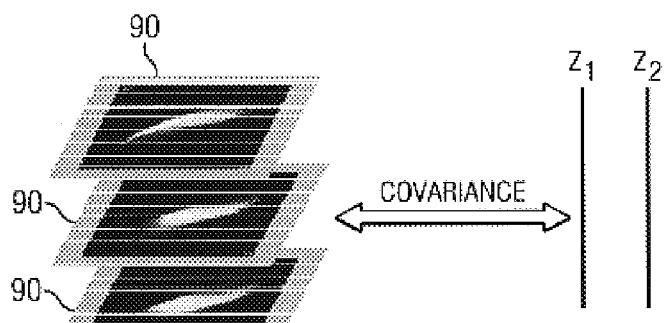
FIG. 9 represents the score plots of the imaged data stacked in order to determine the covariance according to one embodiment of the inventive method disclosed herein.
Figure 10A:
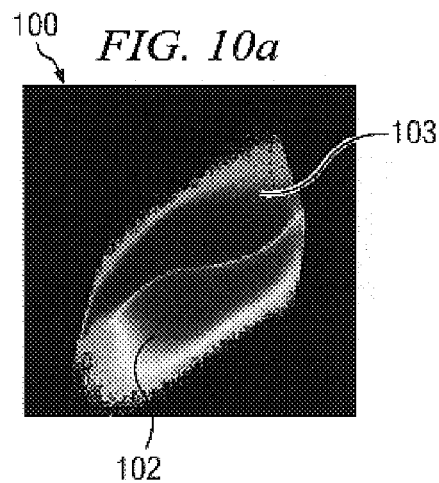
FIGS. 10a and 10b represent two colour coded graphical covariance plots obtained from the sample image training datasets and corresponding lab coating concentrations according to one embodiment of the inventive method disclosed herein.
Figure 10B:
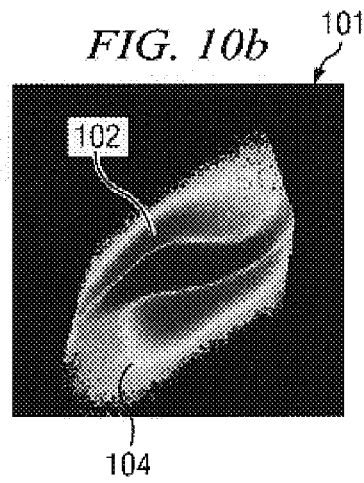
Figure 11:
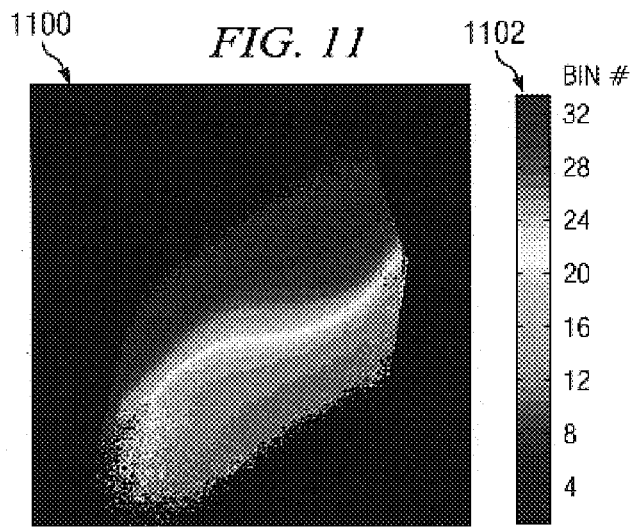
FIG. 11 is a graphical colour coded angle plot with 32 bins based on angle values which is used in the construction of a cumulative histogram based on the correlation of property segmentation in the imaged product according to one embodiment of the inventive method disclosed herein.

Method 6 is illustrated with FIGS. 9, 10 and 11. In FIG. 10, two covariance plots 100 and 101 are obtained by stacking up the 256×256 $t_1$-$t_2$ score plots 90 of the training set and computing the covariance of the number of pixels at each $t_1$-$t_2$ bin with the corresponding laboratory coating concentration as shown in FIG. 9. In the covariance plots of $z_1$ and $z_2$, FIG. 10-a and 10-b, respectively, warm colours (e.g. red, orange, yellow) 102 indicate positive covariance values and cold colours (e.g. green, blue, violet) 103 indicate negative covariance values. Darker shades 104 indicate large absolute covariance values as shown in FIG. 10-a and 10-b. From the two covariance plots (100, 101), an angle plot can be calculated as explained above.

Figure 12A:
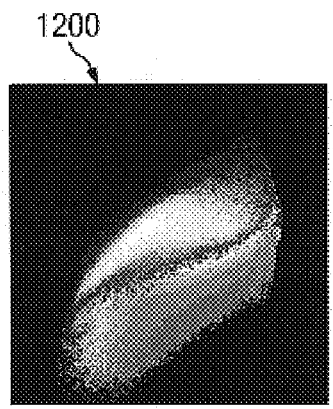
FIGS. 12a, 12b and 12c depict image score plots on top of a colour coded angle plot divided into 32 bins and for non-seasoned, low-seasoned and high-seasoned products, respectively, according to one embodiment of the inventive method disclosed herein.
Figure 12B:
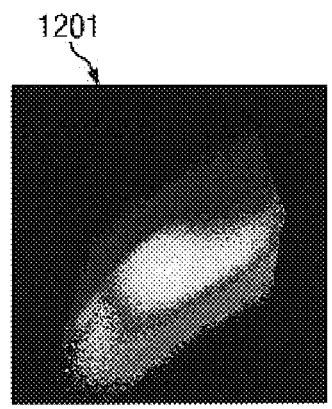
Figure 12C:
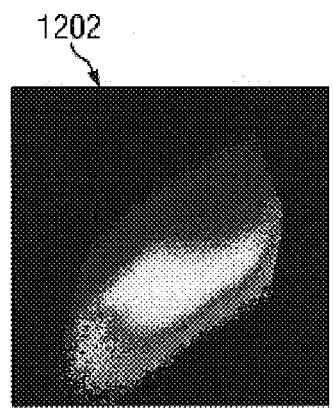
Figure 13A:
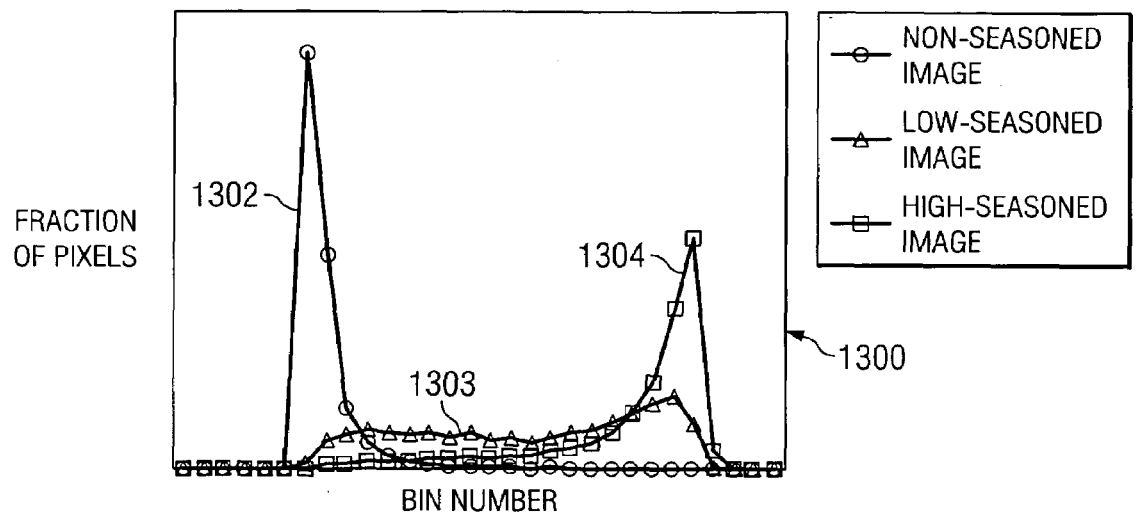
FIGS. 13a and 13b depict the resulting histogram and cumulative histogram, respectively, for the three product sample images score plots shown in FIGS. 12a, 12b and 12c according to one embodiment of the inventive method disclosed herein.
Figure 13B:
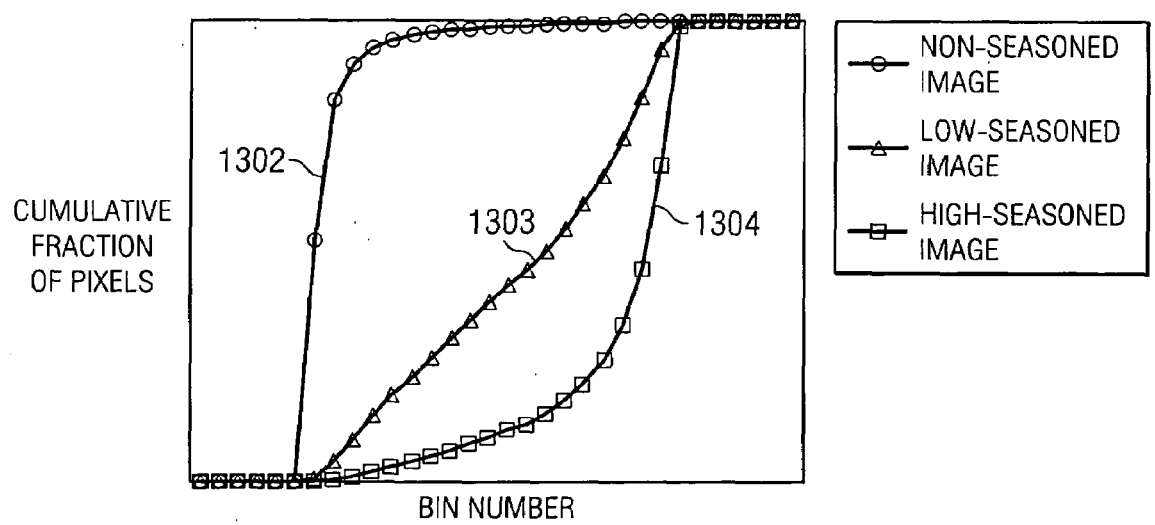

FIG. 11 depicts the colour-coded angle plot 1100 divided into 32 bins 1102 based on angle values. The score plot for any image can be superimposed on top of this plot and the number of pixels falling into each of these 32 angle bins recorded to form a one-dimensional histogram, as illustrated in FIG. 12-a, 12-b and 12-c for non-seasoned product 1200, low-seasoned product 1201 and high-seasoned product 1202, respectively. Resulting histogram and cumulative histogram for three sample images 1200, 1201, 1202 are shown in FIGS. 13-a and 13-b, respectively. Non-seasoned image 1302, low-seasoned image 1303, and high-seasoned image 1304, are shown plotted-as the bin number versus fraction of pixels in FIG. 13-a and bin number versus cumulative fraction of pixels in FIG. 13-b. It is noted that when building the regression model, only the cumulative histogram is used as the feature vector.

Foreground/Background Segmentation

Figure 15A:
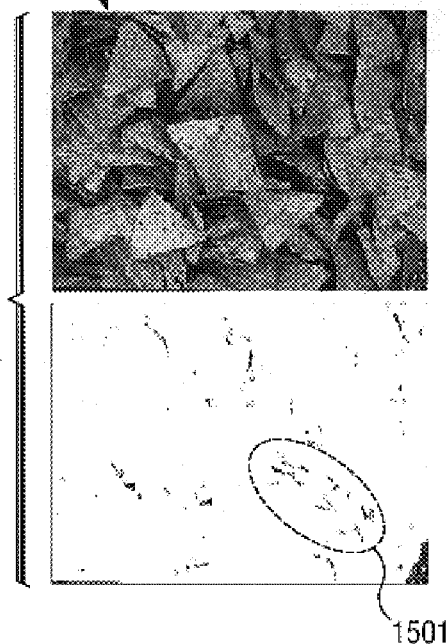
FIGS. 15a and 15b depict the background and foreign object pixels representing the conveyor belt and operator fingers, which are removed during the segmentation, step according to one embodiment of the inventive method disclosed herein.
Figure 15B:
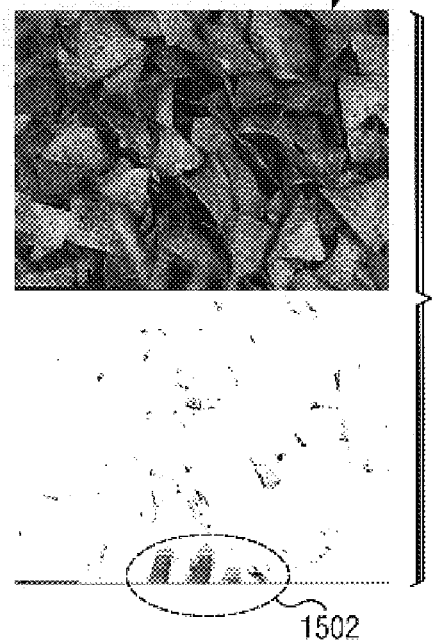

Segmentation is one important step that must be performed before doing feature extraction. Segmentation is the removal of pixels associated with background in the imaged product 1500. In the manufacturing of foodstuff, background arises from exposed areas of the table or pan on which the product is placed (off-line) or from exposed conveyor belt (on-line). FIG. 15-a depicts dark pixels 1501 that that represent the conveyor belt on which products 1500 are transported, while FIG. 15-b shows a technicians fingers 1502 resting on the conveyor belt along with product.

One approach based on spectral feature difference between the food product and the background uses product C above as the example. Since visual interpretation is not straightforward in three-dimensional colour space, a PCA is first performed to reduce the dimension. In this approach, PCA (without mean-center) loading vectors are computed using all the training images and a pure belt image or control process. As in traditional MIA techniques (Geladi et. al.), masks are chosen in the $t_1$-$t_2$ score space to separate different features. However, there are two reasons why masks cannot be chosen by traditional trial-and-error processes in MIA. First, in some images, belt pixels can easily be overlooked because of dark lighting conditions and misclassified as snack product pixels. Second, there are multiple images to be studied and manual trial-and-error approaches on each image are too time consuming. To solve these two problems, a new procedure for segmentation of the undesired image background is presented below.

Figure 17A:
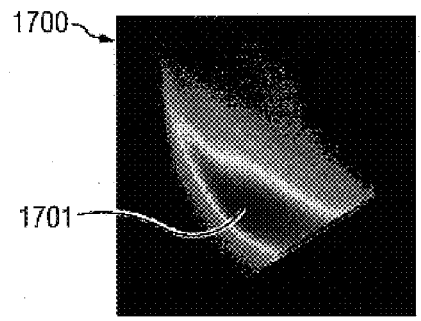
FIGS. 17a and 17b are graphical images depicting the calculated product masks according to one embodiment of the inventive method disclosed herein.
Figure 17B:
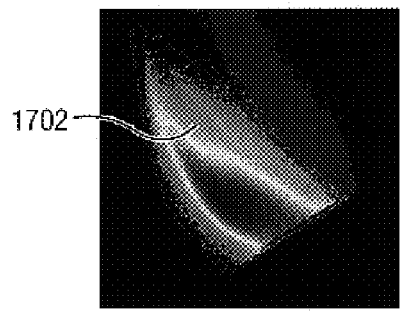

After a $t_1$-$t_2$ plane is obtained by PCA, $t_1$-$t_2$ score plots are stacked together for all training images; then two covariance plots $COV_3$ and $COV_4$ (with $z_1$ and $z_2$) can be computed as shown in method 6 discussed above. Since the background is independent of coatings concentration, histogram counts of a background colour should have low values in both covariance plots. Therefore, the absolute values of these two covariance plots are added together which, in turn, locates the pixels that have low total covariance values. Such a summation of the covariance plots is shown in FIG. 17-a where cold colours 1700 denote small covariance values and warm colours 1701 denote large covariance values. Moreover, the projection of the belt image into this $t_1$-$t_2$ space can also help to locate belt pixels (shown as medium gray pixels in FIG. 17-b). Then a product mask 1702, the area within outlined polygon in FIG. 17-b, can be created based on the covariance information and location of the belt image. For the new images, score pixels falling outside the product mask 1702 are considered as belonging to undesired background. The advantages of this method are manifested when calculating covariance plots that were considered in collecting information from all the training images. As such, this approach is not influenced by dark lighting conditions that could influence human visual judgment. It is interesting to note that this technique is able to remove not only the expected background (e.g. conveyor belt 1501 in FIG. 15-a) but also the unexpected background (e.g. human fingers 1502 in FIG. 15-b).

Prediction of Coating Concentration

Once feature variables have been obtained by any of the six methods, one can build inferential models by regressing these feature variables with the observed laboratory coatings concentration for the training set. In the preferred embodiment of the invention, PLS regression is desired to perform the regression analysis. In all PLS models, the feature variables are mean-centered and scaled to unit-variance. Transformations are used for the overall features (methods 1 and 2) to correct the nonlinearity. For the average colour features, a logarithmic transformation is used:

$$x_l' = \log(x_l), l = R, G, B$$

Since the loading values have the range between 0 and 1, a logistic transformation is used for the first loading vector features (method 2):

$$x_l' = \log\left(\frac{x_l}{1 - x_l}\right), l = R, G, B$$

Figure 14:
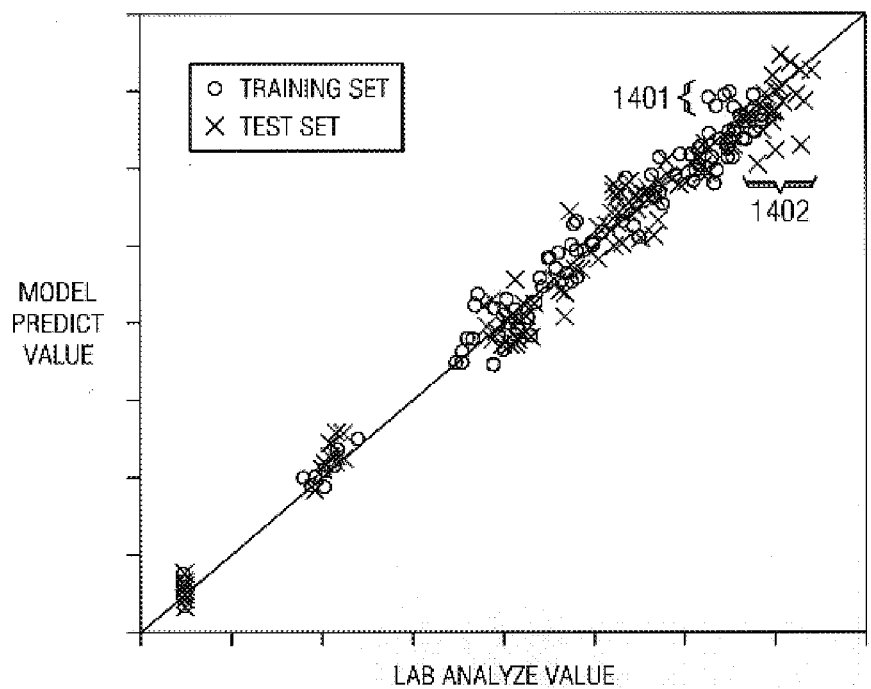
FIG. 14 is a graphical representation of the model predicted coating concentration versus laboratory analysis of the coating concentration on the food product training dataset and test dataset sampled and modeled according to one embodiment of the inventive method disclosed herein.

The performance of the PLS models is depicted in FIG. 14 and Table 2.

FIG. 14 plots the predicted average coating level versus laboratory analysis data for example product C using method 6 with training dataset data points 1401 and test dataset data points 1402. Similar plots can be obtained by using other methods or for other products. One can see that both the fit of the training dataset and the prediction of the test dataset are excellent.

Test results using all 6 feature extraction methods for Products A, B and C for both the training and testing image sets are shown in Tables 2-a, b, c below. In these tables, the original number of feature variables, the number of components used in PLS regression, the sum of square prediction error (SSE) and R-square statistic (the ratio of the regression sum of squares to the total sum of squares) are given. From the results, it is clear that each method works well and all have almost the same performance in all the cases. Moreover, it seems that the simple overall feature variable methods (methods 1 and 2) perform as well as the more complex distribution feature models (methods 3,4,5, and 6).

TABLE 2

Model Prediction Results

| | | Feature variable # | Latent variable # | Variance Analysis | |
|---|---|---|---|---|---|
| | | | | $SS_E$ | $R^2 = 1 - SS_E/SS_T$ |
| (a) Product A; $SS_T$ = 377.44(Training set); $SS_T$ = 385.13(Test set) | | | | | |
| Model 1 | Training set | 3 | 2 | 1.13 | 0.997 |
| | Test set | | | 1.60 | 0.996 |
| Model 2 | Training set | 3 | 2 | 2.25 | 0.994 |
| | Test set | | | 1.59 | 0.996 |
| Model 3 | Training set | 424 | 3 | 1.59 | 0.996 |
| | Test set | | | 3.60 | 0.991 |
| Model 4 | Training set | 32 | 3 | 0.95 | 0.997 |
| | Test set | | | 1.83 | 0.995 |
| Model 5 | Training set | 25 | 3 | 1.34 | 0.996 |
| | Test set | | | 1.18 | 0.997 |
| Model 6 | Training set | 19 | 2 | 0.74 | 0.998 |
| | Test set | | | 0.89 | 0.998 |
| (b) Product B; $SS_T$ = 869.83 (Training set); $SS_T$ = 845.41(Test set) | | | | | |
| Model 1 | Training set | 3 | 2 | 7.96 | 0.991 |
| | Test set | | | 8.64 | 0.990 |
| Model 2 | Training set | 3 | 2 | 4.58 | 0.995 |
| | Test set | | | 5.42 | 0.994 |
| Model 3 | Training set | 329 | 5 | 2.21 | 0.997 |
| | Test set | | | 5.13 | 0.994 |
| Model 4 | Training set | 32 | 3 | 3.58 | 0.996 |
| | Test set | | | 7.14 | 0.992 |
| Model 5 | Training set | 24 | 2 | 5.11 | 0.994 |
| | Test set | | | 8.72 | 0.990 |
| Model 6 | Training set | 18 | 2 | 5.82 | 0.993 |
| | Test set | | | 5.83 | 0.993 |
| (c) Product C; $SS_T$ = 817.19 (Training set); $SS_T$ = 751.63(Test set) | | | | | |
| Model 1 | Training set | 3 | 3 | 19.81 | 0.976 |
| | Test set | | | 13.12 | 0.983 |
| Model 2 | Training set | 3 | 2 | 20.09 | 0.975 |
| | Test set | | | 14.50 | 0.981 |
| Model 3 | Training set | 427 | 3 | 12.67 | 0.984 |
| | Test set | | | 18.56 | 0.975 |
| Model 4 | Training set | 32 | 3 | 17.75 | 0.978 |
| | Test set | | | 17.49 | 0.977 |
| Model 5 | Training set | 15 | 3 | 16.29 | 0.980 |
| | Test set | | | 13.66 | 0.982 |
| Model 6 | Training set | 19 | 2 | 20.56 | 0.975 |
| | Test set | | | 13.87 | 0.982 |

Figure 18A:
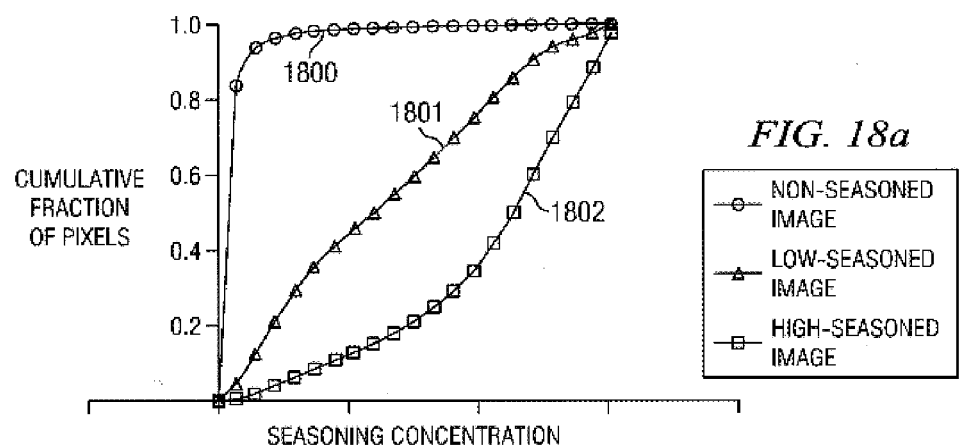
FIGS. 18a and 18b are graphical representations of the re-sampled and smoothed cumulative seasoning concentrations, respectively, for non-seasoned, low-seasoned, and high-seasoned products obtained by utilization of method 6 according to one embodiment of the inventive method disclosed herein.
Figure 18B:
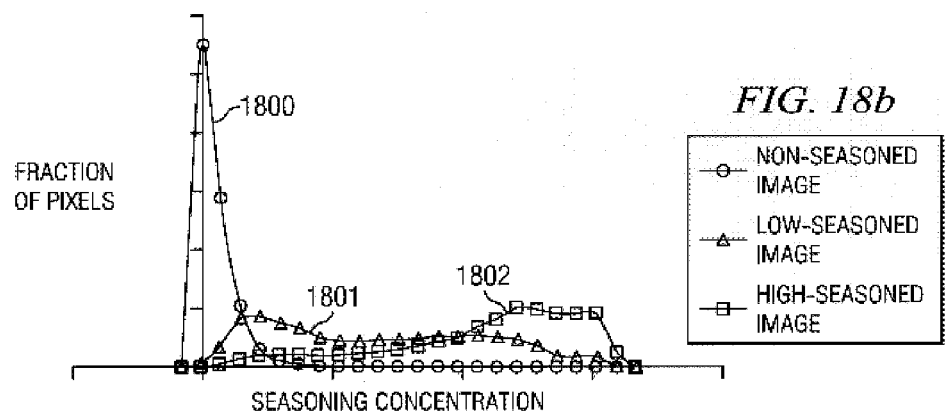

An estimation of the coating concentration can now be obtained directly, in this example by using method 6, by combining the cumulative angle histogram shown in FIG. 13-b and the estimated coating concentration for each bin shown in FIGS. 16-b, 16-c and 16-d. The resulting 32 bin cumulative coating distribution is then equally resampled and smoothed by a central moving-average smoother as shown in FIG. 18-a for the three sample images of product C, non-seasoned product 1800, low-seasoned product 1801 and high-seasoned product 1803 as referenced in Table 1. From these operations, the coating distribution is obtained as shown in FIG. 18-b.

Figure 19:
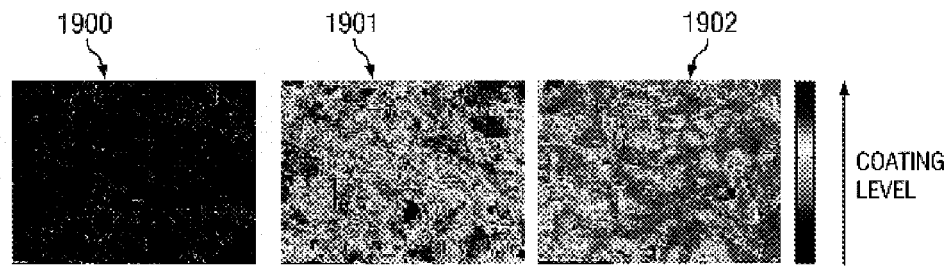
FIG. 19 is a colour-coded graphic display of the showing the calculated seasoning concentration on food products according to one embodiment of the inventive method disclosed herein.
Figure 20:
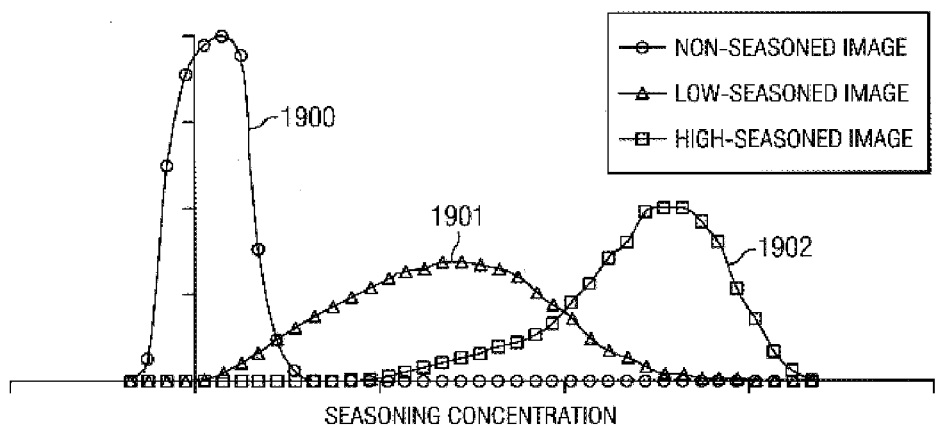
FIG. 20 is a graphical representation of the resulting coating distribution for the three sample images of product C using the small window strategy according to one embodiment of the inventive method disclosed herein.

Since method 6 can predict the coating concentration for each pixel, a colour-coded image can be generated on the coating concentration of each pixel for graphical display. FIG. 19 shows the colour-coded sample images for the product C samples. Image 1900 represents under-seasoned product, image 1901 represents moderately seasoned product and image 1902 represents highly seasoned product. These graphical display images are excellent for a quality control observer to visually monitor and control the manufacturing processes. FIG. 20 is a graph representation depicting the resulting seasoning concentrations for imaged product in FIG. 19 for non-seasoned product 1900, low-seasoned product 1901 and high seasoned product 1902.

Small Window Strategy

An alternative method of estimating the coating coverage distribution can be obtained by using larger areas of the imaged product, which is referred to as "small window" strategy. In this regime, each image is divided into many small windows and the coating concentration can be obtained by calculating average coating concentration for each window. Method 6 is preferred for small window prediction as it is the only method disclosed herein which is not image-size sensitive. In small window strategy, it is important to choose a proper window size. If this window size is too large, the spatial distribution information may be lost. On the other hand, if the window size is too small, the computation time may increase and the variance of the estimates will increase. An example of the small window procedure is discussed below.

Figure 21A:
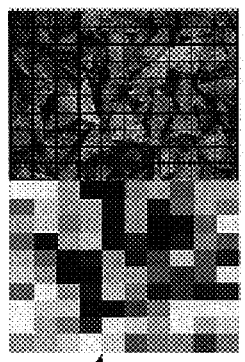
FIGS. 21a, 21b, and 21c represent the different divisions of product images in colour for a 10×10, 20×20 and 32×32 small window size calculation according to one embodiment of the inventive method disclosed herein.
Figure 21B:
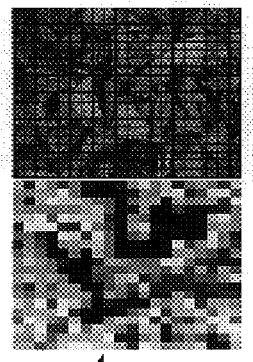
Figure 21C:
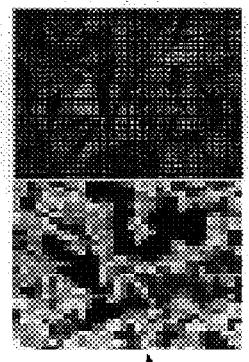
Figure 22:
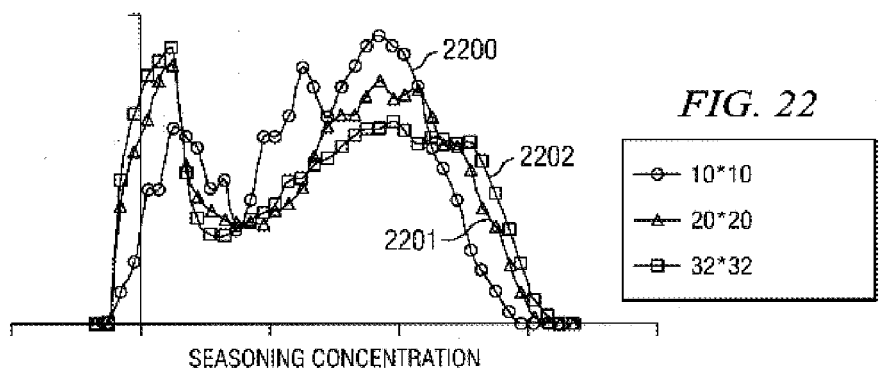
FIG. 22 is a graphical representation of the coating distribution obtained by using the 10×10, 20×20 and 32×32 small window sizes according to one embodiment of the inventive method disclosed herein.
Figures 23, 24:
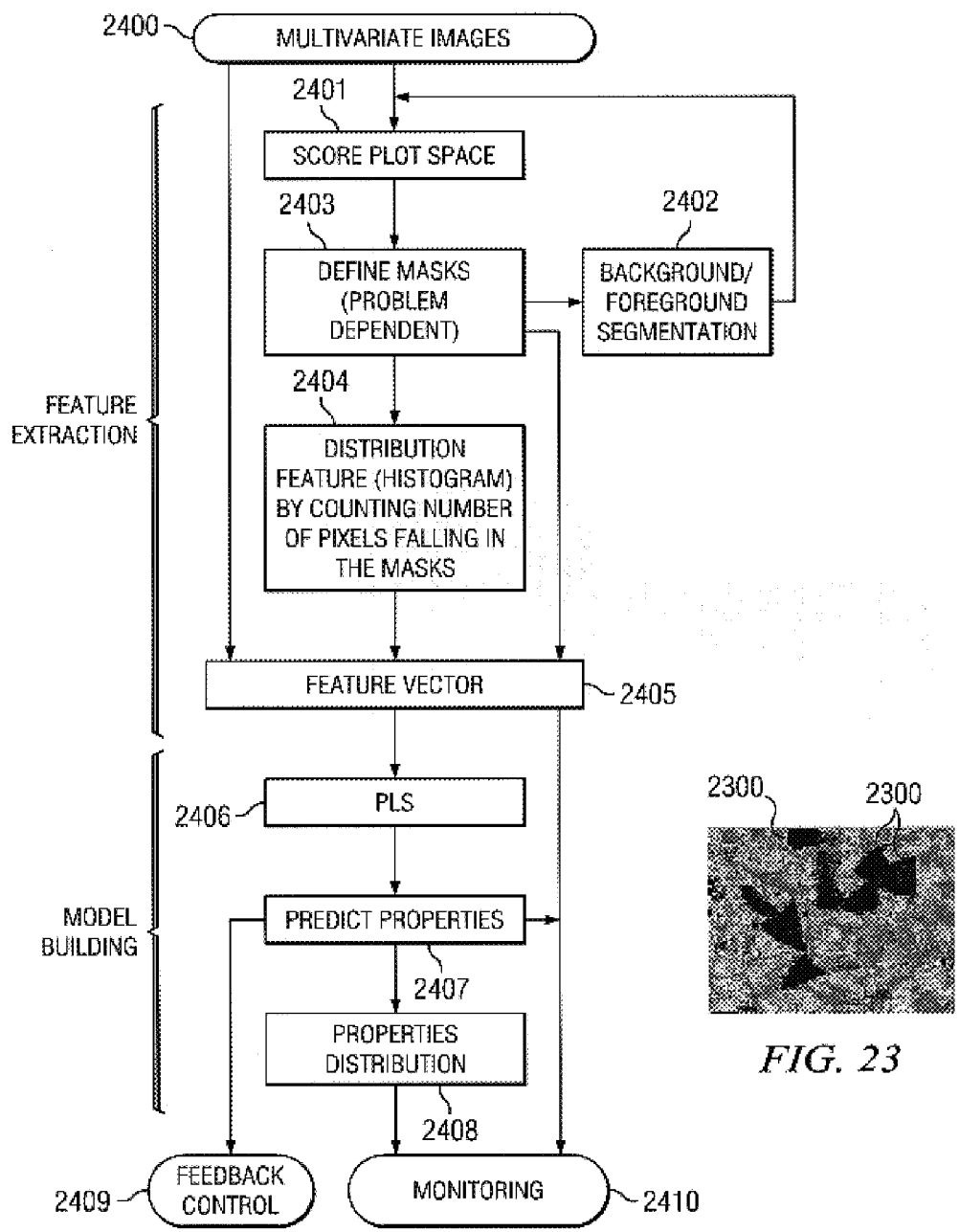
FIG. 23 is a colour-coded product image demonstrating the coated and non-coated seasoning portions on the food product according to one embodiment of the inventive method disclosed herein.
FIG. 24 is a flow chart depiction of the implementation of the product feature determination method disclosed herein.

An image with two mixed products (non-seasoned and high-seasoned products) is used to demonstrate the effect of different image window sizes. The product image is divided into 10×10, 20×20 and 32×32 windows (2100, 2101, and 2102, respectively) as shown in FIGS. 21a, 21b, and 21c, respectively. The estimated local coating concentration is shown by colour-coded images (the same colour map is used as in FIG. 19). The resulting coating distribution estimates are shown in FIG. 22 where 2200, 2201, and 2202 correspond to 2100, 2101, and 2102, respectively. When using 10×10 windows 2100, the two maxima are not as clear as the maxima found in using 20×20 windows 2101 and 32×32 windows 2102. The difference between the 20×20 and 32×32 samples 2101, 2102 is small. Since a 20×20 window 2101 can capture an adequate amount of coating distribution features, it can be chosen as a minimal practical window size for the application of the small window strategy. FIG. 23 is a pixel-by-pixel representation of a colour-coded image from using of small window strategy. Referring to the images in FIG. 19, the image in FIG. 23, generated by using the small window strategy, more clearly identifies the location and shape of non-coated product 2300.

Turning now to FIG. 24, a flow chart depicting one embodiment of the method disclosed herein is shown as utilized in the quality monitoring and control of foodstuff manufacturing. The method may be initially divided into two phases for identification purposes: (1) the feature extraction phase and (2) the model-building phase. In the preferred embodiment, the feature extraction phase occurs initially with the acquisition of multivariate images acquired by digital imaging equipment placed in an appropriate position in the on-line manufacturing environment (Step 2400). Next, a score plot space is acquired and an appropriate mask definition is developed (Step 2401) during background/foreground segmentation (Step 2402). After the appropriate mask is calculated (Step 2403), a histogram is created for the desired product feature (e.g. seasoning concentration) by implementing the feature extraction by method 6 discussed herein (Step 2404) and the feature vector is calculated (Step 2405).

The model building phase then begins with the implementation of a PLS regression applied to the calculated feature variables, the ones described by the feature vector, and the quality or control variables as defined by the training set test samples analyzed in the laboratory (Step 2406). The extracted feature, in this example the seasoning concentration on the foodstuff, is then predicted (Step 2407) and a property distribution may be constructed showing the predicted seasoning distribution on the on-line sample (Step 2408) or presenting an estimate of the spatial variance of the coating concentration. The calculated coating concentration is then supplied to a feedback control device (Step 2409) and/or a monitoring array (Step 2410) which control the operation of the on-line environment and can be instructed to take appropriate action in the event a process or control function is required. In an alternative embodiment, the distribution step (Step 2406) may be omitted to streamline the submission of acceptable data to monitor and control operations.

Sample results which were observed in utilizing the methods discussed in the example above are set forth in the following discussion and referenced figures for snack food coating concentration and coverage in an on-line environment. FIG. 25a and FIG. 25b depict initial data collected from the imaging system. Light gray lines 2500 show the raw coatings predictions. In this example, frequent grab samples were taken every 5 minutes from the conveyor and analyzed thereafter in the laboratory. The analytical results of the grab samples are shown as black circles 2501 in FIG. 25a. For each laboratory measurement, a X-error bar 2502 and a Y-error bar 2503 are also depicted. The Y-error bar 2503 indicates the approximate laboratory measurement error; the value is ±10.5 in FIG. 25a. The X-error bar 2502 indicates the possible sample time mismatch between taking the digital images of product moving on the conveyor line and manually grabbing the product samples for laboratory analysis. In this example, the error is estimated as ±1 minute.

One can see that the predicted coatings concentrations from the images match up well with the laboratory analysis. However, the image predictions reveal a clear saw-tooth behavior in the concentration that is not evident only from the lab data even during this fast sampling program. The coatings hopper refilling operations in the process explained this unexpected result. The lower plot 2504 in FIG. 25b depicts the signal 2505 of the hopper motor of the tumbler refilling system over a specified time interval. As the level of the coatings powder in the feed tumbler falls to a certain level, the motor is activated to refill the tumbler. The level of food coating inside the tumbler then increases rapidly. Clearly, FIG. 25a and FIG. 25b reveal that the discharge rate of food coating from the hopper to the coating tumbler is a strong function of the coatings level in the hopper.

Open Loop Results for Product A

Figure 26A:
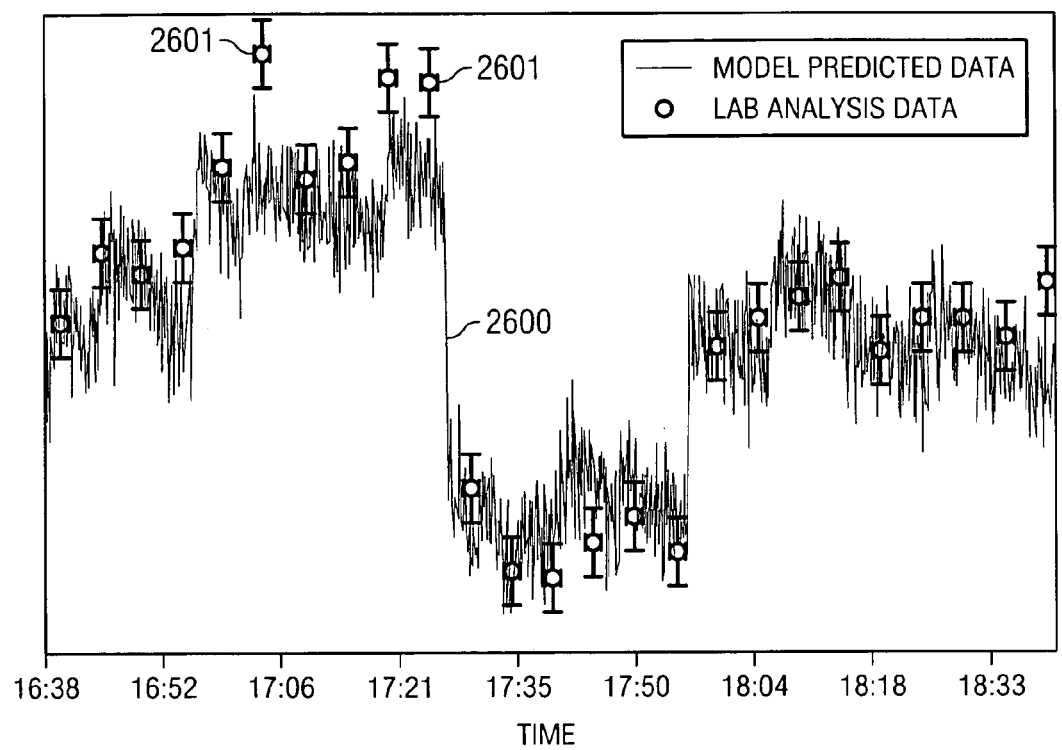
FIGS. 26a and 26b are depictions of the open-loop response of the seasoning level caused by changing seasoning level bias according to one embodiment of the inventive method disclosed herein.
Figure 26B:
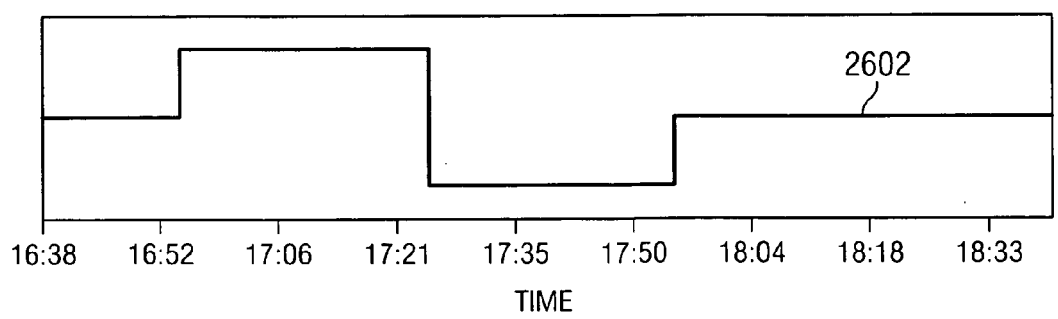

In FIG. 26a and FIG. 26b, the open-loop response of food product coating level caused by changing the coating level bias (manipulated variable) is shown. The prediction 2600 and laboratory analysis 2601 coating levels are shown in the upper plot FIG. 26a and, in the lower plot FIG. 26b, the coating level bias signal 2602 is shown. Again, it is observed that the predictions from the image analysis and the laboratory measurements are consistent. The predicted data shows a clear quick response to each coating level bias change.

On-Line Monitoring Sample Results for Products A and B

Figure 27:
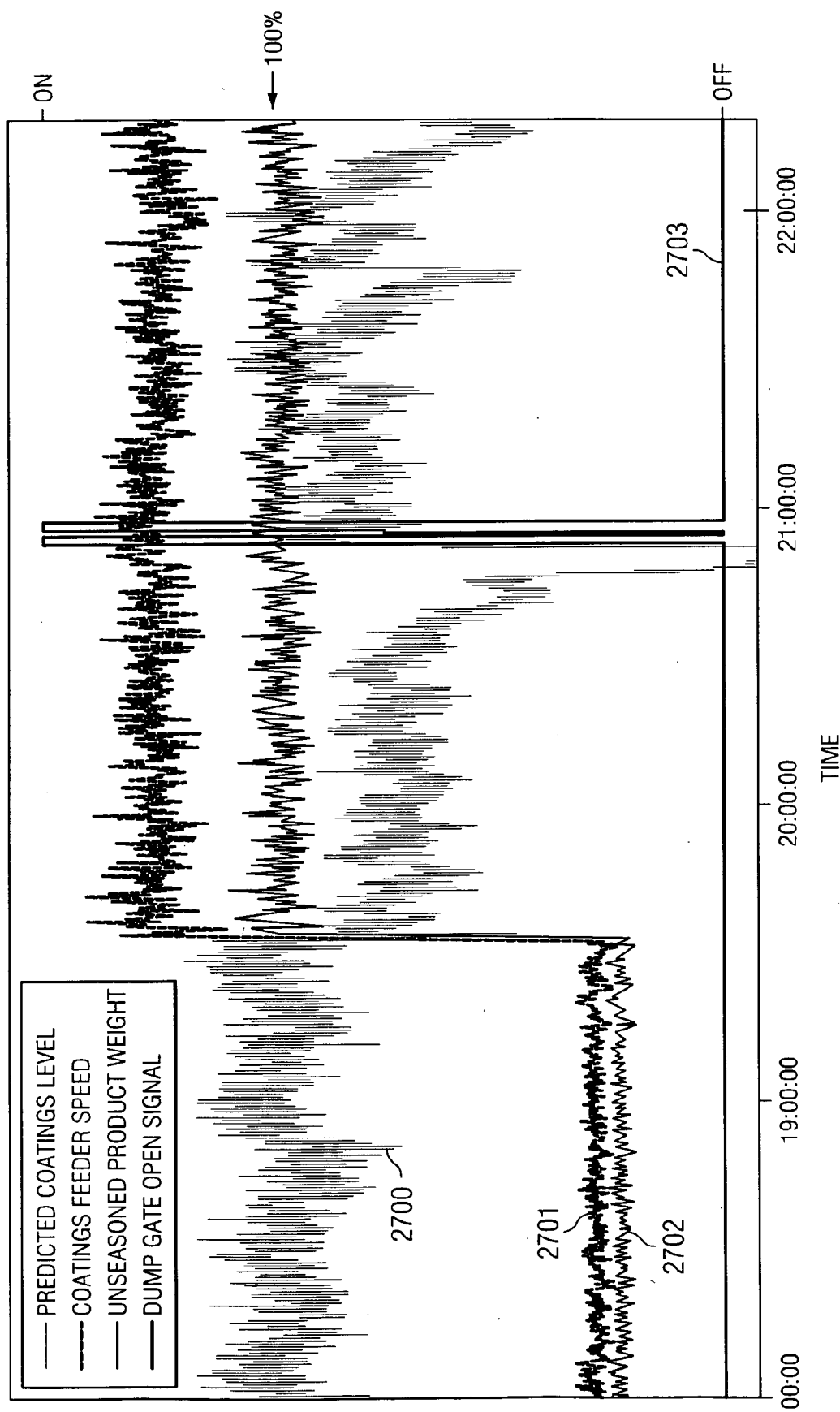
FIG. 27 represents a graphical depiction of the predicted seasoning level, observed unseasoned product weight, the seasoning feeder speed and signal of the dump gate to divert inferior product for product A according to one embodiment of the inventive method disclosed herein.

FIG. 27 depicts a single, four-hour on-line monitoring period for product A. Line 2700 indicates the predicted coatings level, line 2701 represents the unseasoned product weight, line 2702 indicates the coating feeder speed and line 2703 indicates the signal of the coating dump gate. During the time period, at about time 19:35, the feed rate of the non-seasoned product to the tumbler suddenly increased and as the result of ratio control, the coating feeder speed also increased. However, the coating feeder speed was limited by its maximum capacity and could not feed coatings fast enough to keep the desired ratio to the unseasoned product. Therefore, the coating level on product was observed to decrease from the desired value. Another concern was identified at time period starting at about time 20:40 where the coating level suddenly started to continuously decrease. This occurred because the coating hopper was not set to automatic refill mode and was therefore being depleted of coating. The result was that eventually no coating was being fed to the tumbler and the product dump gate had to open to remove the unseasoned products from the belt. It should be pointed out that by looking only at process data (non-seasoned product weight and coatings feeder speed) this fault was not detectable.

Figure 28:
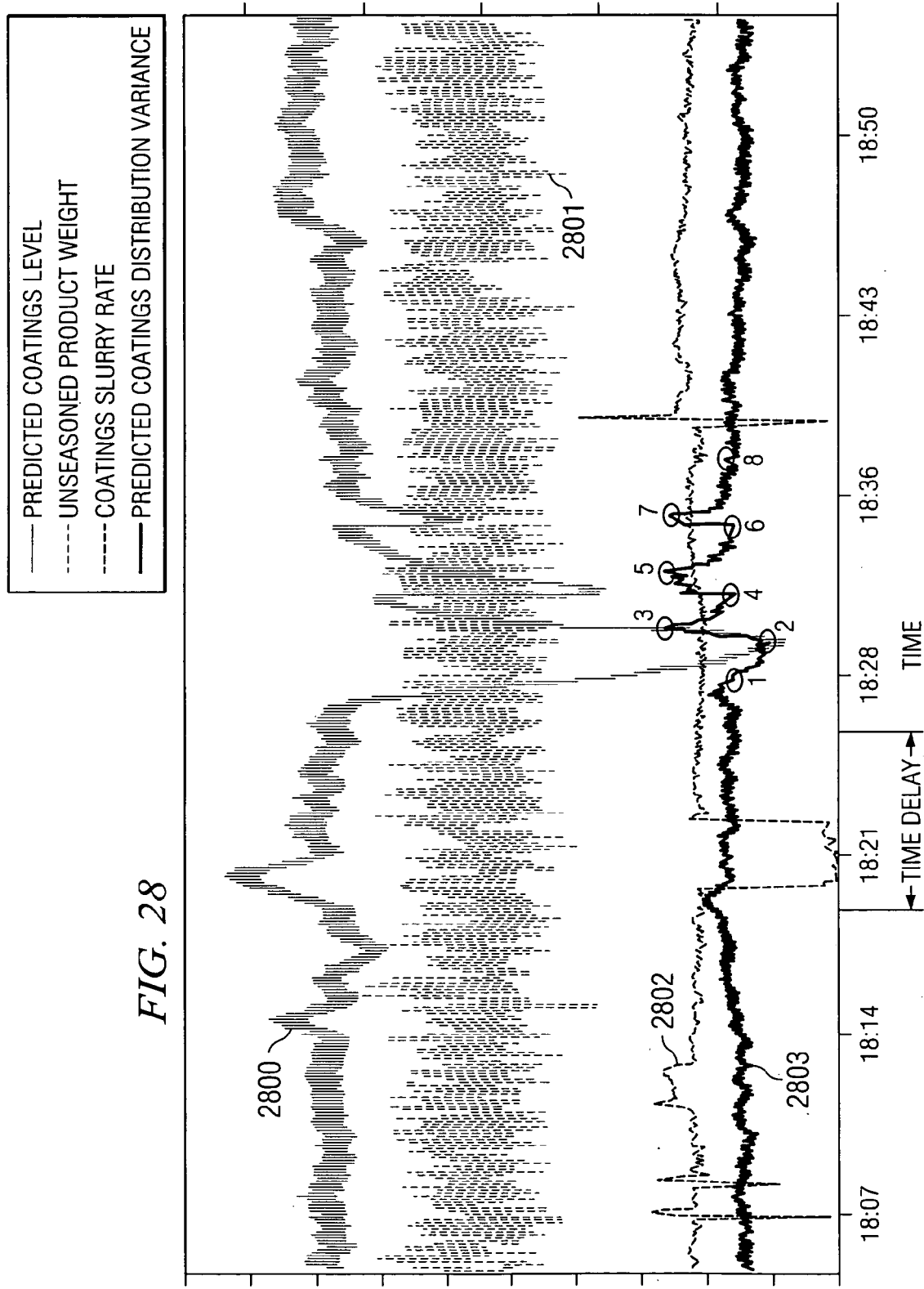
FIG. 28 is a graphical depiction of the predicted seasoning level, observed unseasoned product weight, the seasoning slurry feed rate, and the predicted seasoning distribution variance for product B according to one embodiment of the inventive method disclosed herein.

FIG. 28 shows one example of on-line monitoring for product B. In FIG. 28, line 2800 represents the predicted coating level, line 2801 represents the unseasoned product weight, line 2802 represents the coatings slurry feed rate and line 2803 in the lower portion of the graph represents the predicted coatings distribution variance. The variance of the coatings distribution was calculated from the histogram of the coatings concentrations obtained by applying the small window strategy outlined previously herein.

During this approximate 1 hour period of time, there was no large variation in the feed-rate of unseasoned product. However, it was observed that between time 18:19 and 18:23, the coating slurry feed-rate suddenly dropped to zero. The effect of this disturbance on the seasoned product appeared after about 8 minutes of time delay. At roughly 18:27, both the predicted coatings level and the coatings distribution variance began to show large variation.

To understand further what happened in the process during that time period, FIGS. 29a through 29h show eight product images (2900 through 2907), corresponding to the eight points 1-8 in FIG. 28. Because the coating slurry rate dropped to zero, unseasoned product was fed to the system during this period. This unseasoned product was mixed with seasoned product in the tumbler leading to a mixture of products as shown in the images in FIGS. 29a through 29h. The variance of the coatings distribution first decreased, visible as unseasoned product in one image 2901 in FIG. 29b, and then increased when there was a mixture of the two products, as shown in subsequent images 2902 and 2903 in FIGS. 29c and 29d, respectively. The coating distribution plot, consisting of data points 3000 in FIG. 30 corresponding to image 2904 in FIG. 29e, is estimated from the small window strategy and shows a bimodal distribution as expected.

Closed Loop Control Results

Figure 31:
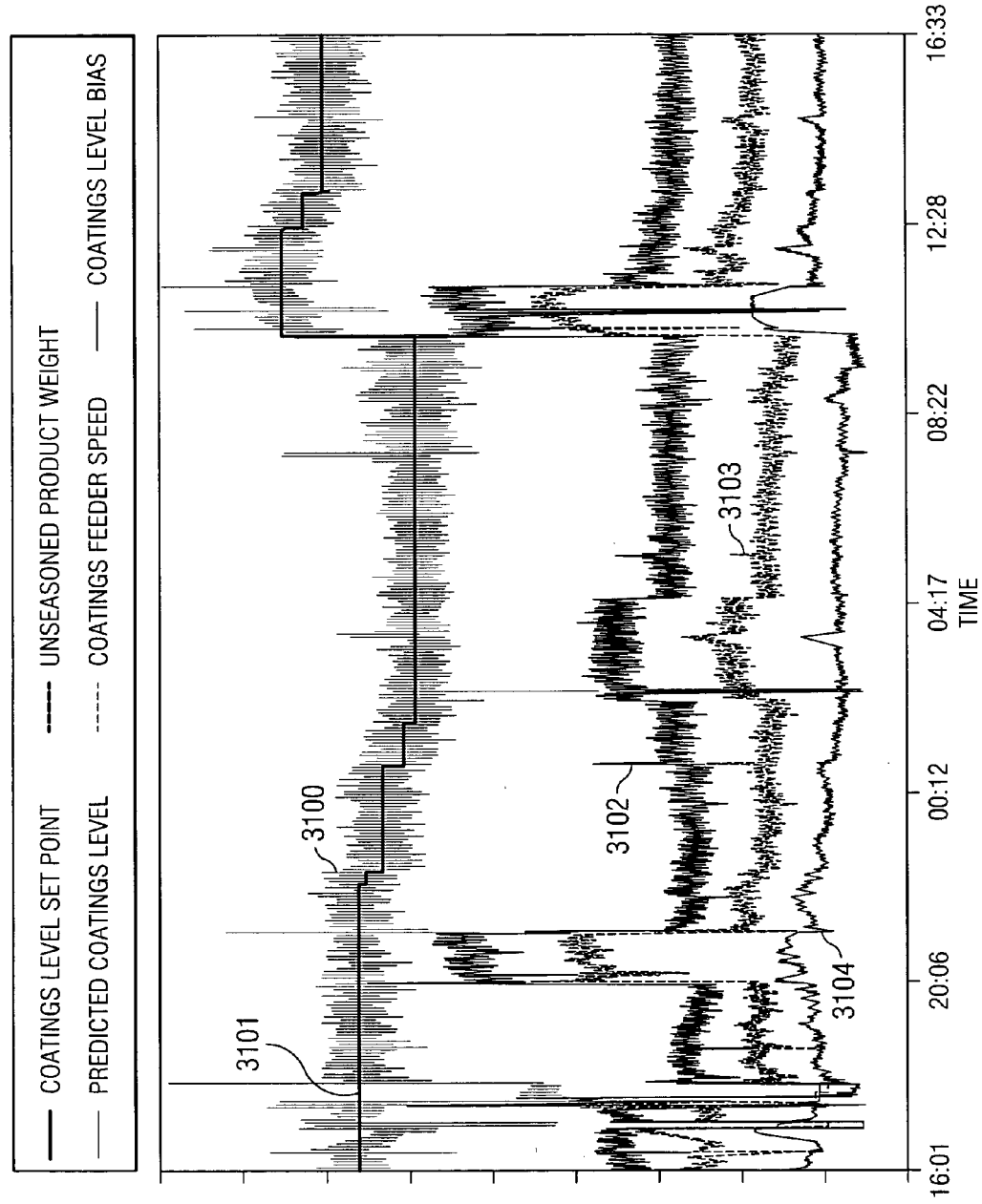
FIG. 31 is a graphical depiction of the seasoning level set point, the predicted seasoning level, the unseasoned product weight and seasoning feeder speed according to one embodiment of the inventive method disclosed herein.

Finally, operating data under closed-loop control covering a period of 24 hours is shown in FIG. 31 for product A. Line 3100 represents the predicted coating level. Line 3101 represents the coating level set point. Line 3104 and line 3103 represent the unseasoned product weight and coatings feeder speed respectively. Line 3102 indicates coatings level bias change, which is used as the manipulated variable. It is observed that the coating level successfully tracked the set point. Another point to note is that the saw-tooth effect of the coating feeder system that was apparent in FIGS. 25a, 25b, 26a, 26b and 27 is no longer as noticeable. This is due to an operational change introduced to eliminate this effect.

In particular, it will be understood that the source data may be an image captured in a range of predetermined wavelengths which is not limited to the visible spectrum. The images of the snack food could, for example, be captured in the near infra-red spectrum. For convenience, the current work is most easily carried out in the visible spectrum using three colour channels, red, blue and green. Using the visible spectrum may not be desirable or appropriate in other applications. In the preferred embodiment described above, the food is illuminated with visible light to obtain the image of a product of the process. In other processes, it may not be necessary to illuminate the object.

As described above, lighting variations may influence the overall feature variable values. Under ideal conditions, the product under inspection would remain at a fixed distance from the light-emitting source so as to provide a consistent light reflective surface with a consistent density of light over the surface area of the product. As the distance between the measured product and the light emitting sources changes, the density of light reflecting from the product changes. As the density of the reflected light changes, the feature variable values change. By moving the product to different distances from the light and camera and measuring the resultant change in the predicted feature values, then performing a regression method to correlate the feature value to distance between product and sensor, a model can be developed to predict changes in product feature values for changes in product bed depth when the camera and light source are stationary. Conversely, changes in feature values can be used to predict the bed depth of the product or change in distance of the product from the stationary sensor when all other process variables are held constant.

In a similar manner, the specific density or bulk density of a product can also have an effect on the measurement of a product feature that is dependent on these variables. The measurement of the amount by weight of coating on a product will be affected if the surface area does not change by the same amount as the weight of the product. Therefore, in measurement of surface area product features, the density of the product can be taken into account and modeled so that a prediction of feature concentration by weight or volume can be made. In addition, the specific density or bulk density of the product can be predicted using the measured surface feature coverage values, surface feature application rate, and weight of the base product.

Embodiment of Prediction of Organoleptic Properties

Along with predicting coatings concentrations (described above), the present invention, in one embodiment, provides a method and apparatus for objectively predicting organoleptic properties (e.g. texture, taste and sight) of food products. This invention is the first to successfully predict organoleptic properties using images.

Figure 52:
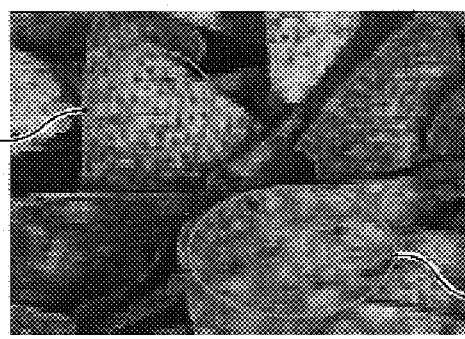
FIG. 52 is a colour image showing blisters and toast points on the surface of a snack product (chips) according to one embodiment of the invention disclosed herein.
Figure 53A:
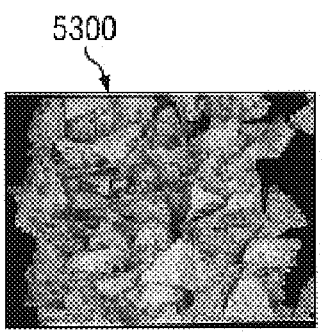
FIGS. 53a through 53d depict images of a snack product (chips) with two different levels of seasoning coating and with two different levels of blisters and toast points (organoleptic properties)
Figure 53B:
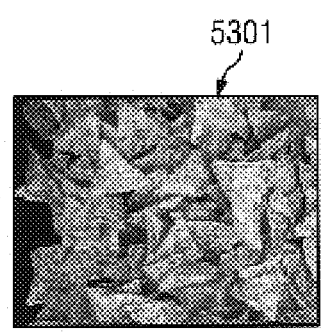
Figure 53C:
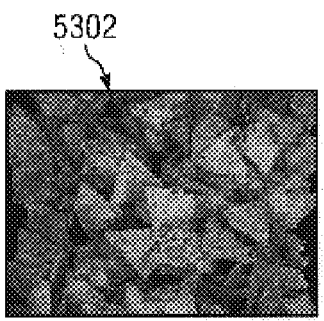
Figure 53D:
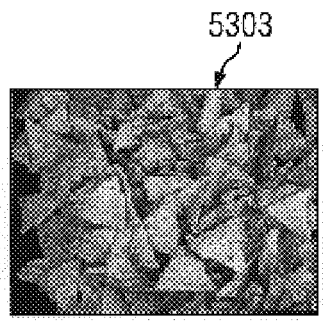
Figure 54A:
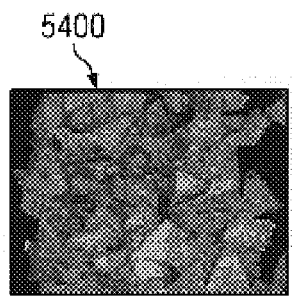
FIGS. 54a through 54d depict images of a snack product (chips) with two different levels of seasoning coating and with two different levels of blisters and toast points (organoleptic properties) where the coating information has been removed.
Figure 54B:
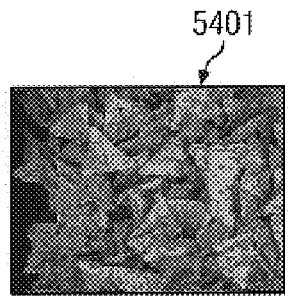
Figure 54C:
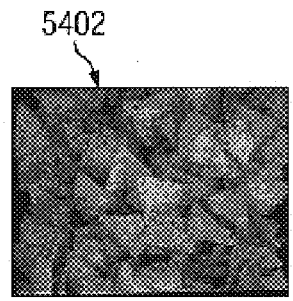
Figure 54D:
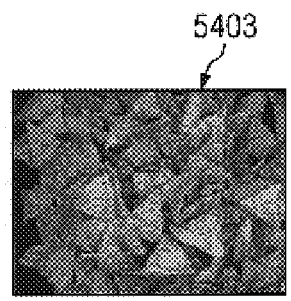
Figure 55A:
FIG. 55a through 55f depict sets of colour images of a flame of a steam boiler as an embodiment of the invention according to the inventive method disclosed herein at various conditions corresponding to those conditions associated with FIGS. 33a and 33b, and FIGS. 34a and 34b.
Figure 55B:
Figure 55C:
Figure 55D:
Figure 55E:
Figure 55F:
Figure 56A:
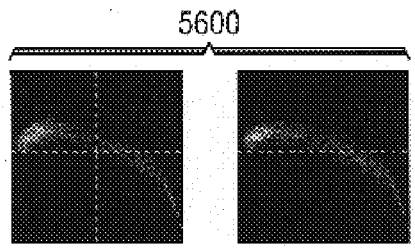
FIGS. 56a through 56f depict sets of colour score plots for the sample images depicted in FIG. 55.
Figure 56B:
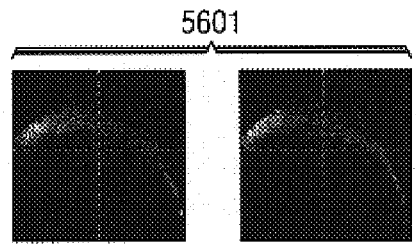
Figure 56C:
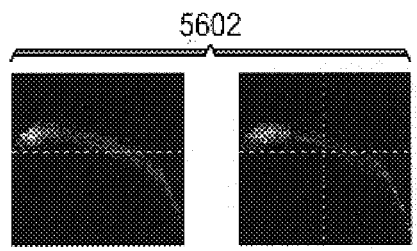
Figure 56D:
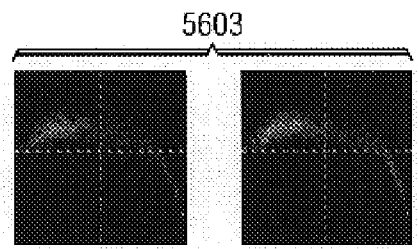
Figure 56E:
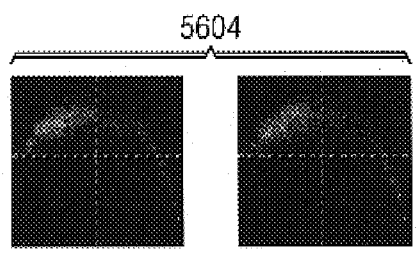
Figure 56F:
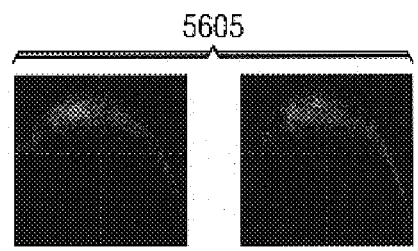
Figure 57A:
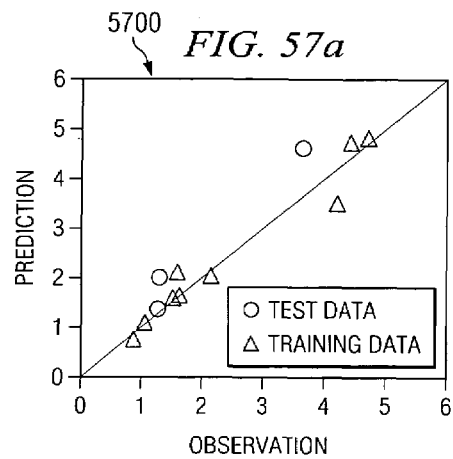
FIGS. 57a through 57d are plots of the prediction vs. observation; one plot representing blister level, toast point level, taste property, and peak break force, respectively.
Figure 57B:
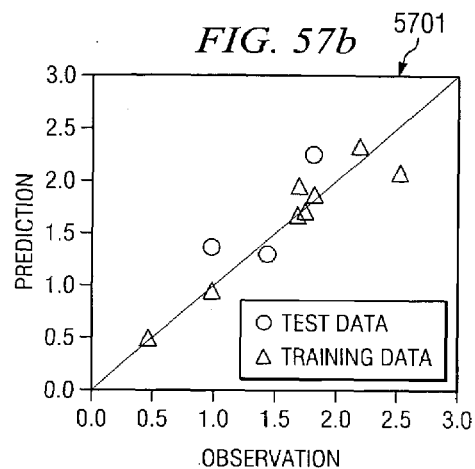
Figure 57C:
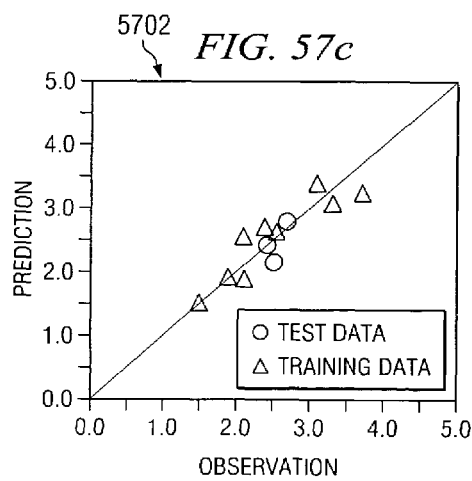
Figure 57D:
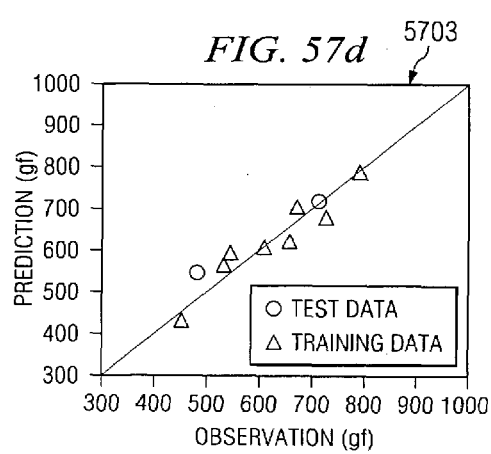

Examples of an organoleptic property of a snack food (e.g. chips) are the following: blister level, number of toast points, taste, texture, crispness, crunchiness and peak break force. Each property has its own scale of measurement. Blisters on chips are graded on a scale from 0 to 6 by comparing the chips with reference images or drawings. Level 0 represents chips with no blisters; level 6 represents chips containing a very large number of blisters. Level 3 is considered to be the optimal amount of blisters. Toast point level is graded on a scale from 0 to 4 by comparing chips with reference drawings or images. Level 0 represents no toast points on the chip and level 4 indicates a burnt chip. Level 2 is considered to be optimal. FIG. 52 illustrates toast points 5200 and blisters 5201.

Taste, as an organoleptic property (unrelated to coating level), is also measured by comparing a sample with reference chips. The taste of each sample chip is graded from 0 to 5. Level 0 indicates a dense chip and level 5 is a light, blistery chip. The ideal value of this taste property is 3. This measurement is obtained by having a person eat a reference chip and subsequently eat the sampled chip. Crispness, crunchiness and texture may be measured in a similar way.

To gather one dataset of organoleptic properties, humans sampled thirteen cells of food product; the data derived from the human testers were compared against the collected image data. The data are shown in Table 3. Each cell corresponds to a certain operation condition. Fifteen RGB colour images were also collected from each cell. These images are used as predictors in the model. Four sample images 5300-5303 are found in FIGS. 53*a* through 53*d*. Thirty chips, randomly selected from each cell, are used to measure the blister level and the toast point level. Another, randomly selected, ten and fifteen chips from each cell are used to measure the taste property and the peak break force, respectively. Average values of blister level, toast points, taste and peak break force for each cell are used as the response matrix Y as seen in Table 3. Table 3 reveals a high correlation between the Y variables. The chips having high levels of blisters and toast points, such as those in cell 6A in Table 3, also generally have high taste level and a large peak break force.

TABLE 3

| | Coating Level (1 = coated, | Average Organoleptic Properties Y | | | | | | | |
|---|---|---|---|---|---|---|---|---|---|
| | | Blister Level | | Toast Points | | Taste | | Peak Force (g) | |
| Cell Name | 0 = uncoated) | Mean | Std | Mean | Std | Mean | Std | Mean | Std |
| 1A | 0 | 0.87 | 0.57 | 0.97 | 0.52 | 1.5 | 0.71 | — | — |
| 1B | 0 | 1.3 | 0.53 | 0.98 | 0.69 | 2.5 | 0.97 | — | — |
| 2A | 1 | 1.07 | 0.65 | 0.45 | 0.51 | 2.1 | 0.57 | — | — |
| 2B | 1 | 1.27 | 0.43 | 1.42 | 0.63 | 2.4 | 0.52 | 480.9 | 112.6 |
| 2C | 0 | — | — | — | — | — | — | 451.3 | 103.2 |
| 3A | 0 | 1.63 | 0.85 | 1.38 | 0.64 | 2.1 | 0.74 | 530.9 | 105.8 |
| 3B | 0 | 1.52 | 0.52 | 1.65 | 0.44 | 1.9 | 0.74 | 606.7 | 142.7 |
| 4A | 1 | 1.62 | 0.54 | 1.68 | 0.70 | 2.4 | 0.46 | 542.7 | 121.8 |
| 4B | 1 | 2.15 | 0.87 | 1.72 | 0.67 | 2.55 | 0.69 | 655.4 | 176.1 |
| 5A | 0 | 4.73 | 1.44 | 1.80 | 0.34 | 3.1 | 1.10 | 786.1 | 150.6 |
| 5B | 0 | 3.64 | 1.40 | 1.80 | 0.85 | 2.7 | 1.27 | 709.3 | 98.5 |
| 6A | 1 | 4.22 | 1.58 | 2.50 | 0.63 | 3.3 | 1.16 | 720.8 | 166.6 |
| 6B | 1 | 4.43 | 1.69 | 2.17 | 0.82 | 3.7 | 1.06 | 668.2 | 158.7 |

Image Analysis

In order to detect organoleptic properties using the teachings of the present invention, it is necessary to remove the effect of any coating on the food product because any colour variation caused by a coating may influence the texture information. Here the interest is in the coating level of the snack food. A procedure based on PCA can be used to cancel the effect of the coating.

A mean-centered PCA technique is performed on several uncoated product images; background pixels are removed. In this embodiment, the first two components, $t_1$ and $t_2$, explain about 87.0% and 11.3% of the variation, respectively. Therefore, this $t_1$-$t_2$ lane captures most of the variation caused by changes in the imaging condition and is not influenced by the variation caused by the coating level. By projecting the pixels of the coated images onto this $t_1$-$t_2$ plane, the coating information is largely cancelled. FIG. 54 shows the reconstructed images (from the first two principal components, blister level and toast point level) for the 4 sample images shown in FIG. 53.

Organoleptic Information Extraction from Images

A series of nine Laplacian of Gaussian (LoG) spatial filters with different window sizes are applied to the first two score images to extract texture features. Laplacian filters are derivative filters used to find areas of rapid change or the edges in images. Since derivative filters are very sensitive to noise, it is common to smooth the image (e.g., using a Gaussian filter) before applying the Laplacian. This two-step process is called the Laplacian of Gaussian (LoG) operation. The 2D LoG function centered on zero with Gaussian standard deviation σ has the form:

$$\text{LoG}(x, y) = -\frac{1}{\pi\sigma^4}\left[1 - \frac{x^2+y^2}{2\sigma^2}\right]e^{\frac{x^2+y^2}{2\sigma^2}}$$

The Gaussian standard deviation is chosen as 0.5. The window sizes of the filters are chosen from four to twenty (even numbers). These parameters are chosen by trial-and-error. For each filtered image, a simple average value is computed. Therefore, a total of eighteen feature variables for each RGB image are generated, including the nine average filtered values for the first score image and the nine average filtered values for the second score image.

The organoleptic values of the samples can be predicted. Four PLS models are built to predict these organoleptic values, one for every organoleptic or Y property. An average feature vector is computed for each cell. This averaged feature vector, along with a dummy variable indicating whether the product in the image is coated, is used as a predictor. The dummy variable could be replaced with the predicted coating concentration in other embodiments.

Among the thirteen observations, each one corresponding to one of the thirteen cells, ten observations are used for training the models. FIGS. 57a through 57d shows the prediction vs. observation plots for each one of the Y variables: blister level, toast point level, taste property, and peak break force, respectively.

The root mean square errors for prediction (RMSEP) and the estimated standard deviation of measurement error from the test set are listed in Table 4 for the four Y variables. The RMSEP is estimated by assuming that the global texture property for each cell is constant and all the samples in each cell are treated as replicate points. Analysis error considered here involves both sampling errors and instrument measurement errors. To estimate these analysis errors, several groups of data points are used. Each group contains samples taken within a short period of time whose properties can be assumed to be constant within that period of time. Therefore, points within one group can be considered as replicate points. Consider K groups of data points and for a group k, the number of data points is $N_k$ (k=1,2,,K). $y_{ki}$ is the property of the i-th point in group k and $\bar{y}_k$ is the average property of group k. Then the lab analysis error, one standard deviation, is estimated as follows:

$$err = \sqrt{\frac{\sum_{k=1}^{K}\sum_{i=1}^{N_k}(y_{ki} - \bar{y}_k)^2}{\sum_{k=1}^{K}N_k - K}}$$

Relative errors for blister level are used because the standard deviation value for each cell increases as the average values of the blister level increases (see Table 3). The number of latent variables (LV) used is also shown in Table 4.

TABLE 4

Comparison of Prediction Errors of the Inferential Model and Analysis Measurement Error

| | Number of LV's | RMSEP for Test Set | Estimated Std Deviation of Measurement Error for Taking 1 Piece of Food Product |
|---|---|---|---|
| Blister Level* | 5 | 0.36 | 0.44 |
| Toast Point Level | 5 | 0.34 | 0.64 |
| Taste Property | 3 | 0.29 | 0.87 |
| Peak Break Force | 4 | 45.35 | 138.91 |

*For blister level, relative RMSEP and relative measurement error are computed.

Table 4 shows that the measurement error is larger than model prediction error for all 4 Y variables if only one piece of food product is measured. Taking more samples within a short time and using the average of the measurements of these samples can easily reduce the measurement error. However, since organoleptic properties of a food product are measured manually (a human has to grade the product by looking at it, eating it or taking it to the mechanical machine), the number of samples used for measuring the properties is proportional to the time and manpower required. Therefore, to set up a monitoring system for organoleptic properties at a moderate sampling time requires substantial manpower. On the other hand, by using an imaging system, once an imaging model has been trained, the predictions can be obtained very quickly with almost no extra cost, and the sampling rate can be increased as desired.

Using other physical process or product measurements may enhance the measurement of organoleptic properties. Physical process properties or measurements are not organoleptic properties. Product temperature, process temperature (e.g. fryer oil temperature), chip moisture content, chip oil content, chip weight per ten (the total weight of a sample of ten food products), tumbler speed, cooling air velocity, and dough moisture are just a few examples of physical process measurements that can be taken. These measurements can be combined with the information found in the images taken with the machine vision system described above resulting in a more accurate measurement or prediction of an organoleptic property. One or more physical process measurements may be so combined with the machine vision measurement.

The vision measurement system may also be used to predict other food product properties other than organoleptic properties. For example, the machine vision measurements may be used to measure physical product properties such as product moisture content, product oil content, chip weight per ten, dough moisture, and other product properties.

In addition to combining physical process measurements with the machine vision image data, acoustic measurements may be combined to enhance measurement of organoleptic properties. Acoustic data may be obtained from products by subjecting the products to an acoustic energy signal and subsequently capturing or measuring the resulting signal. Acoustic data from such a signal may be taken and regressed to correlate with one or more organoleptic properties. By combining acoustic measurements, physical process measurements and machine vision measurements, a novel system is provided to accurately measure and predict organoleptic properties. These measurement combinations for the first time fill a strong need in the processed food industry to measure product attributes in an on-line production environment.

Embodiment of Flame Analysis

Another exemplary alternative embodiment of the invention disclosed herein is described below with reference to a process in which a flame product characterizes the underlying process. Because the flame is luminous, no external source of lighting is required. It will also be understood that the radiation emanating from a flame will cover a wide range of wavelengths which are not limited to the visible spectrum.

In many industrial furnace and boiler systems, television systems have been installed. However, they are used mainly for live displays of the flames. Most of the time the only information the flame images provide is whether the flames are burning. Because combustion processes are highly turbulent, the flames appear in constant movement, and even the most experienced operator often finds it hard to determine the performance of the combustion.

In this situation, a monitoring system based on image analysis can become very helpful. In this alternative embodiment of the invention disclosed herein, an industrial steam boiler is observed. The fuels used for this boiler may be a waste liquid stream from other processes or may be natural gas. Therefore, the composition of the fuel is often variable. An analog colour camera is installed and the flames behavior is recorded onto several videotapes. A video card is used to convert the analog signals into digital images. Alternatively, a flame grabber may be used for on-line analog-digital conversation.

To analyze the colour images, a Multivariate Image Analysis (MIA) technique is used. Nine features are extracted from score plot space for each image. Moreover, multivariate statistical methods, such as Principal Component Analysis (PCA) and Partial Least Squares (PLS) may also be performed on the image features and the process measurements to help understand the relationship between the feature variables and the process variables.

System Setup

Figure 32:
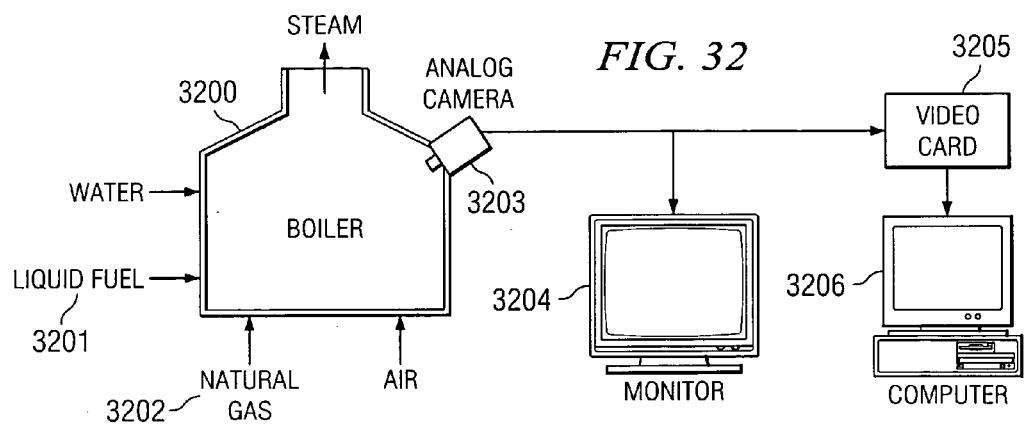
FIG. 32 is a schematic diagram depicting a flame analysis embodiment of the invention integrated into a steam boiler according to the inventive method disclosed herein.

A schematic diagram of one embodiment of a flame monitoring system is shown in FIG. 32. The steam boiler 3200 uses both the waste liquid streams 3201 from other processes and natural gas 3202 as fuels. Therefore, the compositions of the fuels often change dramatically. 20 An analog colour camera 3203 has been installed in the boiler 3200 and is connected to a monitor 3204 for displaying the live images. In this embodiment, the analog signals are recorded and converted into digital images by video card 3205 which are then analyzed by computer 3206 according to the methods disclosed herein. The resulting images are RGB colour images with a 120×160 pixel size. Considering the processing time, the imaging sample time is set as 1 frame per second.

Figure 33A:
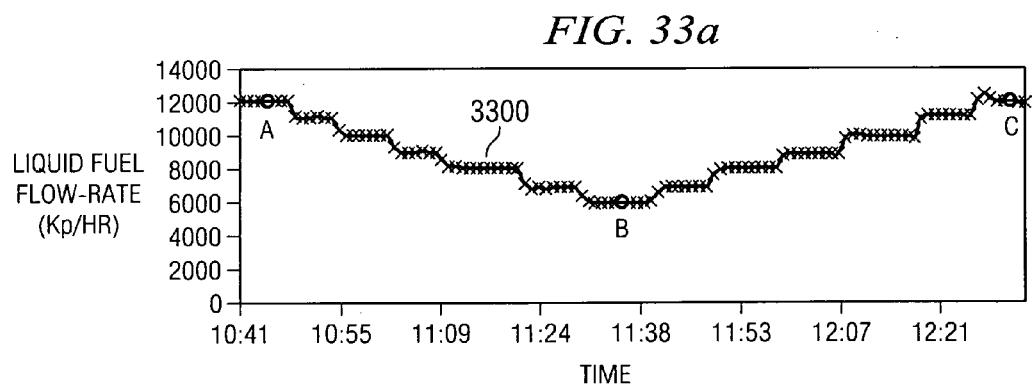
FIGS. 33a and 33b graphically depict the flow rate of liquid fuel (A) and steam flow rate over time for case I.
Figure 33B:
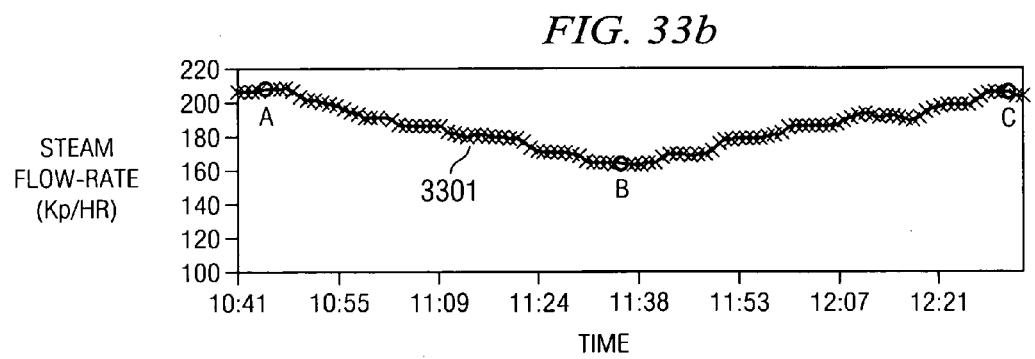

Two case studies are presented to exemplify the application of the invention. Case I is a 114 minute boiler process. In this period of time, a liquid fuel (A) is used. In the first half of this period of time, liquid fuel consumed in the flame decreases from 12,000 kilo pounds per hour (kp/hr) to 6,000 kp/hr; in the second half of the time period, liquid fuel increases back to 12,000 kp/hr. A data point line 3300 in FIG. 33a depicts this variable. The steam generated by the boiler followed the same trend as the fuel flow as shown by a data point line 3301 in FIG. 33b.

Figure 34A:
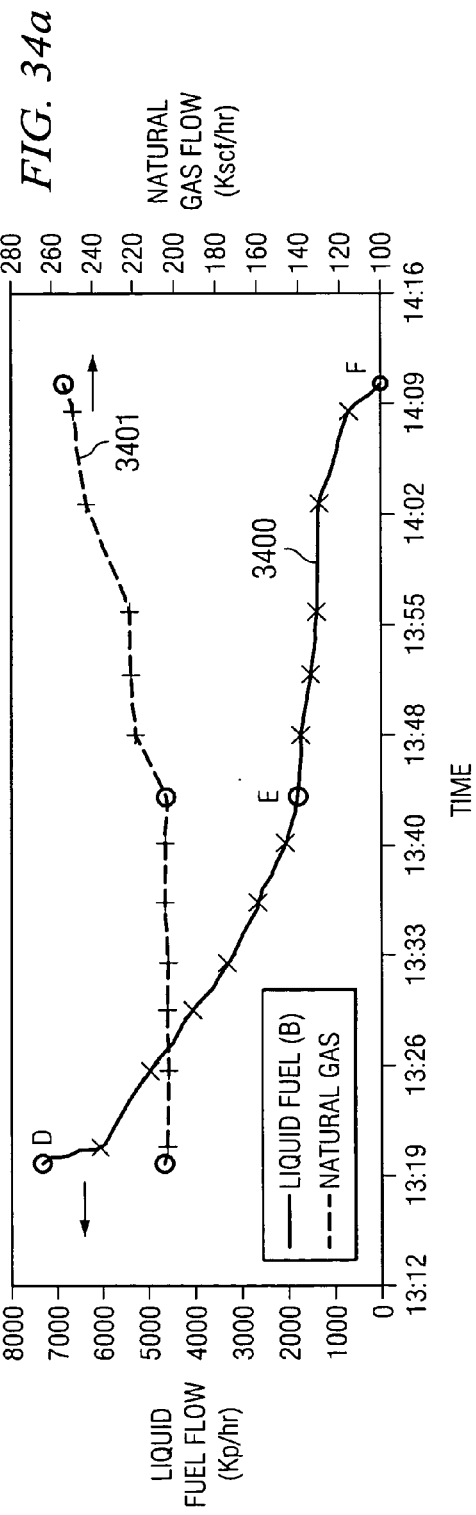
FIGS. 34a and 34b are graphical depictions of the flow rate of liquid fuel(B) and steam flow rate over time for case II.
Figure 34B:
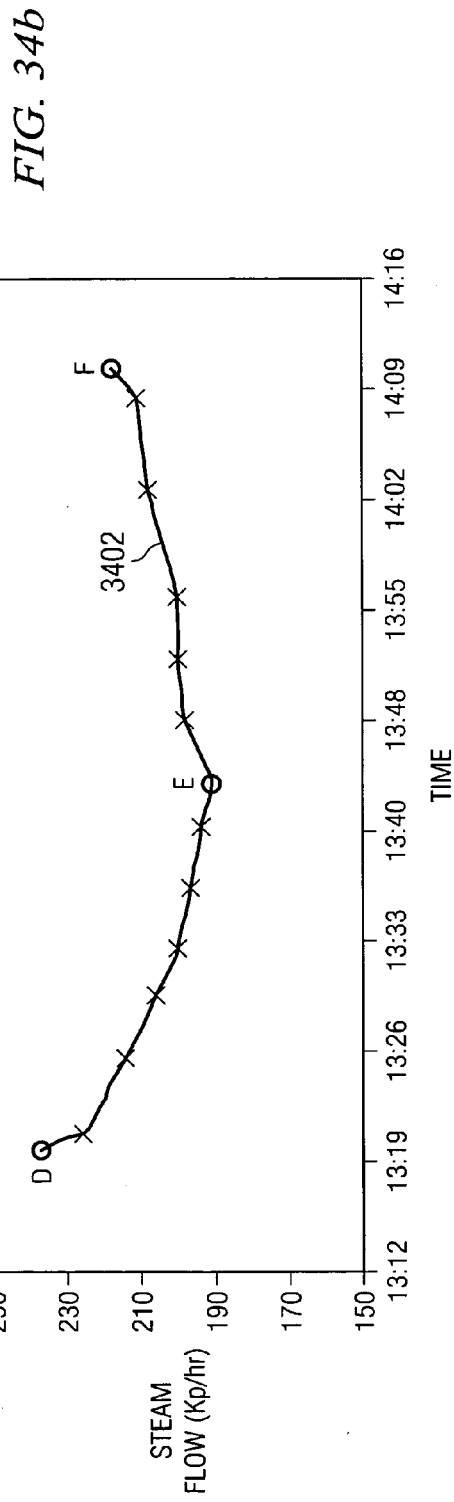

Case II is a 56-minute boiler process where liquid fuel is gradually shut off. In this case, both a liquid fuel (B) and natural gas are used. During this period of time the flow rate of liquid fuel represented by the data point line 3400 in FIG. 34 is gradually reduced from 7000 kp/hr to 0 kp/hr and, at the same time, the flow rate of natural gas represented by a data point line 3401 is increased from 203 kscf/hr to 253 kscf/hr to keep the steam generated at a constant level. The changes in the flow rates of the two fuels are trended in FIG. 34-a and the consequential change in the steam flow rate is represented by a data point line 3402 in FIG. 34-b. In both cases, the air/fuel ratio of the boiler is automatically modulated based on a pre-set control scheme. Therefore, only flow rates of the fuels are considered.

For Cases I and II, 6,840 and 3,360 image frames were recorded, respectively. In FIG. 55, sample images 5500-5505 are shown corresponding to the points marked A through F in FIG. 33 and FIG. 34. For each point A through F, two consecutive images with a one second time difference are shown. It is reasonable to assume that during this one second, the global combustion condition is kept constant. It can be observed that the flames in the boiler appear highly turbulent, which brings about the difficulty of extracting stable and reliable information about the combustion process. It should be noted that the camera positions are not exactly the same for Case I and Case II. However, the outcome of these studies shows that this difference in location of the camera is not a significant influence.

Table 5 contains information corresponding to the sample images 5500-5505 found in FIG. 55 and also corresponding to the points marked A through F in FIG. 33 and FIG. 34.

TABLE 5

Information from Sample Images of Cases I and II

| Case | Point in FIGS. 33 and 34 | Combustion Conditions | Identifier in FIG. 55 |
| --- | --- | --- | --- |
| I | A | Fuel (A): 12100 Kp/hr Steam: 206.4 Kp/hr | 5500 |
|  | B | Fuel (A): 6000 Kp/hr Steam: 163.7 Kp/hr | 5501 |
|  | C | Fuel (A): 12000 Kp/hr Steam: 205.9 Kp/hr | 5502 |
| II | D | Fuel (B): 7320 Kp/hr Natural Gas: 204 Kscf/hr Steam: 237 Kp/hr | 5503 |
|  | E | Fuel (B): 1780 Kp/hr Natural Gas: 203 Kscf/hr Steam: 191 Kp/hr | 5504 |
|  | F | Fuel (B): 0 Kp/hr Natural Gas: 253 Kp/hr Steam: 217 Kp/hr | 5505 |

Each flame image captured is an RGB colour image. The colour image is expressed as a 3-way matrix. Two dimensions represent the x-y spatial coordinates and the third dimension is the colour channel. Therefore, it is a multivariate image composed of three variables (R, G and B channels). In this embodiment, the feature variables extracted are obtained using Multivariate Image Analysis (MIA) techniques, which are based on multi-way Principle Component Analysis (PCA).

Without considering the spatial coordinates of pixels, the image matrix can be unfolded and expressed as a 2-way matrix.

$$I_{N_{row} \times N_{col} \times 3} \xrightarrow{unfold} I_{N \times 3} = \begin{bmatrix} c_{1,r} & c_{1,g} & c_{1,b} \\ \vdots & \vdots & \vdots \\ c_{i,r} & c_{i,g} & c_{i,b} \\ \vdots & \vdots & \vdots \\ c_{N,r} & c_{N,g} & c_{N,b} \end{bmatrix} = \begin{bmatrix} c_1 \\ \vdots \\ c_i \\ \vdots \\ c_N \end{bmatrix}$$

I is the three-way image matrix with image size $N_{row} \times N_{col}$. I is the unfolded two-way image matrix. N is the number of pixels in the image, $N = N_{row} \times N_{col}$. $c_{i,r}, c_{i,g}, c_{i,b}$ (i=1,...,N) are the intensity values of the R, G and B channels for pixel i. $c_i$ (i=1,...,N) is the i-th row vector of I, which represents the colour values of pixel i. Multi-way PCA is equivalent to performing PCA on the unfolded image matrix I.

$$I = \sum_{k=1}^{K} t_k p_k^T + E$$

where K is the number of principal components, the $t_k$'s are score vectors and the corresponding $p_k$'s are loading vectors. For an RGB colour image, the maximum number of principal components is three.

Since the row dimension of the I matrix is very large (equal to 19,200 for a 120*160 image space) and the column dimension is much smaller (equal to 3 for an RGB colour image), a kernel algorithm is used to compute the loading and score vectors. In this algorithm the kernel matrix ($I^T I$) is first formed (for a set of images, the kernel matrix is calculated as $$\sum_j I_j^T I_j),$$

and then singular value decomposition (SVD) is performed on this very low dimension matrix (3×3 for an RGB colour image) to obtain loading vectors $p_\alpha$ ($\alpha=1, \ldots A$).

After obtaining loading vectors, the corresponding score vectors $t_k$ are then computed via $t_k = I \cdot p_k$. $t_k$ is a long vector with length N. After proper scaling and rounding off, it can be refolded into the original image size and displayed as an image.

$$s_{k,i} = \text{Round}\left(\frac{t_{k,i} - t_{k,min}}{t_{k,max} - t_{k,min}} \times 255\right), i = 1, \ldots, N$$

-continued $$(s_k)_{N \times 1} \xrightarrow{refold} (T_k)_{Nrow \times Ncol}$$

$T_k$ is the score image of component k. The values of $T_k$ are integers from 0 to 255. It should be pointed out that when many images are studied, a common scaling range ($t_{k,min}$ and $t_{k,max}$) should be used for all the images.

Figure 35:
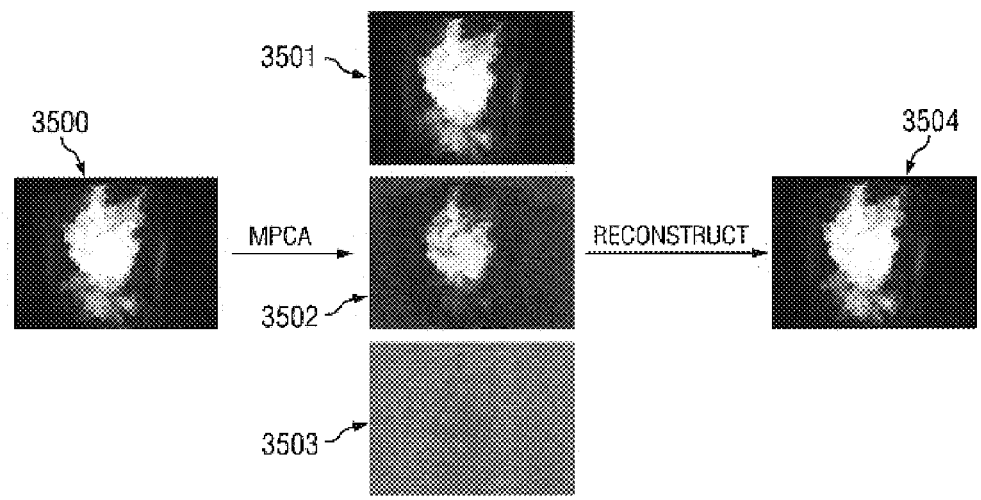
FIG. 35 is a series of flame images showing the transformation of an original flame image to a reconstructed image using principal score images.

One hundred images are used in this example to compute the loading matrix and score scaling range. The first two components explained 99% of the total variance. In FIG. 35, three score images 3501, 3502, 3503 are shown for a sample image 3500. A reconstructed image 3504 from the first two components 3501, 3502 is also shown. It is observed that the $T_3$ score image 3503 contains very little information, which is mainly noise. The reconstructed image 3504 from the first two components 3501, 3502 is almost the same as the original image 3500. Since the first two components 3501, 3502 explain most of the variance, instead of working in the original 3-dimensional RGB space, working in the 2-dimensional orthogonal $t_1$-$t_2$ score space allows us to interpret the images 3501, 3502 more easily.

Inspection of the $t_1$-$t_2$ score plot is a common tool in general PCA analysis to give an overview of the whole system and/or detect clusters or outliers. However, when studied objects are images there are a large number of pixels in a $t_1$-$t_2$ score plot, and many pixels overlap each other. A 256×256 histogram is used to describe the $t_1$-$t_2$ score plot space in this situation and a colour coding scheme may be used to indicate the intensity of the pixel locations in the score plot. This two-dimensional histogram, denoted as TT, can be obtained from rounded and scaled $T_1$ and $T_2$ score images. TT is a 256×256 matrix and is computed as follows:

$$TT_{i,j} = \sum_{k,l} 1, \forall (k, l), T_{1k,l} = i - 1 \,\&\, T_{2k,l} = j - 1$$

i,j=1,...256, k=1,...,120, l=1,...,160

FIG. 56 shows colour score plots for the sample images shown in FIG. 55. In a colour plot, in the colour scheme of the score plots, a darker colour indicates a lower intensity (black indicates no pixel falling at the particular location) and a brighter colour indicates a higher intensity. Higher intensity in these plots indicates higher amounts of overlapping of pixels. FIG. 56 shows that for the same combustion condition, the locations of pixels in the score plots are similar. As the combustion condition changes, the locations of pixels also change.

Each location in a $T_1$-$T_2$ score plot represents a certain colour (ignoring the variation in $t_3$). The colour for each location may be computed by the following formula:

$$[R\ G\ B]_{ij} = t_1(i) \cdot p_1^T + t_2(j) \cdot p_2^T,\ i,j=1, \ldots 256 \text{ where}$$
$$t_1(i) = (i-1) \cdot (t_{1,max} - t_{1,min}) + t_{1,min},\quad t_2(j) = (j-1) \cdot$$
$$(t_{2,max} - t_{2,min}) + t_{2,min} \quad (6)$$

Figure 36:
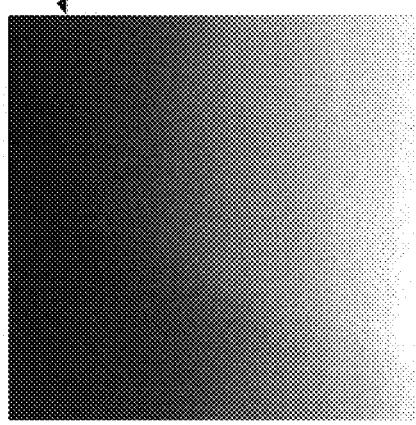
FIG. 36 depicts a colour plane image for a $t_1$-$t_2$ score plot of the reconstructed flame images shown in FIG. 35.

A colour plane is then computed for each score plot as shown in FIG. 36. The relation between the position in the score plot and the colour is observed. Because under different combustion conditions the colours of the flames are different, there is movement between successive plots in score plot space.

Score plots contain important information about the flame; however, directly monitoring the process based on score plots is not practical. This is due mainly to the difficulty for a person to monitor a process over time by observing the changes in a two-dimensional matrix. Even for a person who is able to detect some change occurring in a score plot, it is still difficult to correlate such changes with the changes in the process variables. Therefore, it is desirable to extract features that have more physical meaning to the observer and further relate those features with the process measurements to help one gain a greater understanding of flames and the combustion process.

The features discussed in this alternative embodiment can be divided into two categories. The first category is called luminous features, including flame luminous region area, flame brightness, flame intensity uniformity and the furnace wall intensity. The second category is called colour features, including average colour of the whole image, average colour of the flame luminous region and the number of colours appeared in the flame region.

Figure 37A:
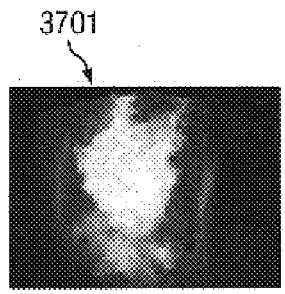
FIGS. 37a and 37c show sample flame images.
Figure 37B:
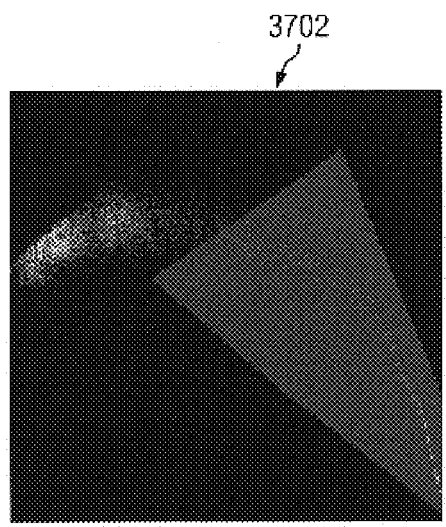
FIG. 37b shows the corresponding $t_1$-$t_2$ score plot including an applied mask shown as a green triangular region on FIG. 37b.
Figure 37C:
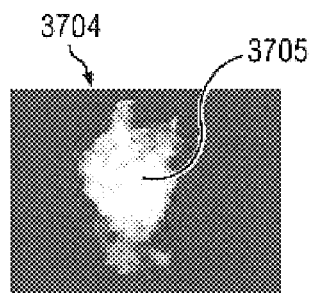

The flame luminous region is selected by choosing a flame mask in the score plot space. The mask is a 256×256 binary matrix, denoted by M. A pixel value is equal to 1 if the colour of this location is a flame colour; otherwise the pixel value is equal to 0. The dimension of the mask is made by trial and error. The final mask for the flame is shown in FIG. 37. Specifically, in FIG. 37-$a$, a sample image 3701 is shown. The corresponding score plot 3702 is shown in FIG. 37-$b$. The mask of flame region is shown as the triangular area 3703. If all pixels falling outside this mask are depicted as gray colour 3704, the image shown in FIG. 37-$c$ is obtained.

It is then observed that the flame region 3705 is separated from the other parts of the image.

Luminous Region Area

The luminous region area is the area of the flame region defined above. It can be easily computed by counting the number of the pixels falling inside the flame mask.

$$A = \sum_{i,j} TT_{i,j}, \forall (i, j), M_{i,j} = 1, i, j = 1, \ldots 256$$

Flame Brightness

Flame brightness can be obtained by integrating the luminous intensity level contributed from all pixels falling inside the luminous region. The luminous intensity level for any location inside the score plot is computed by converting the colour plane obtained by equation (6) to a gray scale plane as follows $$L_{i,j} = [R\,G\,B]_{i,j} \cdot \begin{bmatrix} 0.299 \\ 0.587 \\ 0.114 \end{bmatrix}, (i,j) = 1, \ldots, 256$$

in which $L_{ij}$ is the luminous intensity level for location (i,j) in the score plot. Therefore, the flame brightness is calculated as:

$$B = \sum_{i,j} TT_{i,j} \cdot L_{i,j}, \forall (i, j), M_{i,j} = 1$$

Flame Luminous Uniformity

Flame luminous uniformity is defined as the standard deviation of luminous intensity of the flame region:

$$U = \sqrt{\frac{\sum_{i,j} TT_{i,j} \cdot L_{i,j}^2 - \sum_{i,j} TT_{i,j} \cdot L_{i,j}}{\sum_{i,j} TT_{i,j}}} = \sqrt{\frac{\sum_{i,j} TT_{i,j} \cdot L_{i,j}^2 - B}{A}},$$

$$\forall (i, j), M_{i,j} = 1$$

Average Brightness of the Boiler Wall

By observing the sample images shown in FIG. 55, the installed camera is facing the flame, which means the camera blocks the ability to see the length of the flame. Moreover, the flame image is a two-dimensional projection of a three-dimensional field and only part of the flame is captured in the image. The brightness of the boiler wall yields information of the flame length and/or the volume of the flames. The average brightness of the boiler wall is computed by:

$$W = \frac{\sum_{i,j} TT_{i,j} \cdot L_{i,j}}{\sum_{i,j} TT_{i,j}}, \forall (i, j), M_{i,j} = 0$$

Average Colour of the Whole Flame Image

The average colour of the whole flame image is expressed as the average location of pixels in the score plot.

$$T_{1m} = \frac{\sum_{i,j} TT_{i,j} \cdot (i-1)}{N}, T_{2m} = \frac{\sum_{i,j} TT_{i,j} \cdot (j-1)}{N}, i, j = 1, 2, \ldots 256$$

in which N is the total number of pixels in the image.

Average Colour of the Flame Region

The average colour of the flame region is defined as the average location of the pixels belonging to the flame region.

$$T_{1f} = \frac{\sum_{i,j} TT_{i,j} \cdot (i-1)}{A}, T_{2f} = \frac{\sum_{i,j} TT_{i,j} \cdot (j-1)}{A}, \forall (i, j), M_{i,j} = 1$$

Number of Colours Appearing in the Flame Region

The number of the different colours appearing in the flame region is the area of flame region in the score plot space.

$$N_c = \sum_{i,j} 1, \forall (i, j), TT_{i,j} \cdot M_{i,j} \neq 0$$

Because of the high turbulence in the combustive process, the feature variables express large variations making it difficult to see the trend of the process. An effective way to reduce these variations is to filter the raw data.

Figure 38A:
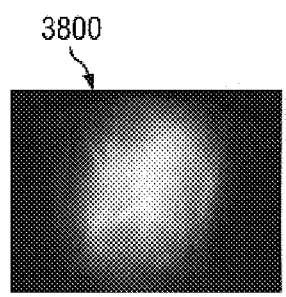
FIGS. 38a and 38b show an averaged image (over 60 consecutive images) and the corresponding score plot, respectively.
Figure 38B:
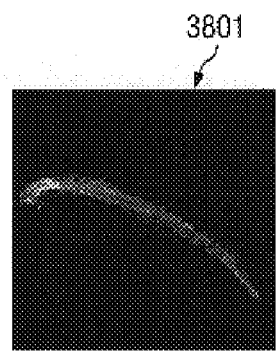

There are several possible filtering techniques that can be used at different stages of the calculation. The first one is to perform the filtering operation in the image space. This technique is the most commonly used method of preprocessing flame studies in the literature. However, in the highly turbulent flame circumstance, as shown in the example averaged image 3800 in FIG. 38-*a*, averaging in the image space could lead to a loss of flame characteristics. In the score plot space 3801, the shape of the averaged image (see FIG. 38-*b*) has been 'distorted' compared to the single frame image (the score plots of point A in Table 5).

Figure 39:
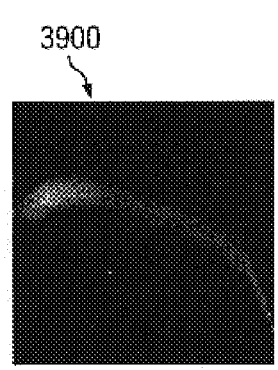
FIG. 39 is an averaged score plot of the flame image in FIG. 38a in a $t_1$-$t_2$ score space.

The second filtering technique is to perform a filter on the score plot space. FIG. 39 shows an averaged TT score plot 3900. Compared to FIG. 38-*b*, this averaged score plot 3900 keeps the basic shape of the score plot of the individual image 3801. The feature variables extracted from the averaged score plot 3900 are expected to summarize the characteristics of the flame during the short period of time. However, the values of the features extracted from the filtered score plots may have different numerical amounts from the features extracted from the raw images because the calculation of feature extraction is not linear.

Figure 40A:
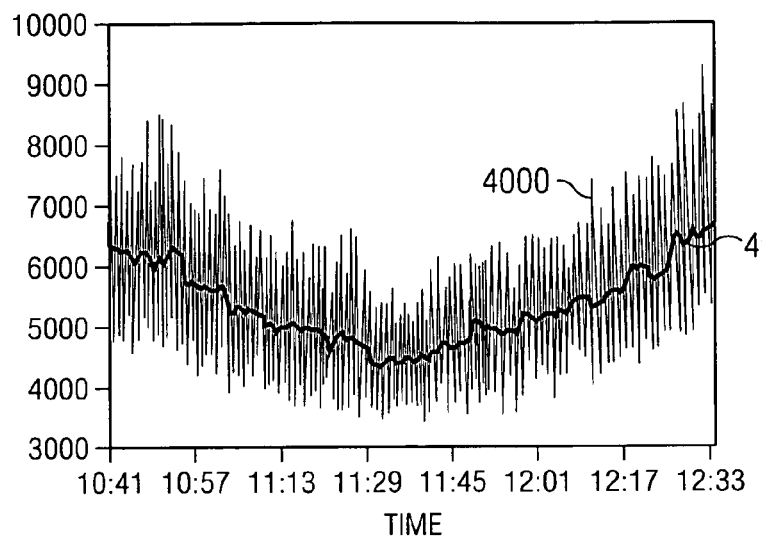
FIG. 40a-40i show a series of plots of feature variables for case I with light lines representing filtered values and the dark regions representing raw data values.
Figure 40B:
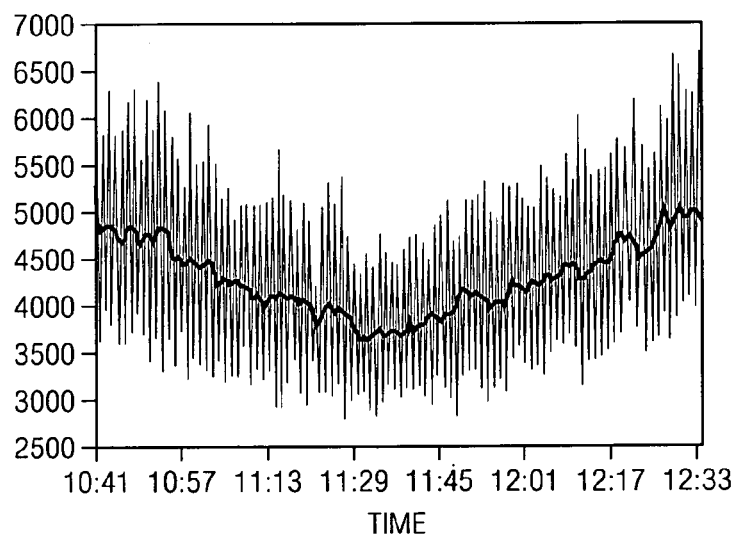
Figure 40C:
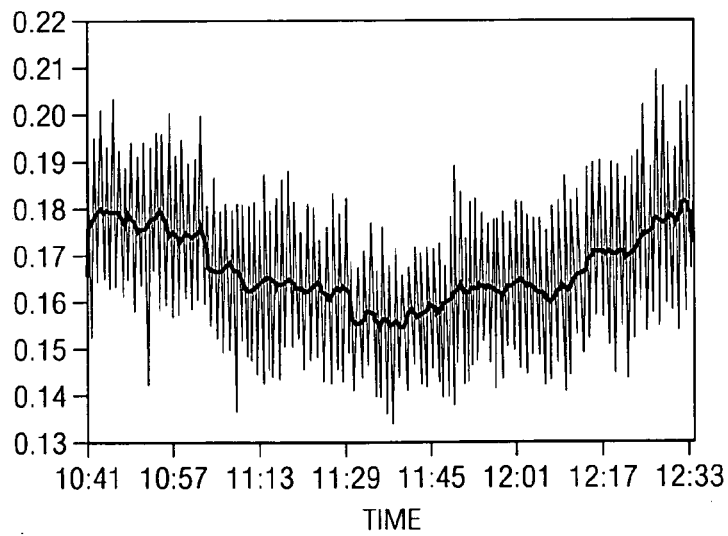
Figure 40D:
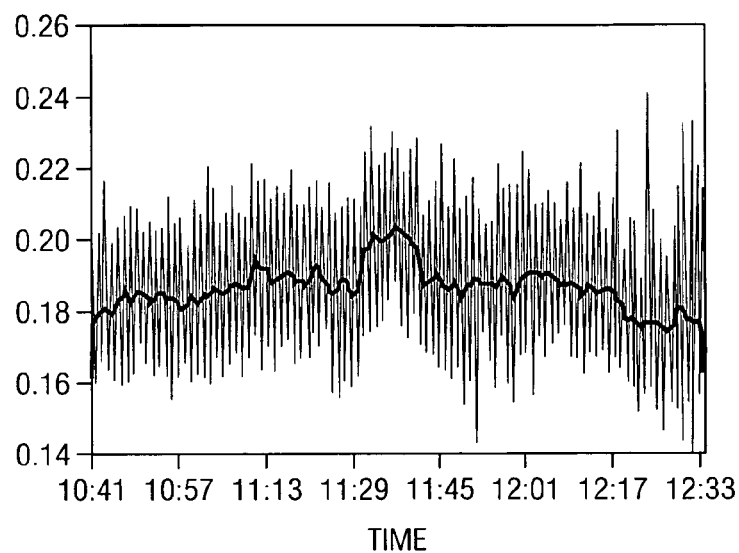
Figure 40E:
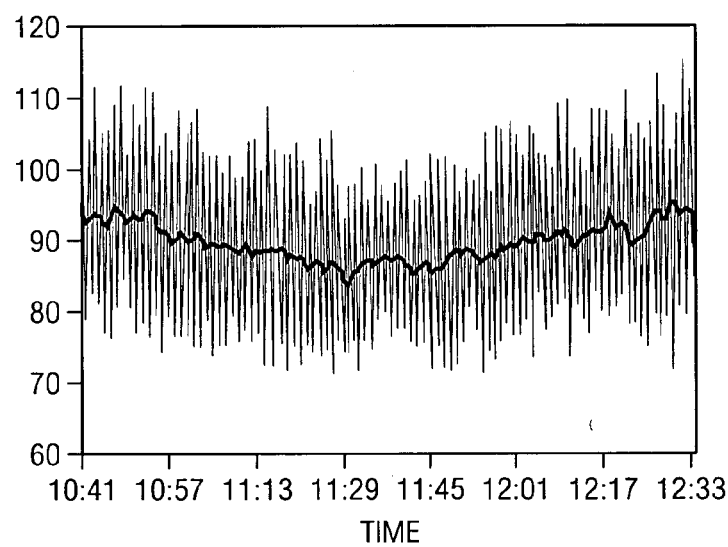
Figure 40F:
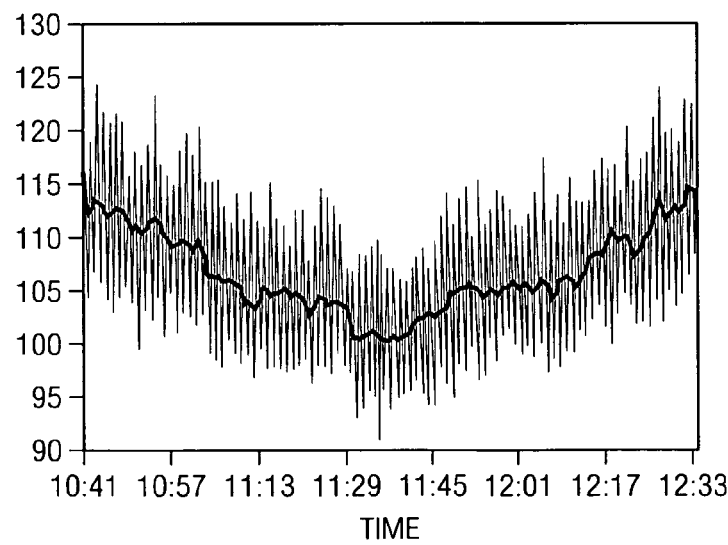
Figure 40G:
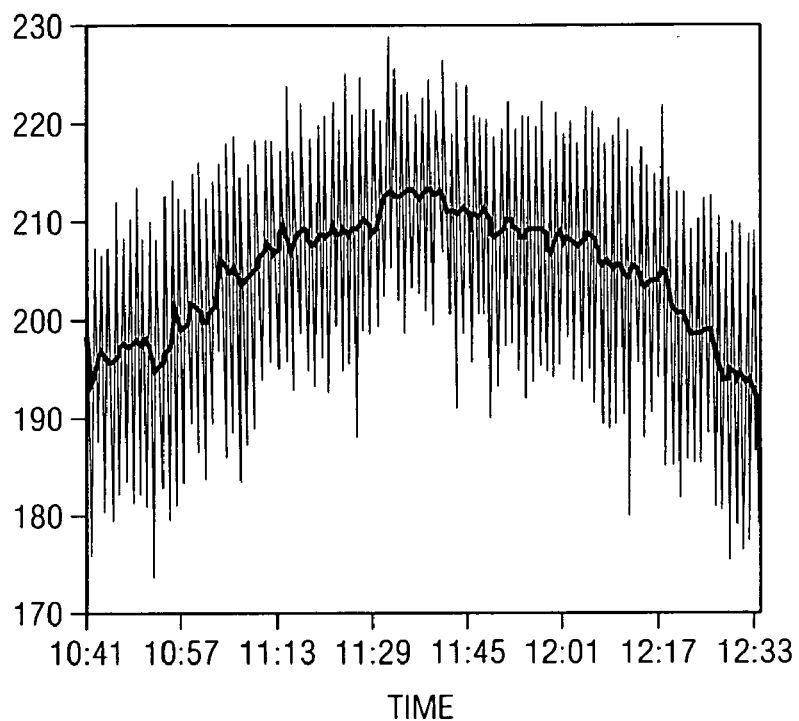
Figure 40H:
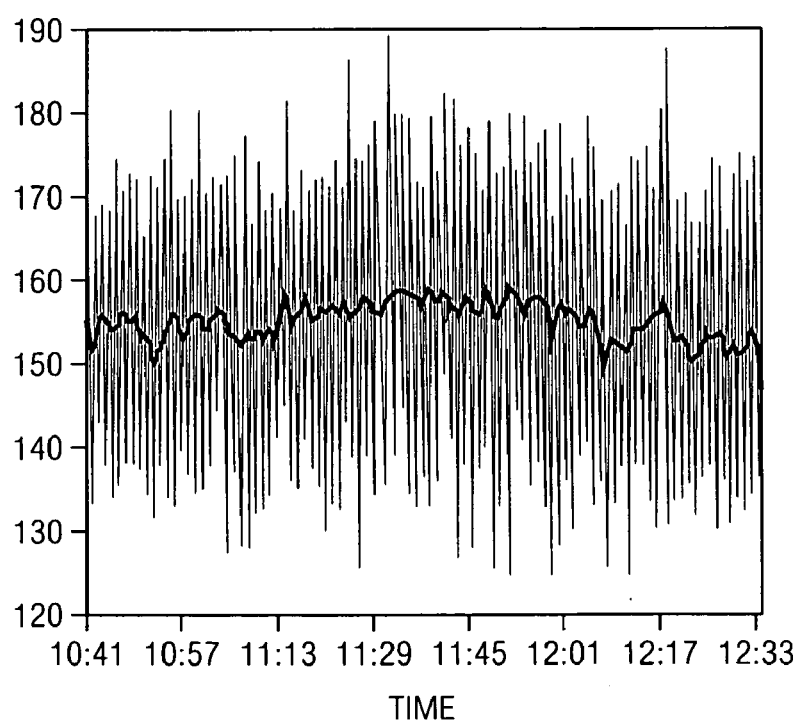
Figure 40I:
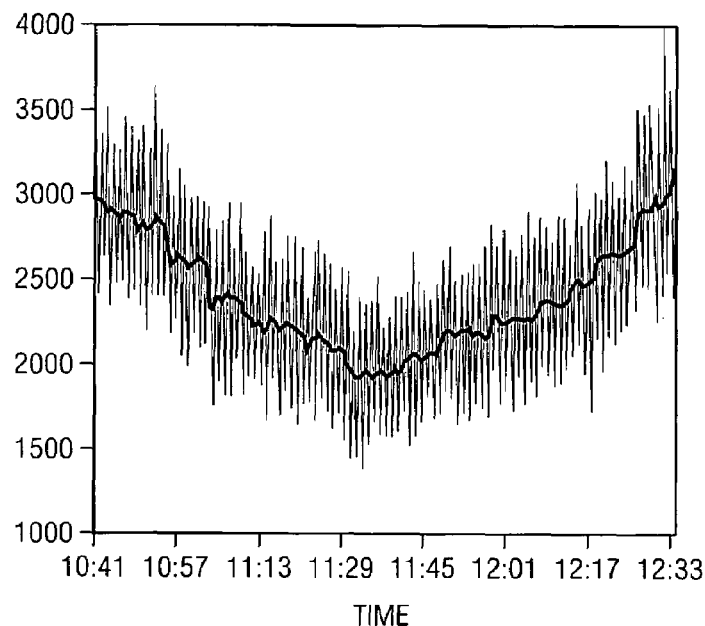
Figure 41A:
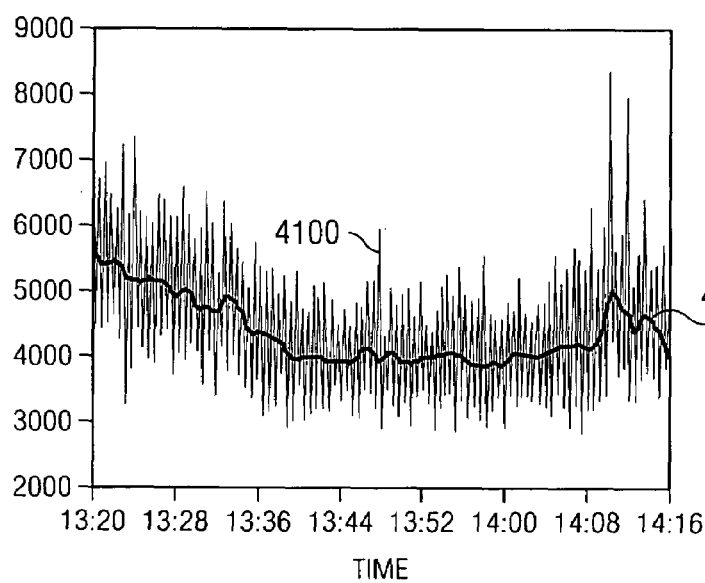
FIG. 41a-41i show a series of plots of feature variables for case II with light lines representing filtered values and dark regions representing raw data values.
Figure 41B:
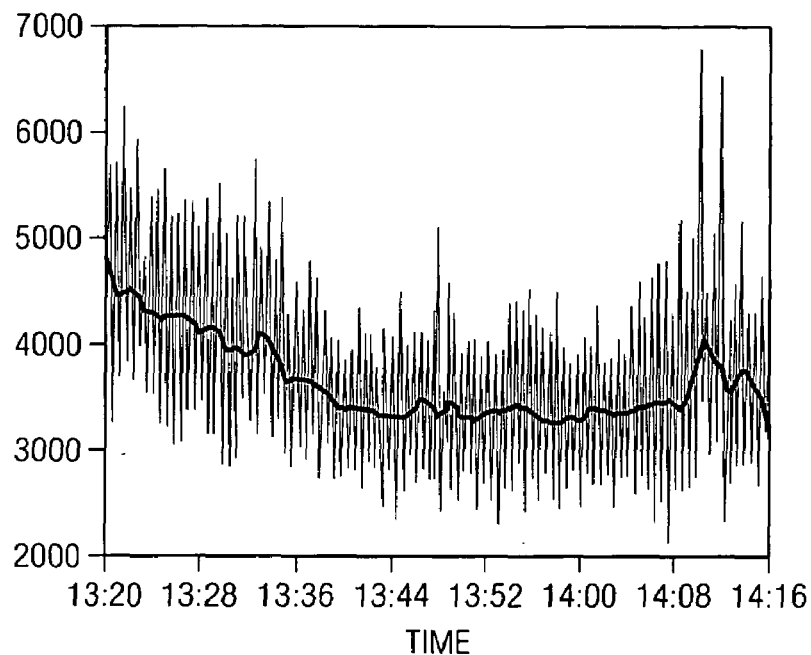
Figure 41C:
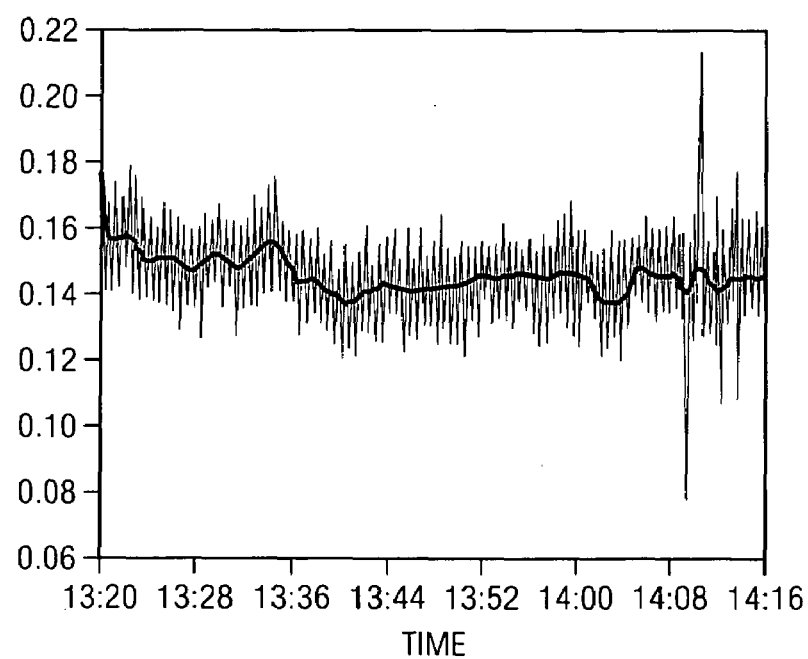
Figure 41D:
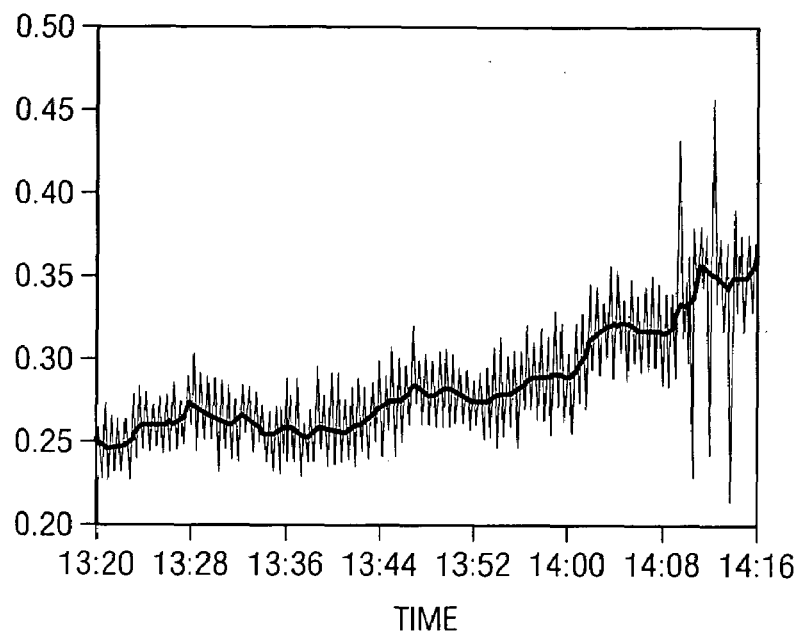
Figure 41E:
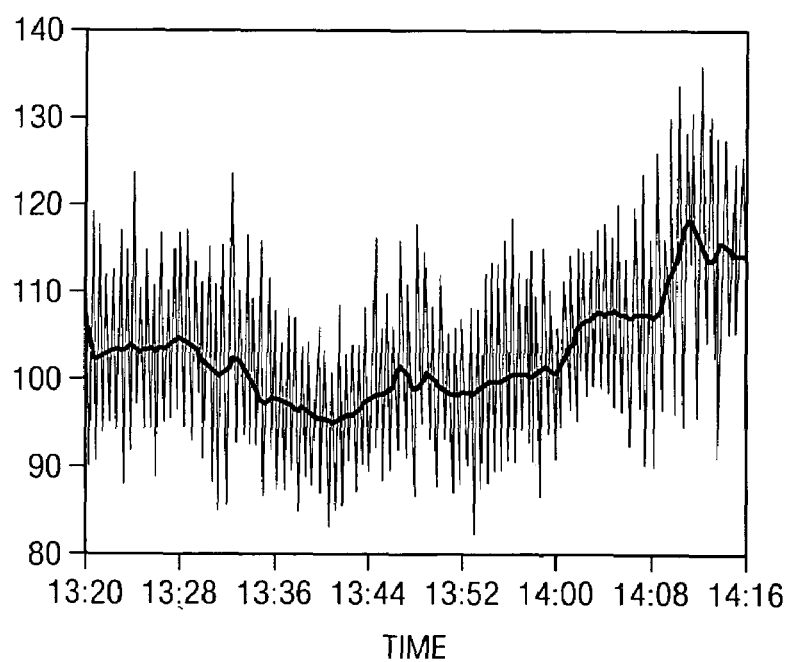
Figure 41F:
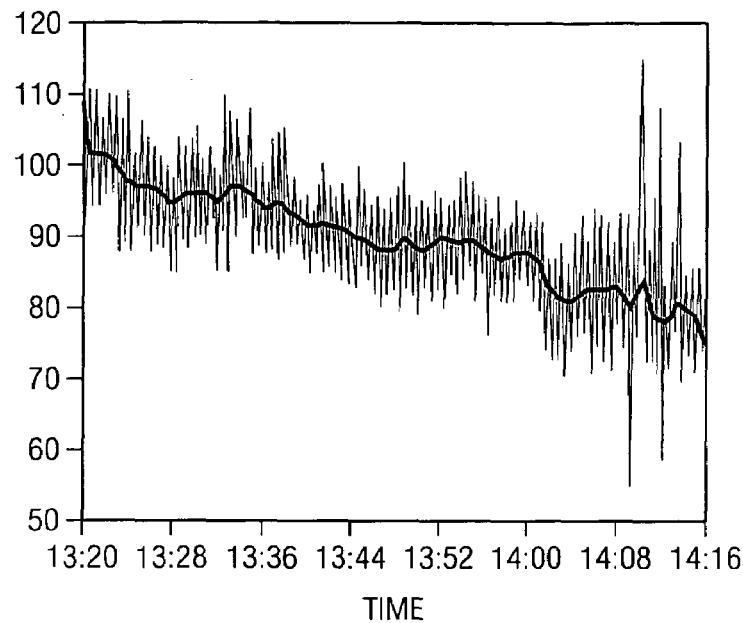
Figure 41G:
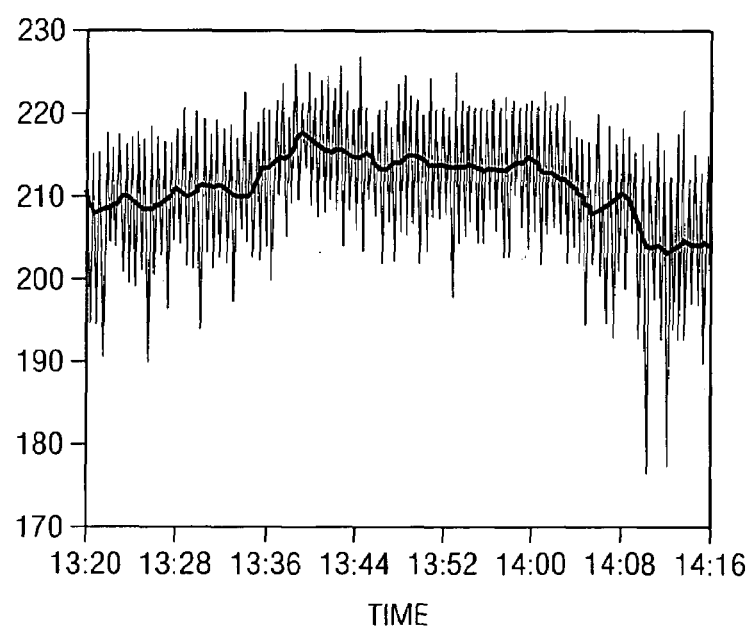
Figure 41H:
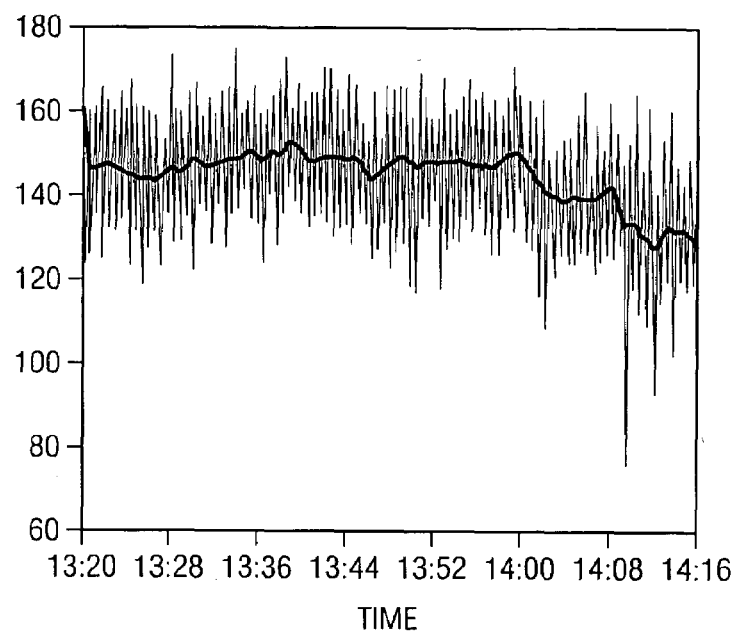
Figure 41I:
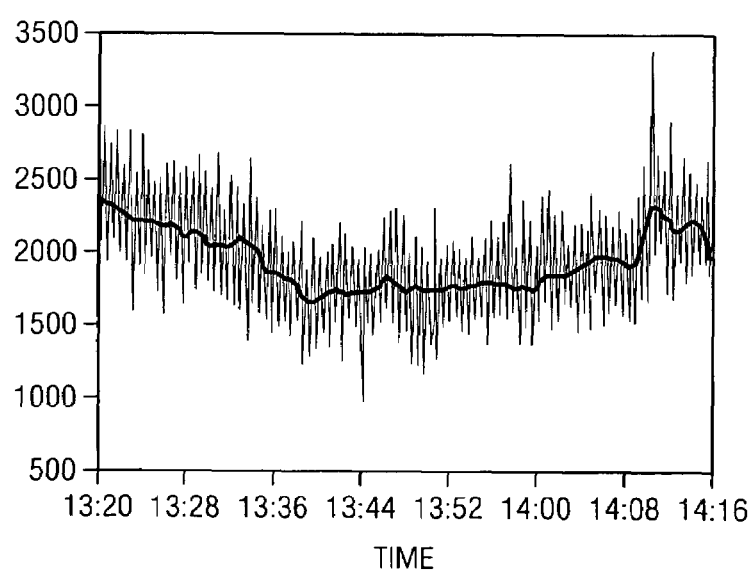

The third filter approach is to apply a filter on the extracted feature variables of the individual frame. This approach has several advantages compared to the other two filtering techniques discussed herein. First, it is much easier to handle the time series data such that at each time point, the data is a vector rather than a matrix. Second, the filtered data points have integrity with the raw feature variables. In this embodiment, the function 'filtfilt' in Matlab Signal Processing Toolbox filters the raw feature variables. This function performs zero-phase digital filtering by processing the input data in both the forward and reverse directions. After filtering in the forward direction, it reverses the filtered sequence and runs it back through the filter. The resulting sequence has precisely zero-phase distortion. In addition to the forward-reverse filtering, it also attempts to minimize startup and ending transients by adjusting initial conditions. The filter weights used in this example are an averaging filter with window length of 60. In fact, filtered features obtained by these three filters in most cases show similar trends. However, since the third filter is the simplest one and yields the smoothest results, it is the filter used in the following computation example. FIGS. 40*a* through 40*i* and FIGS. 41*a* through 41*i* are depictions of the feature variables for the following pair of case examples which include flame area (FIG. 40*a* and FIG. 41*a*), flame brightness (FIG. 40*b* and FIG. 41*b*), flame uniformity (FIG. 40*c* and FIG. 41*c*), average intensity of the boiler wall (FIG. 40*d* and FIG. 41*d*), average $T_1$ value of image (FIG. 40*e* and FIG. 41*e*), average $T_2$ value of image (FIG. 40*f* and FIG. 41*f*), average $T_1$ value of flame (FIG. 40*g* and FIG. 41*g*), average $T_2$ value of flame(FIG. 40*h* and FIG. 41*h*), and the total colour number of the flame region (FIG. 40*i* and FIG. 41*i*).

In Case I, the darker areas of the graphed data points 4000 represent raw data values, while a line 4001 represents the filtered values. The flow rate of the liquid fuel (A) flow rate first decreases and then increases back to the original value. FIGS. 40*a* through 40*i* show that all the feature variables follow the same trend or the inverse trend as the liquid fuel flow rate changes. Likewise, in Case II the darker areas of the graphed data points 4100, represent raw data values, while a line 4101 represents the filtered values. In Case II, both the liquid fuel (B) and natural gas flow rate were variable. Therefore, in Case II the trends of the feature variables are different. Compared to FIG. 34, it is observed that some of the trends are similar to the changes in liquid fuel flow rate, such as the average $T_2$ value of the whole image; some of the trends are similar to the changes in natural gas flow rate, such as average $T_2$ value of the flame region. To have a better understanding of the relation between image feature variables and process measurements, multivariate statistical methods, such as Principal Component Analysis (PCA) and Partial Least Squares (PLS), are used to obtain more qualitative and quantitative information about the process changes.

Next, three PCA models are obtained for the Case I data, the first half of Case II data and the whole Case II data, respectively. The purpose is to reveal the relationship between the changes of the fuels and the flame properties. The variables included in the PCA models constitute filtered flame feature variables and fuel(s) flow rate.

Model 1: Case I Data

Figure 42:
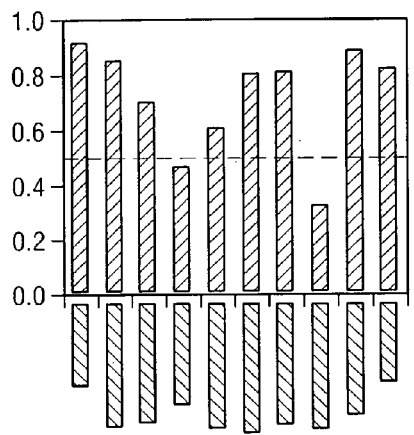
FIG. 42 is a bar graph showing the prediction power of the PCA model for case I.
Figure 43:
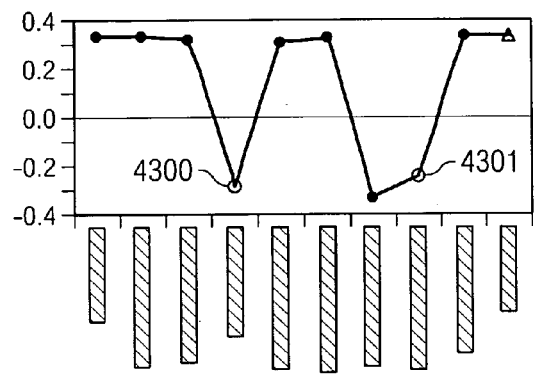
FIG. 43 is a loading plot of the first component of the PCA model for case I.

In the PCA model for case I, the first principal component explained 88.4% of the total variance. This is reasonable since only one factor (flow rate of liquid fuel) is changing in this case. FIG. 42 shows the prediction power for the variables. $v_4$ (wall intensity) and v8 (mean $T_2$ of flame) have low prediction power, which indicates that these two variables contain relatively little dependency on the other process variables. From FIGS. 40*d* and 40*h*, it is observed that $v_4$ and $v_8$ have a very flat trend, which is consistent with the conclusion from the prediction power plot. Therefore, in the loading plot shown in FIG. 43, the values of these two variables were not considered and are indicated by the unfilled circles 4300 and 4301. All variables have a positive correlation as shown in the loading plot depicted in FIG. 43, with the exception of $v_7$, which has a negative correlation.

Model 2: First Half of Case II Data

Figure 44:
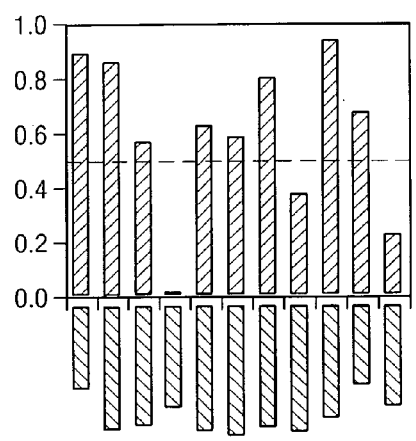
FIG. 44 is a bar graph showing the prediction power of the PCA model for the first half of the data for case II.
Figure 45:
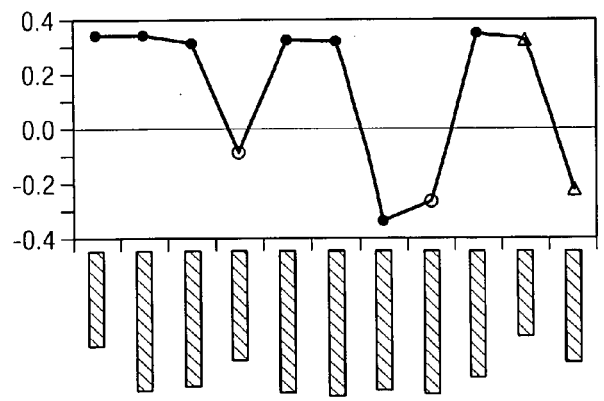
FIG. 45 is a loading plot of the first component of the PCA model for the first half of the data for case II.

In the first half period time of Case II, only the flow rate of liquid fuel (B) decreased and flow rate of natural gas almost kept constant. The first principal component explained 76.7% of the total variance. It is interesting to see from the predict power plot (FIG. 44) and loading plot (FIG. 45) that almost the same relationship between flame image feature variables and liquid fuel flow rate exists, although the compositions of the two liquid fuels in these two cases were different.

Model 3: Whole Case II Data

Figure 46:
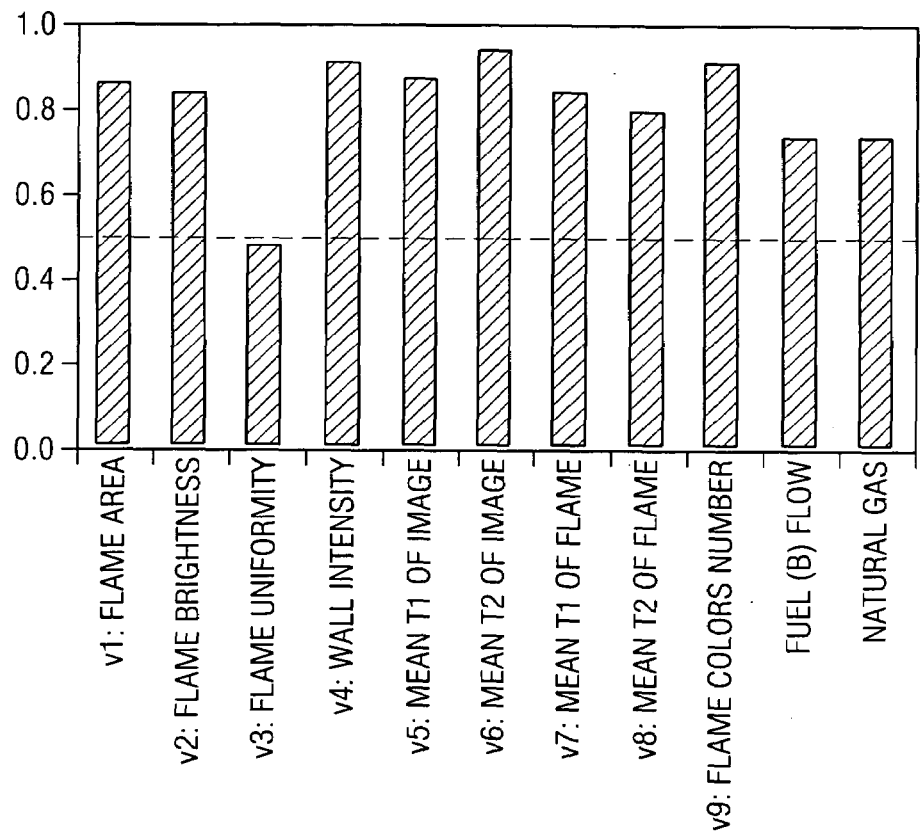
FIG. 46 is a bar graph showing the prediction power of the PCA model all the data for case II.
Figure 47:
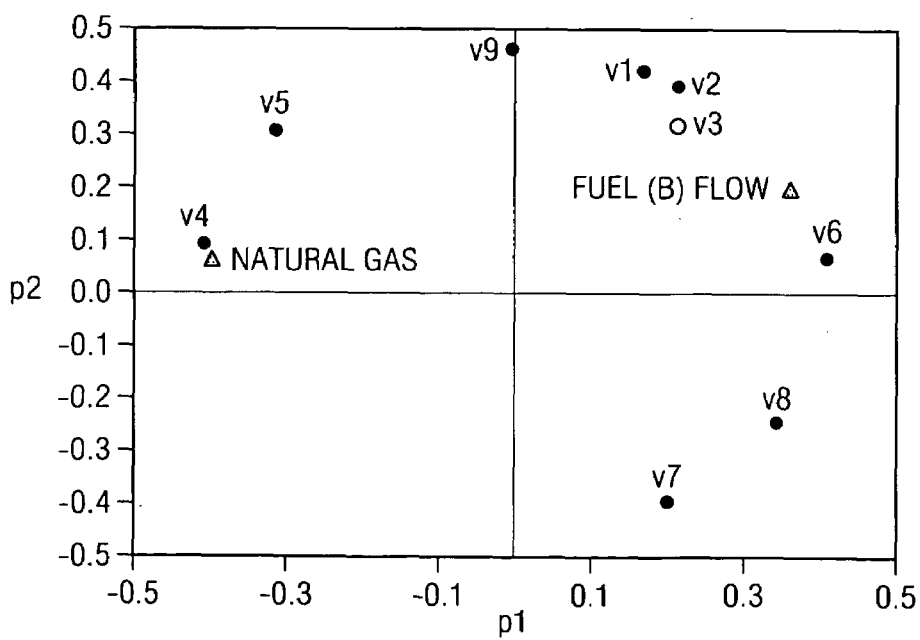
FIG. 47 is a loading plot of the first component of the PCA model for all the data for case II.

In the PCA model for whole Case II the first component explained 52.3% and the second component explained 42.6% of the total variance. In the prediction power plot (see FIG. 46), only $v_3$ (flame uniformity) has low prediction power. Thus, Model 3 is different from Model 1 and Model 2. The difference is probably explained by noting that the variation in natural gas has little influence on $v_3$, $v_4$ and v8. Variations in natural gas, which had low prediction power in Model 1 and Model 2, now have high prediction power. This observation indicates that these two variables have close relationships with natural gas flow rate. From the scatter $p_1$-$p_2$ loading plot (FIG. 47) it is observed that $v_4$ has high positive correlation and $v_8$ has negative correlation with natural gas. A PCA model is then performed on both datasets using flame image feature variables. In total, only two principal components are significant, explaining 97.4% of the variance.

Figure 48:
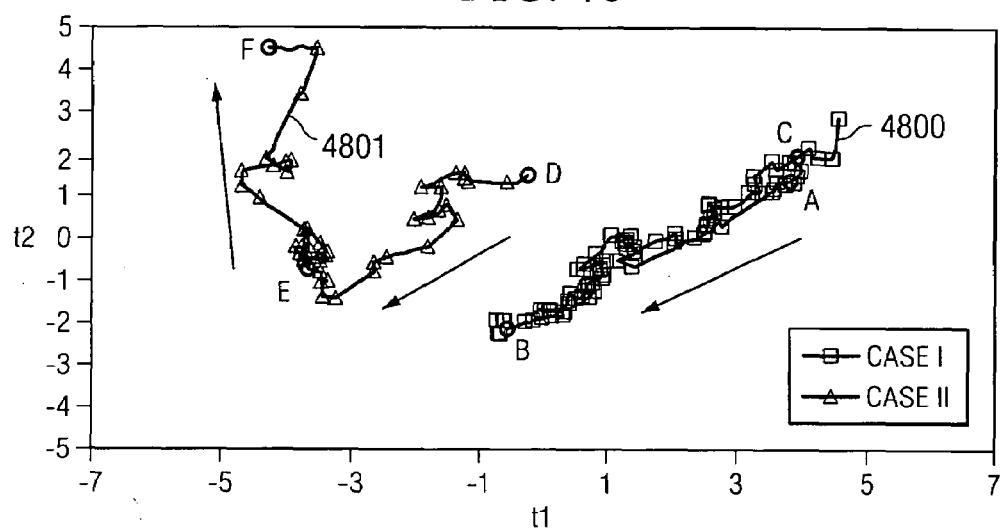
FIG. 48 is a $t_1$ $t_2$ score plot of the PCA model for both cases I and II.

The flame analysis process may be monitored by observing the $t_1$-$t_2$ score plot depicted in FIG. 48. From this score, it may be observed how the process develops as the combustion conditions change. It is interesting to note that both points belonging to Case I 4800 and the points belonging to the first half of Case II 4801 show that as the liquid fuel decreased, the points moved toward the left-bottom corner of the plot. As the flow rate of natural gas increased, the points moved mainly toward the $t_2$ direction. By studying and correlating properties of a flame, it is expected that predictions may be made to control the process including reducing noxious emissions generated from the process and increasing burning efficiency.

Figure 49:
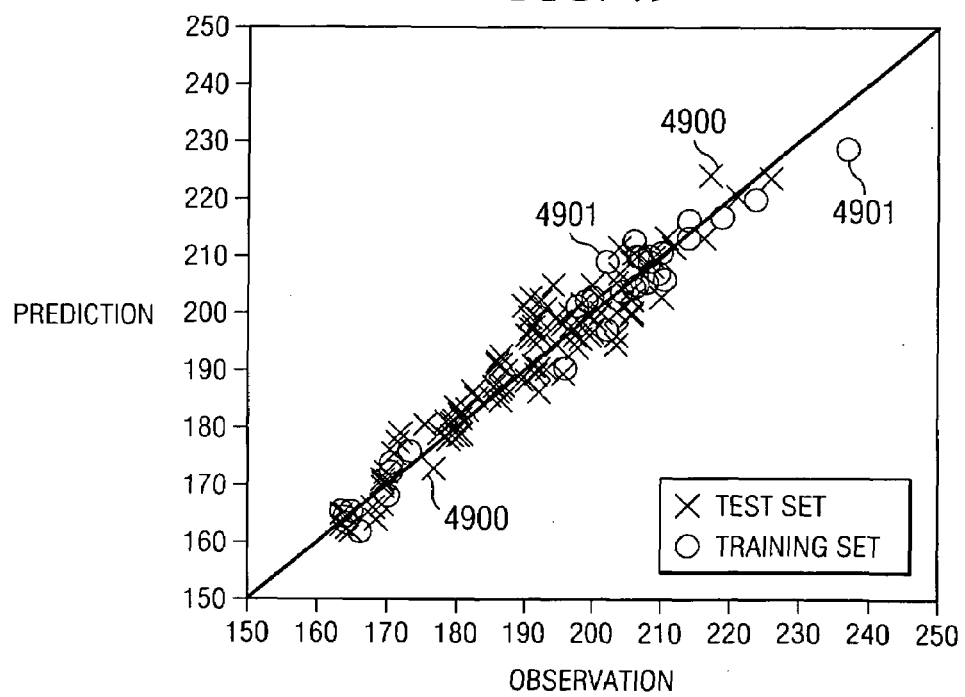
FIG. 49 is a graphical depiction of the predicted steam flow rate versus measured steam flow rate.
Figure 50A:
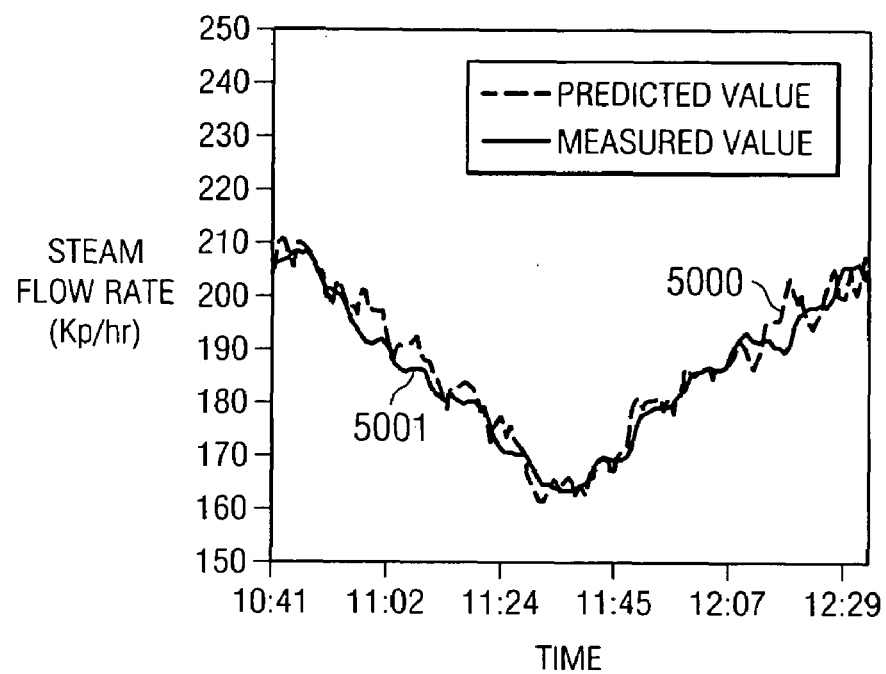
FIGS. 50a and 50b show a comparison of steam flow rates over time for predicted values and measured values, for case I and case II, respectively.
Figure 50B:
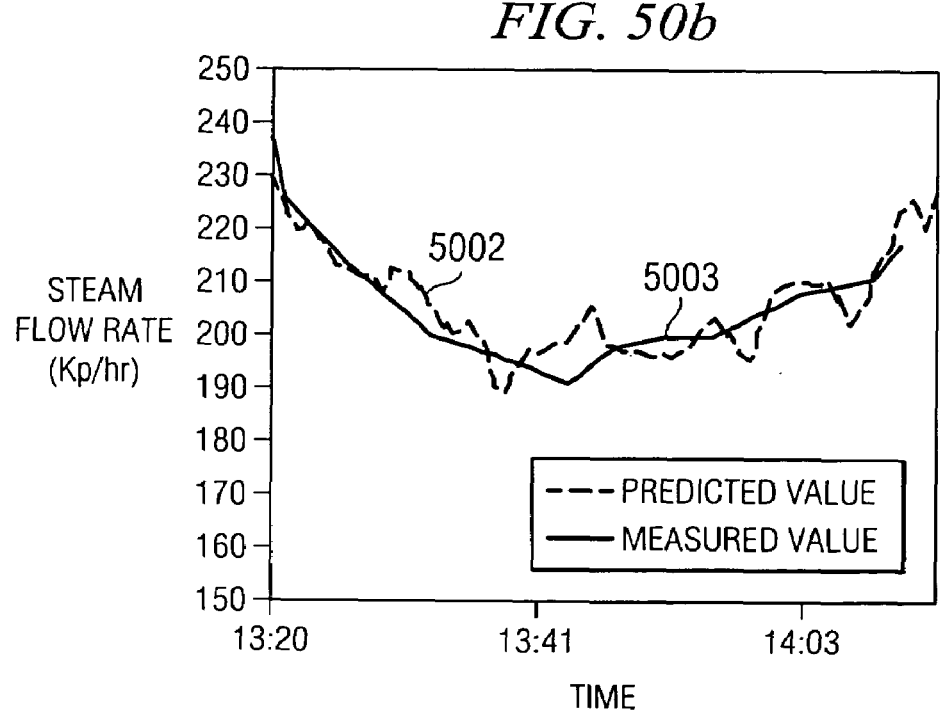

A PLS model may then be constructed to obtain more quantitative information about flame combustion. In this embodiment of the invention, feature variables from flame images can be used to predict flow rate of the generated steam. Six latent variables are used in constructing the PLS model. Thirty-three observations are used as a training dataset and 133 observations are used as a test dataset. The root mean square error (RMSE) for training set is 3.85 and for test set is 3.93, respectively. The prediction versus observation plot is shown in FIG. 49. FIGS. 50a and 50b are the time series plots for the two cases, respectively. For Case I depicted in FIG. 50a, data point line 5000 represents the predicted value of the steam flow rate and data point line 5001 represents the actual measured value of the steam flow rate. For Case II shown in FIG. 50b, data point line 5002 represents the predicted value of the steam flow rate and data point line 5003 represents the actual measured value of the steam flow rate. It is observed that the predicted data points are consistent with the measured data. It is also expected that by combining the image feature variables and other relevant process variables, predictions may be made to control and reduce the noxious emissions generated from the process and increase the burning efficiency of the fuel.

While the invention has been particularly shown and described with reference to several embodiments, it will be understood by those skilled in the art that various other approaches and applications to industry may be made without departing from the spirit and scope of the invention disclosed herein.

We claim:

1. A method of monitoring an organoleptic property of a characterizing product during production of said product, wherein a sequence of more than one multivariate image of the characterizing product has been captured, each image consisting of an image array of pixel elements of measured intensity values in at least three wavelength ranges defining the dimensions for the image array; wherein said method consists of the steps of:
    identifying an organoleptic property of the characterizing product;
    creating an organoleptic feature vector;
    correlating the organoleptic feature vector with the organoleptic property by a regression method; and
    creating an output of the organoleptic feature vector.

2. A method according to claim 1 wherein the multivariate image of the characterizing product is captured in the visible spectrum.

3. A method according to claim 2 wherein the pixel elements of the image array have varying intensities of colours, wherein said colors comprise at least one of red, green, and blue.

4. A method according to claim 1 wherein the multivariate image of the characterizing product is captured in the near infrared spectrum.

5. A method according to claim 1 wherein the organoleptic feature vector consists of average values for each of the said at least three wavelength ranges.

6. A method according to claim 1 wherein one or more other physical process measurements are combined with information contained in the organoleptic feature vector to correlate the physical process measurements with the organoleptic property.

7. A method according to claim 6 wherein said physical process measurement is one selected from the group consisting of: chip moisture content, chip oil content, chip weight per ten, dough moisture.

8. A method according to claim 1 wherein one or more acoustic measurements of a characterizing product are combined with information contained in the organoleptic feature vector to correlate the acoustic measurements with the organoleptic property.

9. A method according to claim 1 wherein one or more acoustic measurements of a characterizing product and one or more other physical process measurements are combined with information contained in the organoleptic feature vector to correlate said acoustic measurements and said physical process measurements with the organoleptic property.

10. A method according to claim 6 wherein a regression method is performed on the physical process measurements before creating the output of the organoleptic feature vector.

11. A method according to claim 8 wherein a regression method is performed on the acoustic measurements before creating the output of the organoleptic feature vector.

12. A method according to claim 1 wherein the organoleptic property of the characterizing product is selected from the group consisting of: blister level, toast points, taste, texture, crispness, crunchiness, peak break force.

13. A method according to claim 1 wherein a multivariate statistical projection method is applied to the image array to reduce the dimensions to a low dimensional score space defined by a small number of score vectors and said organoleptic feature vector is created from said low dimensional score space image data.

14. A method according to claim 13 wherein the multivariate statistical projection method is selected from the group consisting of: multi-way principal component analysis (PCA), multi-way partial least squares (PLS), projection pursuit, independent component analysis.

15. A method according claim 13 wherein the multivariate statistical projection method applied to the image array reduces the dimensions of the image array to a $t_1$-$t_2$ score space.

16. A method according claim 15 wherein the feature vector is a first loading vector $t_1$.

17. A method according to claim 15 wherein the feature vector is obtained by dividing said $t_1$-$t_2$ score space into a plurality of blocks and summing the intensity values within each block.

18. A method according to claim 15 wherein the organoleptic feature vector is created consisting of the steps of:
    applying a multivariate statistical projection method to an image array for a control process to reduce the dimensions to a low dimensional score space having a significant loading vector;
    projecting the $t_1$-$t_2$ score space along a direction defined by said significant loading vector to create a projection vector; and
    creating a histogram from said projection vector to define the organoleptic feature vector.

19. A method according to claim 15 wherein the organoleptic feature vector is created consisting of the steps of:
    applying a multivariate statistical projection method to an image array for a control process to reduce the dimensions to a low dimensional score space having a significant loading vector;
    projecting the $t_1$-$t_2$ score space along a direction defined by said significant loading vector to create a projection vector; and
    creating a cumulative histogram from said projection vector to define the organoleptic feature vector.

20. A method according to claim 15 wherein said organoleptic feature vector is created consisting of the steps of:

calculating covariance matrices $COV_1$ and $COV_2$ between histogram elements from the $t_1$-$t_2$ score space image data for two respective features $Z_1$ and $Z_2$;

calculating an angle matrix from said covariance matrices $COV_1$ and $COV_2$;

superimposing the $t_1$-$t_2$ score space image data on said angle matrix; and calculating a cumulative histogram to define the feature vector.

21. A method according to claim 15 wherein said organoleptic feature vector is created consisting of the steps of:

calculating covariance matrices $COV_3$ and $COV_4$ between histogram elements from a $t_1$-$t_2$ score space image data for two respective features $Z_1$ and $Z_2$ in a control process;

adding covariance matrices $COV_3$ and $COV_4$ and displaying the sum as a colour coded image sum display in a first $t_1$-$t_2$ score space;

selecting a mask to inscribe an area in said sum display in said first $t_1$-$t_2$ space corresponding to a product region;

projecting the multivariate images to said first $t_1$-$t_2$ score space and removing pixels which lie outside said area to create pure product images;

applying a multivariate statistical projection method to the pure product images to reduce the dimensions of the pure product images to a second $t_1$-$t_2$ score space;

calculating covariance matrices $COV_5$ and $COV_6$ between histogram elements from the second $t_1$-$t_2$ score space for said two respective features $Z_1$ and $Z_2$;

calculating an angle matrix from said covariance matrices $COV_5$ and $COV_6$;

superimposing the second $t_1$-$t_2$ score space image data on said angle matrix; and calculating a cumulative histogram to define the organoleptic feature vector.

22. A method according to claim 1 in which the regression method is selected from the group consisting of: principal component regression (PCR); partial least squares (PLS); multivariate linear regression (MLR); artificial neural networks (ANN).

23. A method according to claim 1 wherein the output is displayed as a colour coded image for visual monitoring of operating conditions of the process.

24. A method of monitoring a food product process under changing operating conditions, wherein a food product has been exposed to an electromagnetic radiation source; wherein further a sequence of more than one multivariate image in the electromagnetic spectrum has been captured, each image consisting of an image array having a plurality of pixel elements, each pixel element having intensity values of at least one wavelength in the electromagnetic spectrum defining at least three dimensions for the image array; wherein further a multi-way principal component analysis has been applied to the image array to reduce the dimensions of the image array to a $t_1$-$t_2$ score space; wherein said method consists of the steps of:

creating an organoleptic feature vector from said $t_1$-$t_2$ score space;

performing a regression method to correlate the organoleptic feature vector with an organoleptic property of the food product; and creating an output of the organoleptic property for continuous monitoring and feed back control of operating conditions of the process.

25. A method according to claim 24 wherein one or more other physical process measurements are combined with information contained in the organoleptic feature vector to correlate the physical process measurements with the organoleptic property.

26. A method according to claim 25 wherein a regression method is performed on the physical process measurements before creating the output of the organoleptic property.

27. A method according to claim 25 wherein said physical process measurement is one selected from the group consisting of: chip moisture content, chip oil content, chip weight per ten, dough moisture.

28. A method according to claim 24 wherein one or more acoustic measurements of a characterizing product are combined with information contained in the organoleptic feature vector to correlate the acoustic measurements with the organoleptic property.

29. A method according to claim 28 wherein a regression method is performed on the acoustic measurements before creating the output of the organoleptic property.

30. A method according to claim 24 wherein one or more acoustic measurements of a characterizing product and one or more other physical process measurements are combined with information contained in the organoleptic feature vector to correlate said acoustic measurements and said physical process measurements with the organoleptic property.

31. A method according to claim 24 wherein the organoleptic property of the food product is selected from the group consisting of: blister level, toast points, taste, texture, crispness, crunchiness, peak break force.

32. A method of monitoring a food product process under changing operating conditions, wherein a food product has been exposed to an electromagnetic radiation source; wherein further a sequence of more than one multivariate image of the food product has been captured in the visible spectrum, each image consisting of an image array having a plurality of pixel elements, each pixel element having intensity values generally of the colours red, green, and blue defining three dimensions for the image array; wherein further a multi-way principal component analysis has been applied to the image array to reduce the dimensions of the image array to a first $t_1$-$t_2$ score space; wherein further an area in said first $t_1$-$t_2$ score space has been masked which excludes background from the image array; wherein further the multivariate images have been projected to said first $t_1$-$t_2$ score space and pixels which lie outside said area have been removed to create pure product images; wherein further a multi-way principal component analysis has been applied to the pure product images to reduce the dimensions of the pure product images to a second $t_1$-$t_2$ score space; wherein said method consists of the steps of:

creating an organoleptic feature vector from said second $t_1$-$t_2$ score space;

performing a regression method to correlate the organoleptic feature vector with an organoleptic property of the food product; and creating an output of the organoleptic property for continuous monitoring and feed back control of the operating conditions of the process.

33. A method according to claim 32 wherein one or more other physical process measurements are combined with information contained in the organoleptic feature vector to correlate the physical process measurements with the organoleptic property.

34. A method according to claim 33 wherein said physical process measurement is one selected from the group consisting of: chip moisture content, chip oil content, chip weight per ten, dough moisture.

35. A method according to claim 32 wherein one or more acoustic measurements of a characterizing product are combined with information contained in the organoleptic feature vector to correlate the acoustic measurements with the organoleptic property.

36. A method according to claim 32 wherein one or more acoustic measurements of a characterizing product and one or more other physical process measurements are combined with information contained in the organoleptic feature vector to correlate said acoustic measurements and said physical process measurements with the organoleptic property.

37. A method according to claim 33 wherein a regression method is performed on the physical process measurements before creating the output of the organoleptic property.

38. A method according to claim 35 wherein a regression method is performed on the acoustic measurements before creating the output of the organoleptic property.

39. A method according to claim 32 wherein the organoleptic property of the food product is selected from the group consisting of: blister level, toast points, taste, texture, crispness, crunchiness, peak break force.

40. A method for product organoleptic property monitoring in an on-line environment wherein a food product is exposed to an electromagnetic radiation source; wherein said method consists of the steps of:
   imaging a product with at least one organoleptic property;
   extracting background features from the image;
   extracting any coating features of the product from the image;
   creating an image score plot of the at least one organoleptic property;
   correlating the product organoleptic property to a training sample score plot by statistical regression; and
   predicting the occurrence of the organoleptic property in the imaged product.

41. The method of claim 40 wherein the product organoleptic property is the occurrence, quantity, variance, characteristic, level, or degree of the product organoleptic property in the imaged product.

42. The method of claim 40 wherein said predicting further comprises predicting the occurrence, concentration, or level of the organoleptic property on the imaged product by calculating within subsections of the whole image.

43. The method of claim 40 wherein the occurrence prediction is for the presence or absence of the organoleptic property.

44. The method of claim 40 wherein the organoleptic property is imaged by at least one of the group consisting of: visual light spectrum imaging, infrared spectrum imaging, ultraviolet spectrum imaging, audible sound wave detection, inaudible sound wave detection, mass spectroscopy and chromatography.

45. The method of claim 40 wherein an image acquisition apparatus, a computer processor and computer program for image processing are utilized to reduce the methodology to on-line practice for a product manufacturing process.

46. The method of claim 40 further consisting of automatically adjusting an on-line manufacturing process with closed loop control.

47. The method of claim 40 further consisting of providing quality control images with visualization software for a product manufacturing process thereby providing one or more of the group consisting of: process monitoring, process control, process alarms or defective product aborting.

48. The method of claim 40 wherein the food product is either bedded or not bedded.

49. The method of claim 48 wherein a predicted specific bed depth is used to augment the measurement of other product features which are affected by variable bed depth and distance from the imaging device.

50. The method of claim 40 wherein a specific bed depth model is used to predict a bed depth of the product.

51. A method according to claim 40 wherein one or more other physical process measurements are combined with information contained in an organoleptic feature vector to correlate the physical process measurements with the organoleptic property.

52. A method according to claim 51 wherein a regression method is performed on the physical process measurements before creating an output of the organoleptic property.

53. A method according to claim 51 wherein said physical process measurement is one selected from the group consisting of: chip moisture content, chip oil content, chip weight per ten, dough moisture.

54. A method according to claim 40 wherein one or more acoustic measurements of a characterizing product are combined with information contained in an organoleptic feature vector to correlate the acoustic measurements with the organoleptic property.

55. A method according to claim 54 wherein a regression method is performed on the acoustic measurements before creating an output of the organoleptic property.

56. A method according to claim 40 wherein one or more acoustic measurements of a characterizing product and one or more other physical process measurements are combined with information contained in an organoleptic feature vector to correlate said acoustic measurements and said physical process measurements with the organoleptic property.

57. A method according to claim 40 wherein the organoleptic property of the food product is selected from the group consisting of: blister level, toast points, taste, texture, crispness, crunchiness, peak break force.

58. A method of monitoring a food product process under changing operating conditions, wherein a food product has been exposed to an electromagnetic radiation source; wherein further a sequence of more than one multivariate image in the electromagnetic spectrum has been captured, each image consisting of an image array having a plurality of pixel elements, each pixel element having intensity values of at least one wavelength in the electromagnetic spectrum defining at least three dimensions for the image array; wherein further a multi-way principal component analysis has been applied to the image array to reduce the dimensions of the image array to a $t_1$-$t_2$ score space; wherein said method consists of the steps of:
   creating a feature vector from said $t_1$-$t_2$ score space;
   performing a regression method to correlate the feature vector with a property of the food product; and
   creating an output of the properly for continuous monitoring and feed back control of operating conditions of the process;
   wherein one or more other physical process measurements are combined with information contained in the feature vector to correlate the physical process measurements with the property.

59. A method according to claim 58 wherein a regression method is performed on the physical process measurements before creating the output of the property.

60. A method according to claim 58 wherein said physical process measurement is one selected from the group consisting of: chip moisture content, chip oil content, chip weight per ten, dough moisture.

61. A method according to claim 58 wherein one or more acoustic measurements of a characterizing product are combined with information contained in the feature vector to correlate the acoustic measurements with the property.

62. A method according to claim 61 wherein a regression method is performed on the acoustic measurements before creating the output of the property.

63. A method according to claim 58 wherein one or more acoustic measurements of a characterizing product and one or more other physical process measurements are combined with information contained in the feature vector to correlate said acoustic measurements and said physical process measurements with the property.

64. A method according to claim 58 wherein the property of the food product is selected from the group consisting of: blister level, toast points, taste, texture, crispness, crunchiness, peak break force.

* * * * *